US007326686B2

(12) United States Patent
Blaschuk et al.

(10) Patent No.: US 7,326,686 B2
(45) Date of Patent: *Feb. 5, 2008

(54) COMPOUNDS AND METHODS FOR REGULATING CELL ADHESION

(75) Inventors: Orest W Blaschuk, Westmount (CA); Barbara J Gour, Kemptville (CA)

(73) Assignee: Adherex Inc., Ottawa (CA)

( * ) Notice: Subject to any disclaimer, the term of this patent is extended or adjusted under 35 U.S.C. 154(b) by 434 days.

This patent is subject to a terminal disclaimer.

(21) Appl. No.: 10/648,854

(22) Filed: Aug. 25, 2003

(65) Prior Publication Data

US 2004/0132651 A1    Jul. 8, 2004

Related U.S. Application Data

(63) Continuation of application No. 09/778,026, filed on Feb. 5, 2001, now abandoned, which is a continuation of application No. 08/939,853, filed on Sep. 29, 1997, now Pat. No. 6,203,788.

(51) Int. Cl.
*A61K 38/08* (2006.01)
*A61K 38/10* (2006.01)
*A61K 38/16* (2006.01)

(52) U.S. Cl. ............................ 514/12; 514/13; 514/14; 514/15; 514/16; 514/17

(58) Field of Classification Search ............... None
See application file for complete search history.

(56) References Cited

U.S. PATENT DOCUMENTS

| 5,231,082 | A | 7/1993 | Schasteen | 514/11 |
|---|---|---|---|---|
| 5,352,667 | A | 10/1994 | Lider et al. | 514/19 |
| 5,470,966 | A | 11/1995 | Hirano et al. | 536/23.5 |
| 5,510,628 | A | 4/1996 | Georger, Jr. et al. | 257/32 |
| 5,585,351 | A | 12/1996 | Ranscht | 514/12 |
| 5,591,432 | A | 1/1997 | Bronson et al. | 424/130.1 |
| 5,646,250 | A | 7/1997 | Suzuki | 530/350 |
| 5,665,590 | A | 9/1997 | Yang | 435/6 |
| 5,792,743 | A | 8/1998 | Schachner | 514/2 |
| 6,203,788 | B1* | 3/2001 | Blaschuk et al. | 424/93.7 |
| 6,419,923 | B1* | 7/2002 | Tripp et al. | 424/94.65 |
| 6,498,142 | B1* | 12/2002 | Sampath et al. | 514/12 |

FOREIGN PATENT DOCUMENTS

| EP | 406 428 B1 | 1/1995 |
|---|---|---|
| WO | WO 91/04745 | 4/1991 |
| WO | WO 92/08731 | 5/1992 |
| WO | WO 94/11401 | 5/1994 |
| WO | WO 96/40781 | 12/1996 |
| WO | WO 97/07209 | 2/1997 |
| WO | WO 98/45319 | 10/1998 |

OTHER PUBLICATIONS

Alexander et al., "An N-Cadherin-Like Protein Contributes to Solute Barrier Maintenance in Cultured Endothelium," *Journal of Cellular Physiology 156*: 610-618, 1993.
Ali et al., "Conformationally Constrained Peptides and Semipeptides Derived from RGD as Potent Inhibitors of the Platelet Fibrinogen Receptor and Platelet Aggregation," *J. Med. Chem. 37(6)*: 769-780, 1994.
Berkow, R. (ed.), *The Merck Manual of Diagnosis and Therapy*, Merck, Sharpe & Dohme Research Laboratories, Rahway, New Jersey, 1992, pp. 1488-1489.
Blakemore, "Remyelination of CNS axons by Schwann cells transplanted from the sciatic nerve," *Nature 266*: 68-69, 1977.
Blaschuk et al., "Identification of a Conserved Region Common to Cadherins and Influenza Strain A Hemagglutinins," *J. Mol. Biol. 211*: 679-682, 1990.
Blaschuk et al., "Identification of a Cadherin Cell Adhesion Recognition Sequence," *Developmental Biology 139*: 227-229, 1990.
Blaschuk et al., "E-Cadherin, estrogens and cancer: is there a connection?" *The Canadian Journal of Oncology 4(4)*: 291-301, 1994.
Blaschuk and Farookhi, "Estradiol Stimulates Cadherin Expression in Rat Granulosa Cells," *Developmental Biology 136*: 564-567, 1989.
Bottenstein and Sato, "Growth of a rat neuroblastoma cell line in serum-free supplemented medium," *Proc.Natl. Acad. Sci. USA 76(1)*: 514-517, 1979.
Brecknell et al., "Bridge grafts of Fibroblast Growth Factor-4-Secreting Schwannoma Cells Promote Functional Axonal Regeneration in the Nigrostriatal Pathway of the Adult Rat," *Neuroscience 74(3)*: 775-784, 1996.
Brockes et al., "Studies on Cultured Rat Schwann Cells. I. Establishment of Purified Populations from Cultures of Peripheral Nerve," *Brain Research 165*: 105-118, 1979.
Brook et al., "Morphology and Migration of Cultured Schwann Cells Transplanted Into the Fimbria and Hippocampus in Adult Rats," *GLIA 9*: 292-304, 1993.
Byers et al., "Fibroblast Growth Factor Receptors Contain a Conserved HAV Region Common to Cadherins and Influenza Strain A Hemagglutinins: A Role in Protein-Protein Interactions?," *Developmental Biology 152*: 411-414, 1992.

(Continued)

*Primary Examiner*—Jeffrey Edwin Russel
(74) *Attorney, Agent, or Firm*—Seed IP Law Group PLLC

(57) ABSTRACT

Methods for using modulating agents to enhance or inhibit cadherin-mediated cell adhesion in a variety of in vivo and in vitro contexts are provided. In particular, the modulating agents may be used in the therapy of multiple sclerosis and other demyelinating diseases. The modulating agents comprise at least one cadherin cell adhesion recognition sequence (HAV) or an antibody or fragment thereof that specifically binds to a cadherin cell adhesion recognition sequence. Modulating agents may additionally comprise one or more cell adhesion recognition sequences recognized by other adhesion molecules. Such modulating agents may, but need not, be linked to a targeting agent, drug and/or support material.

8 Claims, 16 Drawing Sheets-

OTHER PUBLICATIONS

Figure 3A:
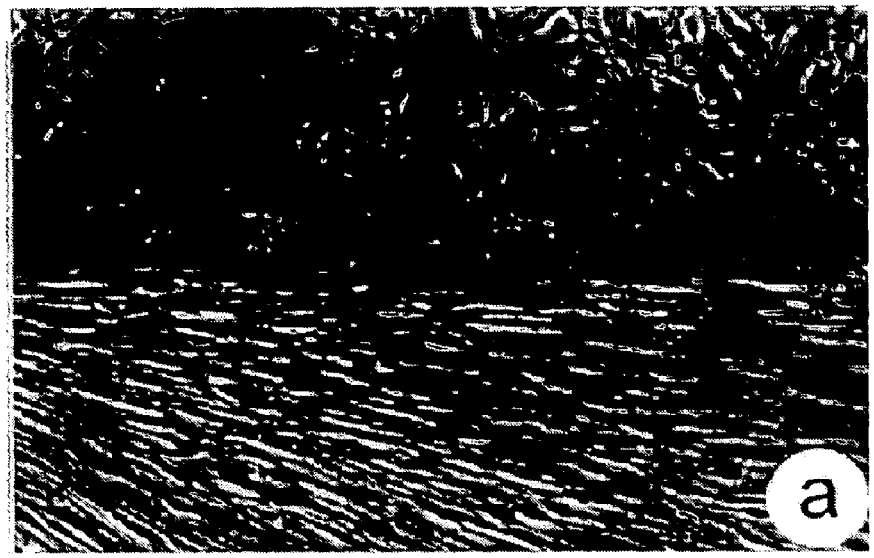

Cardarelli et al., "The Collagen Receptor α2β1, from MG-63 and HT1080 Cells, Interacts with a Cyclic RGD Peptide," *The Journal of Biological Chemistry* 267(32): 23159-23164, 1992.

Carlstedt et al., "Nerve Fibre Regeneration Across the PNS-CNS Interface at the Root-Spinal Cord Junction," *Brain Research Bulletin* 22: 93-102, 1989.

Cepek et al., "Expression of a candidate cadherin in T lymphocytes," *Proc. Natl. Acad. Sci. USA* 93: 6567-6571, Jun. 1996.

Chuah et al., "Differentiation and survival of rat olfactory epithelial neurons in dissociated cell culture," *Brain Research Developmental Brain Research* 60: 123-132, 1991.

Craig et al., "Concept and Progress in the Development of RGD-Containing Peptide Pharmaceuticals," *Biopolymers (Peptide Science)* 37: 157-175, 1995.

Doherty et al., "Neurite Outgrowth in Response to Transfected N-CAM and N-Cadherin Reveals Fundamental Differences in Neuronal Responsiveness to CAMS," *Neuron* 6: 247-258, Feb. 1991.

Doherty and Walsh, "CAM-FGF Receptor Interactions: A Model for Axonal Growth," *Molecular and Cellular Neuroscience* 8(Article No. 0049): 99-111, 1996.

Doherty and Walsh, "Signal transduction events underlying neurite outgrowth stimulated by cell adhesion molecules," *Current Opinion in Neurobiology* 4: 49-55, 1994.

Duncan et al., "Transplantation of oligodendrocytes and Schwann cells into the spinal cord of the myelin-deficient rat," *Journal of Neurocytology* 17: 351-360, Jun. 1988.

Fok-Seang et al., "An analysis of astrocytic cell lines with different abilities to promote axon growth," *Brain Research* 689: 207-223, 1995.

Fok-Seang et al., "Migration of Oligodendrocyte Precursors on Astrocytes and Meningeal Cells," *Developmental Biology* 171: 1-15, Sep. 1995.

Franz, "Percutaneous Absorption. On The Relevance Of In Vitro Data," *The Journal of Investigative Dermatology* 64(3): 190-195, Mar. 1975.

Franz, "The Finite Dose Technique as a Valid in Vitro Model for the Study of Percutaneous Absorption in Man," *Curr. Probl. Dermatol.* 7: 58-68, 1978.

Ghirnikar and Eng, "Astrocyte-Schwann Cell Interactions in Culture," *GLIA* 11: 367-377, 1994.

Gumbiner et al., "The Role of the Cell Adhesion Molecule Uvomorulin in the Formation and Maintenance of the Epithelial Junctional Complex," *The Journal of Cell Biology* 107: 1575-1587, Oct. 1988.

Iruela-Arispe et al., "Expression of SPARC during Development of the Chicken Chorioallantoic Membrane: Evidence for Regulated Proteolysis In Vivo," *Molecular Biology of the Cell* 6: 327-343, Mar. 1995.

Laird et al., "Gap Junction Turnover, Intracellular Trafficking, and Phosphorylation of Connexin43 in Brefeldin A-treated Rat Mammary Tumor Cells," *The Journal of Cell Biology* 131(5): 1193-1203, Dec. 1995.

Lee et al., "Expression of the Homotypic Adhesion Molecule E-Cadherin by Immature Murine Thymocytes and Thymic Epithelial Cells," *Journal of Immunology* 152: 5653-5659, 1994.

Letourneau et al., "Interactions of Schwann Cells with Neurites and with Other Schwann Cells Involve the Calcium-dependent Adhesion Molecule, N-cadherin," *Journal of Neurobiology* 22(7): 707-720, 1991.

Liuzzi and Lasek, "Astrocytes Block Axonal Regeneration in Mammals by Activating the Physiological Stop Pathway," *Science* 237: 642-645, 1987.

Lutz et al., "Secondary Structure of the HAV Peptide Which Regulates Cadherin-Cadherin Interaction," *Journal of Biomolecular Structure & Dynamics* 13(3): 447-455, 1995.

Matsuzaki et al., "cDNAs of Cell Adhesion Molecules of Different Specificity Induce Changes in Cell Shape and Border Formation in Cultured S180 Cells," *The Journal of Cell Biology* 110: 1239-1252, Apr. 1990.

McCarthy and Vellis, "Preparation of Separate Astroglial and Oligodendroglial Cell Cultures from Rat Cerebral Tissue," *J. Cell Biology* 85: 890-902, Jun. 1980.

Mege et al., "Construction of epithelioid sheets by transfection of mouse sarcoma cells with cDNAs for chicken cell adhesion molecules," *Proc. Natl. Acad. Sci. USA* 85: 7274-7278, Oct. 1988.

Munro et al., "Characterization of Cadherins Expressed by Murine Thymocytes," *Cellular Immunology* 169(Article No. 0123): 309-312, 1996.

Munro and Blaschuk, *Cell Adhesion and Invasion in Cancer Metastasis*, R.G. Landes Company, Austin, TX, 1996, Chapter 3, "The Structure, Function and Regulation of Cadherins," pp. 17-34.

Newton et al., "N-Cadherin Mediates Sertoli Cell-Spermatogenic Cell Adhesion," *Developmental Dynamics* 197: 1-13, 1993.

Nose et al., "Localization of Specificity Determining Sites in Cadherin Cell Adhesion Molecules," *Cell* 61: 147-155, 1990.

Orr, "Angiogenesis Research Offers New Approaches to Treatment of Disease," *Genetic Engineering News*, pp. 15-16, 42, May 1, 1996.

Overduin et al., "Solution Structure of the Epithelial Cadherin Domain Responsible for Selective Cell Adhesion," *Science* 267: 386-389, Jan. 20, 1995.

Redies and Takeichi, "Cadherins in the Developing Central Nervous System: An Adhesive Code for Segmental and Functional Subdivisions," *Developmental Biology* 180: 413-423, 1996.

Saffell et al., "Expression of a Dominant Negative FGF Receptor Inhibits Axonal Growth and FGF Receptor Phosphorylation Stimulated by CAMs," *Neuron*, pp. 231-242, Feb. 1997.

Samanen et al., "Development of a Small RGD Peptide Fibrinogen Receptor Antagonist with Potent Antiaggregatory Activity in Vitro," *J. Med. Chem.* 34(10): 3114-3125, 1991.

Shapiro et al., "Structural basis of cell-cell adhesion by cadherins," *Nature* 374: 327-337, Mar. 23, 1995.

Tsutsui et al., "Expression of Cadherin-Catenin Complexes in Human Leukemia Cell Lines," *J. Biochem.* 120: 1034-1039, 1996.

Wickelgren, "Breaking the Skin Barrier," *PS 12*: 86-88, 1996.

Willems et al., "Cadherin-dependent cell aggregation is affected by decapeptide derived from rat extracellular super-oxide dismutase," *FEBS Letters* 363: 289-292, 1995.

Williams et al., "Activation of the FGF Receptor Underlies Neurite Outgrowth Stimulated by L1, N-CAM, and N-Cadherin," *Neuron* 13: 583-594, Sep. 1994.

\* cited by examiner

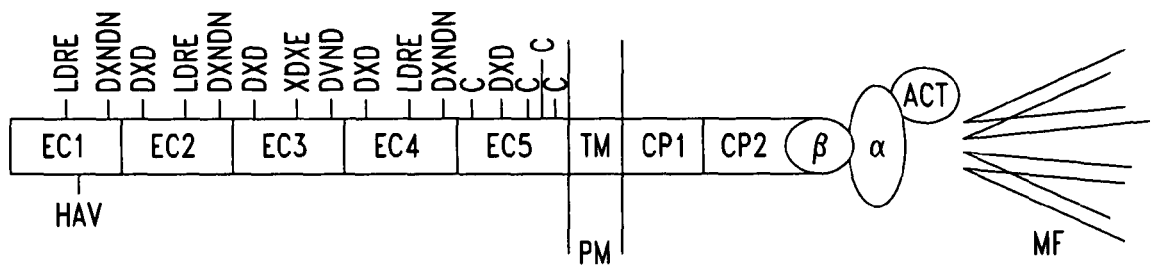

Fig. 1

Fig. 2

| | |
|---|---|
| human N-cad | DWVIPPINLPENSRGPFPQELVRIRSDRDKNLSLRYSVTGPGADQPPTGIFILNPISGQLSVTKPLDREQ |
| mouse N-cad | DWVIPPINLPENSRGPFPQELVRIRSDRDKNLSLRYSVTGPGADQPPTGIFIINPISGQLSVTKPLDREL |
| cow N-cad | DWVIPPINLPENSRGPFPQELVRIRSDRDKNLSLRYSVTGPGADQPPTGIFIINPISGQLSVTKPLDREL |
| human P-cad | DWVVAPISVPENGKGPFPQRLNQLKSWKDRDTKTFYSITGPGADSPPEGVFAVEKETGWLLLNKPLDREE |
| mouse P-cad | EWVMPPIFVPENGKGPFPQRLNQLKSNKDRGTKTFYSITGPGADSPPEGVFTIEKESGWLLLHMPLDREK |
| human E-cad | DWVIPPISCPENEKGPFPKNLVQIKSNKDKEGKVFYSITGQGADTPPVGVFIIERETGWLKVTEPLDRER |
| mouse E-cad | DWVIPPISCPENEKGEFPKNLVQIKSNRDKETKVFYSITGQGADKPPVGVFIIERETGWLKVTQPLDREA |

| | |
|---|---|
| human N-cad | IARFHLRAHAVDINGNQVENPIDIVINVIDMNDNRPEF |
| mouse N-cad | IARFHLRAHAVDINGNQVENPIDIDINVIDMNDNRPEF |
| cow N-cad | IARGHLRAHAVDINGNQVENPIDIVINVIDMNDNRPEF |
| human P-cad | IAKYELFGHAVSENGASVEDPMNISIIVTDQNDHKPKF |
| mouse P-cad | IVKYELYGHAVSENGASVEEPMNISTTVTDQNKNKPKF |
| human E-cad | IATYTLFSHAVSSNGNAVEDPMEILITVTDQNDNKPEF |
| mouse E-cad | IAKYILYSHAVSSNGEAVEDPMEIVITVTDQNDNRPEF |

Schwann cell adhesion to various substrates

SEQUENCE LISTING (1) GENERAL INFORMATION:

(iii) NUMBER OF SEQUENCES: 29

(2) INFORMATION FOR SEQ ID NO: 1:

(i) SEQUENCE CHARACTERISTICS:
      (A) LENGTH: 5 amino acids
      (B) TYPE: amino acid
      (C) STRANDEDNESS: single
      (D) TOPOLOGY: linear (xi) SEQUENCE DESCRIPTION: SEQ ID NO: 1:

Asp Xaa Asn Asp Asn
1               5

(2) INFORMATION FOR SEQ ID NO: 2:

(i) SEQUENCE CHARACTERISTICS:
      (A) LENGTH: 4 amino acids
      (B) TYPE: amino acid
      (C) STRANDEDNESS: single
      (D) TOPOLOGY: linear (xi) SEQUENCE DESCRIPTION: SEQ ID NO: 2:

Leu Asp Arg Glu
1

(2) INFORMATION FOR SEQ ID NO: 3:

(i) SEQUENCE CHARACTERISTICS:
        (A) LENGTH: 108 amino acids
        (B) TYPE: amino acid
        (C) STRANDEDNESS: <Unknown>
        (D) TOPOLOGY: linear (xi) SEQUENCE DESCRIPTION: SEQ ID NO: 3:

```
Asp Trp Val Ile Pro Pro Ile Asn Leu Pro Glu Asn Ser Arg Gly Pr
1               5                   10                  15
Phe Pro Gln Glu Leu Val Arg Ile Arg Ser Asp Arg Asp Lys Asn Le
            20                  25                  30
Ser Leu Arg Tyr Ser Val Thr Gly Pro Gly Ala Asp Gln Pro Pro Th
            35                  40                  45
Gly Ile Phe Ile Leu Asn Pro Ile Ser Gly Gln Leu Ser Val Thr Ly
            50                  55                  60
Pro Leu Asp Arg Glu Gln Ile Ala Arg Phe His Leu Arg Ala His Al
65                  70                  75                  80
Val Asp Ile Asn Gly Asn Gln Val Glu Asn Pro Ile Asp Ile Val Il
                85                  90                  95
Asn Val Ile Asp Met Asn Asp Asn Arg Pro Glu Phe
                100                 105
```

(2) INFORMATION FOR SEQ ID NO: 4:

(i) SEQUENCE CHARACTERISTICS:
        (A) LENGTH: 108 amino acids
        (B) TYPE: amino acid
        (C) STRANDEDNESS: <Unknown>
        (D) TOPOLOGY: linear (xi) SEQUENCE DESCRIPTION: SEQ ID NO: 4:

```
Asp Trp Val Ile Pro Pro Ile Asn Leu Pro Glu Asn Ser Arg Gly Pr
1               5                   10                  15
Phe Pro Gln Glu Leu Val Arg Ile Arg Ser Asp Arg Asp Lys Asn Le
            20                  25                  30
Ser Leu Arg Tyr Ser Val Thr Gly Pro Gly Ala Asp Gln Pro Pro Th
            35                  40                  45
Gly Ile Phe Ile Ile Asn Pro Ile Ser Gly Gln Leu Ser Val Thr Ly
            50                  55                  60
Pro Leu Asp Arg Glu Leu Ile Ala Arg Phe His Leu Arg Ala His Al
65                  70                  75                  80
Val Asp Ile Asn Gly Asn Gln Val Glu Asn Pro Ile Asp Ile Val Il
                85                  90                  95
Asn Val Ile Asp Met Asn Asp Asn Arg Pro Glu Phe
                100                 105
```

(2) INFORMATION FOR SEQ ID NO: 5:

(i) SEQUENCE CHARACTERISTICS:
        (A) LENGTH: 108 amino acids
        (B) TYPE: amino acid
        (C) STRANDEDNESS: <Unknown>
        (D) TOPOLOGY: linear (xi) SEQUENCE DESCRIPTION: SEQ ID NO: 5:

```
Asp Trp Val Ile Pro Pro Ile Asn Leu Pro Glu Asn Ser Arg Gly Pr
1               5                   10                  15
Phe Pro Gln Glu Leu Val Arg Ile Arg Ser Asp Arg Asp Lys Asn Le
```

```
                    20                  25                  30
Ser Leu Arg Tyr Ser Val Thr Gly Pro Gly Ala Asp Gln Pro Pro Th
             35                  40                  45

Gly Ile Phe Ile Ile Asn Pro Ile Ser Gly Gln Leu Ser Val Thr Ly
 50                  55                  60

Pro Leu Asp Arg Glu Leu Ile Ala Arg Phe His Leu Arg Ala His Al
 65                  70                  75                  80

Val Asp Ile Asn Gly Asn Gln Val Glu Asn Pro Ile Asp Ile Val Il
                 85                  90                  95

Asn Val Ile Asp Met Asn Asp Asn Arg Pro Glu Phe
                100                 105

(2) INFORMATION FOR SEQ ID NO: 6:

(i) SEQUENCE CHARACTERISTICS:
        (A) LENGTH: 108 amino acids
        (B) TYPE: amino acid
        (C) STRANDEDNESS: <Unknown>
        (D) TOPOLOGY: linear (xi) SEQUENCE DESCRIPTION: SEQ ID NO: 6:

Asp Trp Val Val Ala Pro Ile Ser Val Pro Glu Asn Gly Lys Gly Pr
 1               5                  10                  15

Phe Pro Gln Arg Leu Asn Gln Leu Lys Ser Asn Lys Asp Arg Asp Th
             20                  25                  30

Lys Ile Phe Tyr Ser Ile Thr Gly Pro Gly Ala Asp Ser Pro Pro Gl
             35                  40                  45

Gly Val Phe Ala Val Glu Lys Glu Thr Gly Trp Leu Leu Leu Asn Ly
 50                  55                  60

Pro Leu Asp Arg Glu Glu Ile Ala Lys Tyr Glu Leu Phe Gly His Al
 65                  70                  75                  80

Val Ser Glu Asn Gly Ala Ser Val Glu Asp Pro Met Asn Ile Ser Il
                 85                  90                  95

Ile Val Thr Asp Gln Asn Asp His Lys Pro Lys Phe
                100                 105

(2) INFORMATION FOR SEQ ID NO: 7:

(i) SEQUENCE CHARACTERISTICS:
        (A) LENGTH: 108 amino acids
        (B) TYPE: amino acid
        (C) STRANDEDNESS: <Unknown>
        (D) TOPOLOGY: linear (xi) SEQUENCE DESCRIPTION: SEQ ID NO: 7:

Glu Trp Val Met Pro Pro Ile Phe Val Pro Glu Asn Gly Lys Gly Pr
 1               5                  10                  15

Phe Pro Gln Arg Leu Asn Gln Leu Lys Ser Asn Lys Asp Arg Gly Th
             20                  25                  30

Lys Ile Phe Tyr Ser Ile Thr Gly Pro Gly Ala Asp Ser Pro Pro Gl
             35                  40                  45

Gly Val Phe Thr Ile Glu Lys Glu Ser Gly Trp Leu Leu Leu His Me
 50                  55                  60

Pro Leu Asp Arg Glu Lys Ile Val Lys Tyr Glu Leu Tyr Gly His Al
 65                  70                  75                  80

Val Ser Glu Asn Gly Ala Ser Val Glu Glu Pro Met Asn Ile Ser Il
                 85                  90                  95

Ile Val Thr Asp Gln Asn Asp Asn Lys Pro Lys Phe
```

(2) INFORMATION FOR SEQ ID NO: 8:

(i) SEQUENCE CHARACTERISTICS:
        (A) LENGTH: 108 amino acids
        (B) TYPE: amino acid
        (C) STRANDEDNESS: <Unknown>
        (D) TOPOLOGY: linear (xi) SEQUENCE DESCRIPTION: SEQ ID NO: 8:

```
Asp Trp Val Ile Pro Pro Ile Ser Cys Pro Glu Asn Glu Lys Gly Pr
1               5                   10                  15
Phe Pro Lys Asn Leu Val Gln Ile Lys Ser Asn Lys Asp Lys Glu Gl
            20                  25                  30
Lys Val Phe Tyr Ser Ile Thr Gly Gln Gly Ala Asp Thr Pro Pro Va
        35                  40                  45
Gly Val Phe Ile Ile Glu Arg Glu Thr Gly Trp Leu Lys Val Thr Gl
    50                  55                  60
Pro Leu Asp Arg Glu Arg Ile Ala Thr Tyr Thr Leu Phe Ser His Al
65                  70                  75                  80
Val Ser Ser Asn Gly Asn Ala Val Glu Asp Pro Met Glu Ile Leu Il
                85                  90                  95
Thr Val Thr Asp Gln Asn Asp Asn Lys Pro Glu Phe
            100                 105
```

(2) INFORMATION FOR SEQ ID NO: 9:

(i) SEQUENCE CHARACTERISTICS:
        (A) LENGTH: 108 amino acids
        (B) TYPE: amino acid
        (C) STRANDEDNESS: <Unknown>
        (D) TOPOLOGY: linear (xi) SEQUENCE DESCRIPTION: SEQ ID NO: 9:

```
Asp Trp Val Ile Pro Pro Ile Ser Cys Pro Glu Asn Glu Lys Gly Gl
1               5                   10                  15
Phe Pro Lys Asn Leu Val Gln Ile Lys Ser Asn Arg Asp Lys Glu Th
            20                  25                  30
Lys Val Phe Tyr Ser Ile Thr Gly Gln Gly Ala Asp Lys Pro Pro Va
        35                  40                  45
Gly Val Phe Ile Ile Glu Arg Glu Thr Gly Trp Leu Lys Val Thr Gl
    50                  55                  60
Pro Leu Asp Arg Glu Ala Ile Ala Lys Tyr Ile Leu Tyr Ser His Al
65                  70                  75                  80
Val Ser Ser Asn Gly Glu Ala Val Glu Asp Pro Met Glu Ile Val Il
                85                  90                  95
Thr Val Thr Asp Gln Asn Asp Asn Arg Pro Glu Phe
            100                 105
```

(2) INFORMATION FOR SEQ ID NO: 10:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (xi) SEQUENCE DESCRIPTION: SEQ ID NO: 10:

```
His Ala Val His Ala Val
1               5
```

(2) INFORMATION FOR SEQ ID NO: 11:

(i) SEQUENCE CHARACTERISTICS:
        (A) LENGTH: 13 amino acids
        (B) TYPE: amino acid
        (C) STRANDEDNESS: <Unknown>
        (D) TOPOLOGY: linear (xi) SEQUENCE DESCRIPTION: SEQ ID NO: 11:

Ser His Ala Val Ser His Ala Val Ser His Ala Val Ser
1               5                   10

(2) INFORMATION FOR SEQ ID NO: 12:

(i) SEQUENCE CHARACTERISTICS:
        (A) LENGTH: 5 amino acids
        (B) TYPE: amino acid
        (C) STRANDEDNESS: <Unknown>
        (D) TOPOLOGY: linear (xi) SEQUENCE DESCRIPTION: SEQ ID NO: 12:

Tyr Ile Gly Ser Arg
1               5

(2) INFORMATION FOR SEQ ID NO: 13:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 13:

Lys Tyr Ser Phe Asn Tyr Asp Gly Ser Glu
1               5                   10

(2) INFORMATION FOR SEQ ID NO: 14:

(i) SEQUENCE CHARACTERISTICS:
        (A) LENGTH: 17 amino acids
        (B) TYPE: amino acid
        (C) STRANDEDNESS: <Unknown>
        (D) TOPOLOGY: linear (xi) SEQUENCE DESCRIPTION: SEQ ID NO: 14:

Ile Trp Lys His Lys Gly Arg Asp Val Ile Leu Lys Lys Asp Val Ar
1               5                   10                  15
Phe (2) INFORMATION FOR SEQ ID NO: 15:

(i) SEQUENCE CHARACTERISTICS:
        (A) LENGTH: 47 amino acids
        (B) TYPE: amino acid
        (C) STRANDEDNESS: <Unknown>
        (D) TOPOLOGY: linear (xi) SEQUENCE DESCRIPTION: SEQ ID NO: 15:

Gly Val Asn Pro Tyr Ala Gln Ser Ser Gly Ser Leu Tyr Gly Ser Gl
1               5                   10                  15
Ile Tyr Ala Leu Cys Asn Gln Phe Tyr Thr Pro Ala Ala Thr Gly Le
                20                  25                  30
Tyr Val Asp Gln Tyr Leu Tyr His Tyr Cys Val Val Asp Pro Gln
            35                  40                  45

(2) INFORMATION FOR SEQ ID NO: 16:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 16:

Gln Ser Ser Gly Ser Leu Tyr Gly Ser Gln
1               5                   10

(2) INFORMATION FOR SEQ ID NO: 17:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (xi) SEQUENCE DESCRIPTION: SEQ ID NO: 17:

Gln Tyr Leu Tyr His Tyr Cys Val Val Asp
1               5                   10

(2) INFORMATION FOR SEQ ID NO: 18:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ix) FEATURE:
        (A) NAME/KEY: Modified-site
        (B) LOCATION: 1
        (D) OTHER INFORMATION: /note= "Residue may be acetylated"

(ix) FEATURE:
        (A) NAME/KEY: Modified-site
        (B) LOCATION: 10
        (D) OTHER INFORMATION: /note= "Residue may be amidated"

(xi) SEQUENCE DESCRIPTION: SEQ ID NO: 18:

Leu Tyr Ser His Ala Val Ser Ser Asn Gly
1               5                   10

(2) INFORMATION FOR SEQ ID NO: 19:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ix) FEATURE:
        (A) NAME/KEY: Modified-site
        (B) LOCATION: 1
        (D) OTHER INFORMATION: /note= "Residue may be acetylated"

(ix) FEATURE:
        (A) NAME/KEY: Modified-site
        (B) LOCATION: 10
        (D) OTHER INFORMATION: /note= "Residue may be amidated"

(xi) SEQUENCE DESCRIPTION: SEQ ID NO: 19:

Leu Phe Ser His Ala Val Ser Ser Asn Gly
1               5                   10

(2) INFORMATION FOR SEQ ID NO: 20:

```
    (i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ix) FEATURE:
        (A) NAME/KEY: Modified-site
        (B) LOCATION: 1
        (D) OTHER INFORMATION: /note= "Residue may be acetylated"

(ix) FEATURE:
        (A) NAME/KEY: Modified-site
        (B) LOCATION: 10
        (D) OTHER INFORMATION: /note= "Residue may be amidated"

(xi) SEQUENCE DESCRIPTION: SEQ ID NO: 20:

Leu Phe Gly His Ala Val Ser Glu Asn Gly
 1               5                  10

(2) INFORMATION FOR SEQ ID NO: 21:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ix) FEATURE:
        (A) NAME/KEY: Modified-site
        (B) LOCATION: 1
        (D) OTHER INFORMATION: /note= "Residue may be acetylated"

(ix) FEATURE:
        (A) NAME/KEY: Modified-site
        (B) LOCATION: 10
        (D) OTHER INFORMATION: /note= "Residue may be amidated"

(xi) SEQUENCE DESCRIPTION: SEQ ID NO: 21:

Leu Arg Ala His Ala Val Asp Ile Asn Gly
 1               5                  10

(2) INFORMATION FOR SEQ ID NO: 22:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ix) FEATURE:
        (A) NAME/KEY: Modified-site
        (B) LOCATION: 1
        (D) OTHER INFORMATION: /note= "Residue may be acetylated"

(ix) FEATURE:
        (A) NAME/KEY: Modified-site
        (B) LOCATION: 10
        (D) OTHER INFORMATION: /note= "Residue may be amidated"

(xi) SEQUENCE DESCRIPTION: SEQ ID NO: 22:

Leu Arg Ala His Ala Val Asp Val Asn Gly
 1               5                  10

(2) INFORMATION FOR SEQ ID NO: 23:

(i) SEQUENCE CHARACTERISTICS:
        (A) LENGTH: 10 amino acids
        (B) TYPE: amino acid
        (C) STRANDEDNESS: <Unknown>
        (D) TOPOLOGY: linear (ix) FEATURE:
```

```
        (A) NAME/KEY: Modified-site
        (B) LOCATION: 1
        (D) OTHER INFORMATION: /note= "Residue may be acetylated"

(ix) FEATURE:
        (A) NAME/KEY: Modified-site
        (B) LOCATION: 10
        (D) OTHER INFORMATION: /note= "Residue may be amidated"

(xi) SEQUENCE DESCRIPTION: SEQ ID NO: 23:

Met Arg Ala His Ala Val Asp Ile Asn Gly
 1               5                  10

(2) INFORMATION FOR SEQ ID NO: 24:

(i) SEQUENCE CHARACTERISTICS:
        (A) LENGTH: 16 amino acids
        (B) TYPE: amino acid
        (C) STRANDEDNESS: <Unknown>
        (D) TOPOLOGY: linear (ix) FEATURE:
        (A) NAME/KEY: Modified-site
        (B) LOCATION: 1
        (D) OTHER INFORMATION: /note= "Residue may be acetylated"

(ix) FEATURE:
        (A) NAME/KEY: Modified-site
        (B) LOCATION: 16
        (D) OTHER INFORMATION: /note= "Residue may be amidated"

(xi) SEQUENCE DESCRIPTION: SEQ ID NO: 24:

His Leu Gly Ala His Ala Val Asp Ile Asn Gly Asn Gln Val Glu Th
 1               5                  10                  15

(2) INFORMATION FOR SEQ ID NO: 25:

(i) SEQUENCE CHARACTERISTICS:
        (A) LENGTH: 15 amino acids
        (B) TYPE: amino acid
        (C) STRANDEDNESS: <Unknown>
        (D) TOPOLOGY: linear (ix) FEATURE:
        (A) NAME/KEY: Modified-site
        (B) LOCATION: 1
        (D) OTHER INFORMATION: /note= "Residue may be acetylated"

(ix) FEATURE:
        (A) NAME/KEY: Modified-site
        (B) LOCATION: 15
        (D) OTHER INFORMATION: /note= "Residue may be amidated"

(xi) SEQUENCE DESCRIPTION: SEQ ID NO: 25:

Phe His Leu Arg Ala His Ala Val Asp Ile Asn Gly Asn Gln Val
 1               5                  10                  15

(2) INFORMATION FOR SEQ ID NO: 26:

(i) SEQUENCE CHARACTERISTICS:
        (A) LENGTH: 6 amino acids
        (B) TYPE: amino acid
        (C) STRANDEDNESS: <Unknown>
        (D) TOPOLOGY: linear (xi) SEQUENCE DESCRIPTION: SEQ ID NO: 26:

Gly His Ala Val Ser Glu
 1               5

(2) INFORMATION FOR SEQ ID NO: 27:
```

```
        (i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (ix) FEATURE:
            (A) NAME/KEY: Modified-site
            (B) LOCATION: 1
            (D) OTHER INFORMATION: /note= "Residue may be acetylated"

(ix) FEATURE:
            (A) NAME/KEY: Modified-site
            (B) LOCATION: 6
            (D) OTHER INFORMATION: /note= "Residue may be amidated"

(xi) SEQUENCE DESCRIPTION: SEQ ID NO: 27:

Ala His Ala Val Ser Glu
1               5

(2) INFORMATION FOR SEQ ID NO: 28:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (ix) FEATURE:
            (A) NAME/KEY: Modified-site
            (B) LOCATION: 1
            (D) OTHER INFORMATION: /note= "Residue may be acetylated"

(ix) FEATURE:
            (A) NAME/KEY: Modified-site
            (B) LOCATION: 6
            (D) OTHER INFORMATION: /note= "Residue may be amidated"

(xi) SEQUENCE DESCRIPTION: SEQ ID NO: 28:

Ala His Ala Val Asp Ile
1               5

(2) INFORMATION FOR SEQ ID NO: 29:

(i) SEQUENCE CHARACTERISTICS:
            (A) LENGTH: 6 amino acids
            (B) TYPE: amino acid
            (C) STRANDEDNESS: <Unknown>
            (D) TOPOLOGY: linear (ix) FEATURE:
            (A) NAME/KEY: Modified-site
            (B) LOCATION: 1
            (D) OTHER INFORMATION: /note= "Residue may be acetylated"

(ix) FEATURE:
            (A) NAME/KEY: Modified-site
            (B) LOCATION: 6
            (D) OTHER INFORMATION: /note= "Residue may be amidated"

(xi) SEQUENCE DESCRIPTION: SEQ ID NO: 29:

Ser His Ala Val Ser Ser
1               5
```

COMPOUNDS AND METHODS FOR REGULATING CELL ADHESION

CROSS-REFERENCE TO RELATED APPLICATIONS

This application is a continuation of U.S. patent application Ser. No. 09/778,026, filed Feb. 5, 2001, now abandoned; which is a continuation of U.S. Ser. No. 08/939,853, filed Sep. 29, 1997, now issued as U.S. Pat. No. 6,203,788, which applications are incorporated herein by reference in their entireties.

BACKGROUND OF THE INVENTION

1. Field of the Invention

The present invention relates generally to methods for modulating cadherin-mediated processes, and more particularly to the use of modulating agents comprising a cadherin cell adhesion recognition sequence, or an antibody that specifically recognizes such a sequence, for inhibiting or enhancing functions such as cell adhesion.

2. Description of the Related Art

Multiple sclerosis (MS) is a chronic neurological disease that affects approximately 250,000 individuals in the United States. In a patient afflicted with MS, axons become demyelinated and oligodendrocytes die. Although the clinical course can vary, the most common form is manifested by relapsing neurological deficits, including paralysis, sensory deficits, and visual problems.

In MS and other demyelinating diseases, Schwann cells are generally excluded from areas of demyelination and, following axon damage, regeneration generally fails at Schwann cell-astrocyte boundaries (Carlstedt et al., *Brain Res. Bulletin* 22:93-102, 1989). Inhibition of Schwann cell migration and boundary formation by astrocytes appears to play a significant part in limiting sportaneous repair processes in the damaged central nervous system (CNS).

In theory, Schwann cells from the peripheral nervous system could be used to replace damaged oligodendrocytes in the CNS. However, the efficacy of such treatment has been limited by poor Schwann cell migration and by boundary formation. When Schwann cells are grafted into the adult CNS, they can migrate along blood vessels and meningeal surfaces, but form boundaries where they meet astrocytes. These boundaries can present an obstacle for regenerating axons. Thus, recruitment of regenerating axons into Schwann cell grafts is frequently poor, and axons remaining in the grafts fail to grow back into CNS tissue unless their target neurons are immediately adjacent (Brecknell et al., *Neurosci.* 74:775-784, 1996; Liuzzi and Lasak, *Science* 237:642-645,1987). Transplanted Schwann cells have been found to be capable of remyelinating central axons of normal (Blakemore, *Nature* 266:68-69, 1977) or myelin deficient rats (Duncan et al., *J. Neurocytol.* 17:351-360, 1988), but in both of these cases the area of remyelination is limited to the region close to the transplantation site.

Other approaches to developing a definitive treatment for MS have also been largely unsuccessful. Corticosteroids and ACTH may hasten recovery from acute exacerbations, but they do not prevent future attacks, the development of additional disabilities or chronic progression of MS. In addition, the substantial side effects of steroid treatments make these drugs undesirable for long-term use. Other toxic compounds, such as azathioprine, a purine antagonist, cyclophosphamide and cyclosporine have also been used to treat symptoms of MS. Like corticosteroids, however, these drugs are beneficial at most for a short term and are highly toxic. More recently, cytokines such as IFN-γ and IFN-β have been administered in attempts to alleviate the symptoms of MS, but such treatment has led to a clinical exacerbation for some patients. Betaseron has also been employed, but with no effect on the rate of clinical deterioration, and side effects were commonly observed.

Accordingly, there is a need in the art for methods for treating MS that are effective and are not associated with the disadvantages of the present treatments. The present invention fulfills this need and further provides other related advantages.

BRIEF SUMMARY OF THE INVENTION

The present invention provides methods for modulating cadherin-mediated cell adhesion. Within one aspect, methods are provided for treating a demyelinating neurological disease, such as multiple sclerosis, in a mammal, comprising administering to a mammal a cell adhesion modulating agent that inhibits cadherin-mediated cell adhesion. The modulating agent may comprise the sequence His-Ala-Val or may comprise an antibody or fragment thereof that specifically binds to a cadherin cell adhesion recognition sequence. A modulating agent may be administered by implantation with Schwann cells or oligodendrocyte progenitor cells and/or may be administered within a pharmaceutical composition.

Within further aspects, the present invention provides methods for reducing unwanted cellular adhesion in a mammal, comprising administering to a mammal a cell adhesion modulating agent that inhibits unwanted cadherin-mediated cell adhesion resulting from surgery, injury, disease or inflammation. The modulating agent may comprise the sequence His-Ala-Val or may comprise an antibody or fragment thereof that specifically binds to a cadherin cell adhesion recognition sequence.

The present invention further provides methods for enhancing the delivery of a drug through the skin of a mammal, comprising contacting epithelial cells of a mammal with a cell adhesion modulating agent that inhibits cadherin-mediated cell adhesion and a drug, wherein the step of contacting is performed under conditions and for a time sufficient to allow passage of said drug across said epithelial cells. The modulating agent may comprise the sequence His-Ala-Val or may comprise an antibody or fragment thereof that specifically binds to a cadherin cell adhesion recognition sequence.

Within further aspects, methods are provided for enhancing the delivery of a drug to a tumor in a mammal, comprising administering to a mammal a cell adhesion modulating agent that inhibits cadherin-mediated cell adhesion and a drug. The modulating agent may comprise 3-16 amino acid residues including the sequence His-Ala-Val or may comprise an antibody or fragment thereof that specifically binds to a cadherin cell adhesion recognition sequence.

In a related aspect, the present invention provides methods for treating cancer in a mammal, comprising administering to a mammal a cell adhesion modulating agent that inhibits cadherin-mediated cell adhesion and a drug. The modulating agent may comprise 3-16 amino acid residues including the sequence His-Ala-Val or may comprise an antibody or fragment thereof that specifically binds to a cadherin cell adhesion recognition sequence.

Within further aspects, methods are provided for inhibiting angiogenesis in a mammal, comprising administering to a mammal a cell adhesion modulating agent that inhibits cadherin-mediated cell adhesion. The modulating agent may comprise the sequence His-Ala-Val or may comprise an antibody or fragment thereof that specifically binds to a cadherin cell adhesion recognition sequence.

The present invention further provides methods for enhancing drug delivery to the CNS of a mammal, comprising administering to a mammal a cell adhesion modulating agent that inhibits cadherin-mediated cell adhesion. The modulating agent may comprise 3-16 amino acid residues including the sequence His-Ala-Val or may comprise an antibody or fragment thereof that specifically binds to a cadherin cell adhesion recognition sequence.

Within further aspects, the present invention provides methods for enhancing wound healing in a mammal, comprising contacting a wound in a mammal with a cell adhesion modulating agent that enhances cadherin-mediated cell adhesion. The modulating agent may comprise the sequence His-Ala-Val or may comprise an antibody or fragment thereof that specifically binds to a cadherin cell adhesion recognition sequence.

In a related aspect, methods are provided for enhancing adhesion of foreign tissue implanted within a mammal, comprising contacting a site of implantation of foreign tissue in a mammal with a cell adhesion modulating agent that enhances cadherin-mediated cell adhesion. The modulating agent may comprise the sequence His-Ala-Val or may comprise an antibody or fragment thereof that specifically binds to a cadherin cell adhesion recognition sequence.

Within further aspects, the present invention provides methods for inducing apoptosis in a cadherin-expressing cell, comprising contacting a cadherin-expressing cell with a cell adhesion modulating agent that inhibits cadherin-mediated cell adhesion. The modulating agent may comprise the sequence His-Ala-Val or may comprise an antibody or fragment thereof that specifically binds to a cadherin cell adhesion recognition sequence.

The present invention further provides methods for modulating the immune system of a mammal, comprising administering to a mammal a pharmaceutical composition comprising a cell adhesion modulating agent that inhibits cadherin-mediated cell adhesion. The modulating agent may comprise the sequence His-Ala-Val or may comprise an antibody or fragment thereof that specifically binds to a cadherin cell adhesion recognition sequence.

Within another aspect, the present invention provides methods for preventing pregnancy in a mammal, comprising administering to a mammal a cell adhesion modulating agent that inhibits cadherin-mediated cell adhesion. The modulating agent may comprise the sequence His-Ala-Val or may comprise an antibody or fragment thereof that specifically binds to a cadherin cell adhesion recognition sequence.

In still further aspects, the present invention provides methods for increasing vasopermeability in a mammal, comprising administering to a mammal a cell adhesion modulating agent that inhibits cadherin-mediated cell adhesion. The modulating agent may comprise the sequence His-Ala-Val or may comprise an antibody or fragment thereof that specifically binds to a cadherin cell adhesion recognition sequence.

The present invention also provides, within further aspects, methods for enhancing and/or directing neurite outgrowth, comprising contacting a neuron with a cell adhesion modulating agent that enhances cadherin-mediated cell adhesion. The modulating agent may comprise the sequence His-Ala-Val or may comprise an antibody or fragment thereof that specifically binds to a cadherin cell adhesion recognition sequence.

Within related aspects, methods are provided for treating spinal cord injuries in a mammal, comprising administering to a mammal a cell adhesion modulating agent that enhances cadherin-mediated cell adhesion. The modulating agent may comprise the sequence His-Ala-Val or may comprise an antibody or fragment thereof that specifically binds to a cadherin cell adhesion recognition sequence.

The present invention also provides methods for inhibiting synaptic stability in a mammal, comprising administering to a mammal a cell adhesion modulating agent that inhibits cadherin-mediated cell adhesion. The modulating agent may comprise the sequence His-Ala-Val or may comprise an antibody or fragment thereof that specifically binds to a cadherin cell adhesion recognition sequence.

In still further aspects, methods are provided for identifying an agent capable of modulating cadherin-mediated cell adhesion. One such method comprises the steps of: (a) contacting Schwann cells with an astrocytic surface in the presence of candidate modulating agent; (b) washing the astrocytic surface to remove non-attached cells; and (c) comparing the number of Schwann cells attached to the astrocytic surface with the number of Schwann cells attached to an astrocytic surface in the absence of candidate modulating agent. Another method for identifying an agent capable of modulating cadherin-mediated cell adhesion comprises the steps of: (a) contacting Schwann cells with polylysine- and/or laminin-coated surface in the presence of candidate modulating agent; (b) washing the surface to remove non-attached cells; (c) contacting attached Schwann cells with an astrocyte-coated surface; and (d) comparing the migration of the attached Schwann cells with the migration in the absence of candidate modulating agent.

A further method for identifying an agent capable of modulating cadherin-mediated cell adhesion comprises the steps of: (a) culturing neurons on a monolayer of cells that express N-cadherin in the presence and absence of a candidate agent, under conditions and for a time sufficient to allow neurite outgrowth, wherein the cells are transfected with a polynucleotide encoding N-cadherin and wherein the cells do not express a detectable level of N-cadherin in the absence of transfection with such a polynucleotide; (b) determining a mean neurite length for the neurons; and (c) comparing the mean neurite length for neurons cultured in the presence of candidate agent to the neurite length for neurons cultured in the absence of candidate agent.

Yet another method for identifying an agent capable of modulating cadherin-mediated cell adhesion comprises the steps of: (a) culturing cells that express a cadherin in the presence and absence of a candidate agent, under conditions and for a time sufficient to allow cell adhesion; and (b) visually evaluating the extent of cell adhesion among the cells.

A further method for identifying an agent capable of modulating cadherin-mediated cell adhesion comprises the steps of: (a) culturing normal rat kidney (NRK) cells in the presence and absence of a candidate agent, under conditions and for a time sufficient to allow cell adhesion; and (b) comparing the level of cell surface E-cadherin for cells cultured in the presence of candidate agent to the level for cells cultured in the absence of candidate agent.

Another method for identifying an agent capable of modulating cadherin-mediated cell adhesion comprises the steps of: (a) contacting an epithelial surface of skin with a test marker in the presence and absence of candidate agent; and (b) comparing the amount of test marker that passes through the skin in the presence of candidate agent to the amount that passes through skin in the absence of candidate agent.

Within further aspects, the present invention provides methods for detecting the presence of cadherin-expressing cells in a sample, comprising: (a) contacting a sample with an antibody that binds to a modulating agent comprising the sequence His-Ala-Val under conditions and for a time sufficient to allow formation of an antibody-cadherin complex; and (b) detecting the level of antibody-cadherin complex.

Within a related aspect, the present invention provides kits for detecting the presence of cadherin-expressing cells in a sample, comprising: (a) an antibody that binds to a modulating agent comprising the sequence His-Ala-Val; and (b) a detection reagent.

The present invention also provides, within a further aspect, kits for enhancing transdermal drug delivery, comprising: (a) a skin patch; and (b) a cell adhesion modulating agent, wherein the modulating agent comprises the sequence His-Ala-Val, and wherein the modulating agent inhibits cadherin-mediated cell adhesion.

Figure 7A:
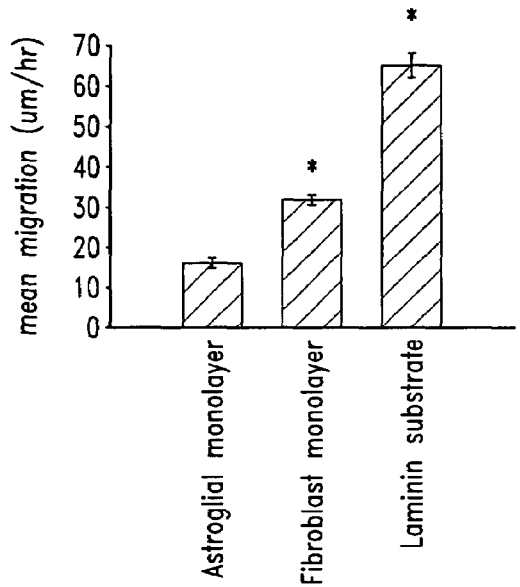
Figure 7B:
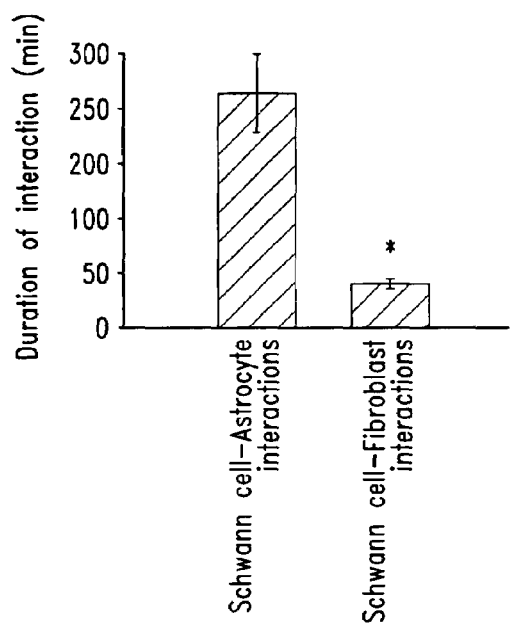

Within another aspect, the present invention provides methods for identifying a compound capable of modulating cadherin-mediated cell adhesion, comprising: (a) contacting an antibody that binds to a modulating agent comprising the sequence His-Ala-Val with a test compound; and (b) detecting the level of antibody that binds to the test compound, and therefrom identifying a compound capable of modulating cadherin-mediated cell adhesion.

These and other aspects of the invention will become evident upon reference to the following detailed description and attached drawings. All references disclosed herein are hereby incorporated by reference in their entirety as if each were individually noted for incorporation.

BRIEF DESCRIPTION OF THE DRAWINGS

FIG. 1 is a diagram depicting the structure of classical cadherins. The five extracellular domains are designated EC1-EC5, the hydrophobic domain that transverses the plasma membrane (PM) is represented by TM, and the two cytoplasmic domains are represented by CP1 and CP2. The calcium binding motifs are shown by DXNDN (SEQ ID NO: 1), DXD and LDRE (SEQ ID NO. 2). The cell adhesion recognition (CAR) sequence, HAV, is shown within EC1. Cytoplasmic proteins β-catenin (β), α-catenin (α) and α-actinin (ACT), which mediate the interaction between cadherins and microfilaments (MF) are also shown.

FIG. 2 provides the amino acid sequences of mammalian classical cadherin EC1 domains: human N-cadherin (SEQ ID NO: 3), mouse N-cadherin (SEQ ID NO: 4), cow N-cadherin (SEQ ID NO: 5), human P-cadherin (SEQ ID NO: 6), mouse P-cadherin (SEQ ID NO: 7), human E-cadherin (SEQ ID NO: 8) and mouse E-cadherin (SEQ ID NO: 9).

FIGS. 3A-3D are photographs showing cellular boundaries generated in culture. FIGS. 3A and 3C represent Schwann cell-astrocyte boundaries. FIG. 3D is the fluorescent counterpart of 3C. Astrocytes (green) are stained with anti-GFAP and Schwann cells (orange) are stained with anti GAP-43. Notice the Schwann cells surrounding one lone astrocyte and only occasional “finger-like” processes of Schwann cells overlapping the astrocytes. FIG. 3B depicts a typical Schwann cell-skin fibroblast “boundary”; note the lack of a defined territorial margin with clear cellular overlap. Scale bar 50 μm.

FIGS. 4A and 4B are graphs depicting Schwann cell migration upon a variety of cellular substrates as determined by the inverted coverslip migration assay. 1 mm×2 mm glass fragments laden with fluorescently labeled Schwann cells were inverted onto various substrates and left for 2 days. The number of migrated Schwann cells per unit distance was recorded and is shown as FIG. 4A; the furthest distance of migration by the Schwann cells from the edge of the fragment is shown as FIG. 4B. Schwann cells migrated poorly upon primary astroglial cultures and upon the astrocytic cell line A7 compared to fibroblastic or meningeal cell substrates. The most migration was found upon the non-cellular substrate, laminin. All data are expressed as the mean±S.E.C. of at least three separate determinations; each determination consisting of at least 8-12 fragments per group. One way analysis of variance performed upon the maximum migratory distances revealed a statistical difference <0.001 between at least one of the groups. A post hoc multiple comparisons test (Tukey test) revealed significant differences (p<0.01) between the groups marked with (*) and the control astrocytes.

FIGS. 5A and 5B are graphs depicting the migration of Schwann cells on astrocyte matrix as determined by the inverted-fragmented-coverslip migration assay. 1 mm×2 mm glass fragments laden with fluorescently labeled Schwann cells were inverted onto whole astrocyte surfaces, astrocyte matrix or laminin substrates and left for 2 days. The number of Schwann cells per unit distance is given as FIG. 5A, with the maximum migration values as FIG. 5B. Schwann cells migrated poorly upon astrocytes but considerably better upon astrocyte matrix or laminin. All data are expressed as the mean±S.E.M. of at least three separate determinations, each determination consisting of at least 8-12 fragments per group. One way analysis of variance (ANOVA) performed upon the maximum migratory distances revealed a statistical difference <0.001 between at least one of the groups. A post hoc multiple comparisons test (Tukey test) revealed significant differences (p<0.01) between the groups marked with (*) and the control astrocytes.

FIGS. 6A and 6B are graphs depicting the migration of Schwann cells on laminin, and the effects of astroglial soluble factors as determined by the inverted-fragmented-coverslip migration assay. 1 mm×2 mm glass fragments laden with fluorescently labeled Schwann cells were inverted onto laminin, and left for 2 days in either serum-free (SF) medium or astrocyte conditioned medium (ACM). The number of Schwann cells per unit distance is given as FIG. 6A, with the maximum migration values as FIG. 6B. Schwann cells were found to migrate less well upon laminin in the absence of serum (c.f. FIG. 1) and considerably better in ACM. All data are expressed as the mean±S.E.M. of at least three separate determinations, each determination consisting of at least 8-12 fragments per group. A student's t-test was performed giving p<0.001 (indicated by *).

FIGS. 7A and 7B are graphs, and FIG. 7C is a diagram, depicting the results of timelapse analysis. FIG. 7A shows the mean migration rates of single Schwann cells plated onto astrocytic, fibroblastic or laminin substrates and filmed for a period of 6 hours. The position of the cell body was recorded (represented diagrammatically as FIG. 7C) every 30 minutes and the displacement calculated. The number of cells recorded was 30 upon astrocytes, 25 upon fibroblasts and 30 upon laminin. Schwann cells were found to migrate fastest on laminin, slowest on astrocytes and slightly faster on fibroblasts. One way ANOVA performed on the data revealed a statistical difference (p<0.001) between at least one of the groups. A post hoc multiple comparisons test (Tukey test) revealed significant differences (p<0.01) between the groups marked with (*) and the control astrocytes. FIG. 7B shows the duration of interaction between Schwann cells and astrocytes and Schwann cells and fibroblasts. The durations of 50 Schwann cell-astrocyte interactions and 45 Schwann cell-fibroblast interactions were recorded. Interactions between Schwann cells and astrocytes were found to be almost 5 times longer than those with fibroblasts. A student's t-test was performed and p<0.001 (*). All data are expressed as the mean±S.E.M. Scale bar in 5C is 50 µm.

Figure 8A:
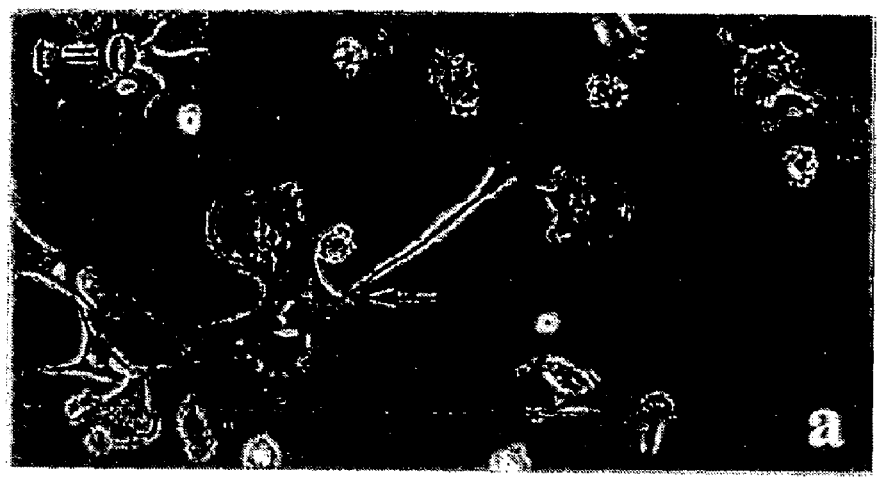
Figure 8B:
Figure 8C:
Figure 8D:
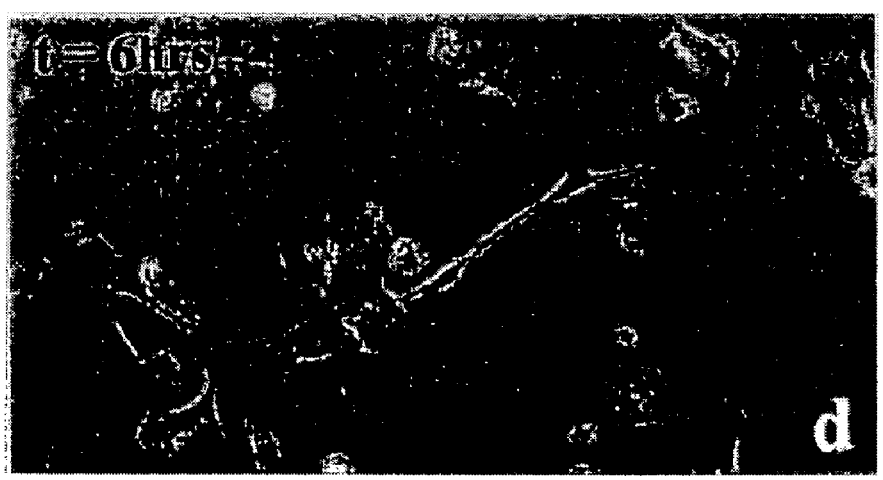
Figure 8E:

FIGS. 8A-E are photographs illustrating Schwann cells colliding with sparsely plated astroglia. This series of photographs was obtained from the timelapse videomicroscopy apparatus, each picture preceding the next by a period of 2 hours. In FIG. 8A, a group of two Schwann cells encounters astroglia (labeled *). The growth cone of one Schwann cell contacts an astrocyte (arrow indicates first contact). In FIG. 8B, the first Schwann cell process continues to explore the astrocyte surface whilst the perikarya of the second Schwann cell contacts another astrocyte (arrow). The first contact persists beyond the 8 hours of recording. The second contact is more short-lived, although astrocyte and Schwann cell remain in close approximation. Scale bar 20 µm.

Figure 9:
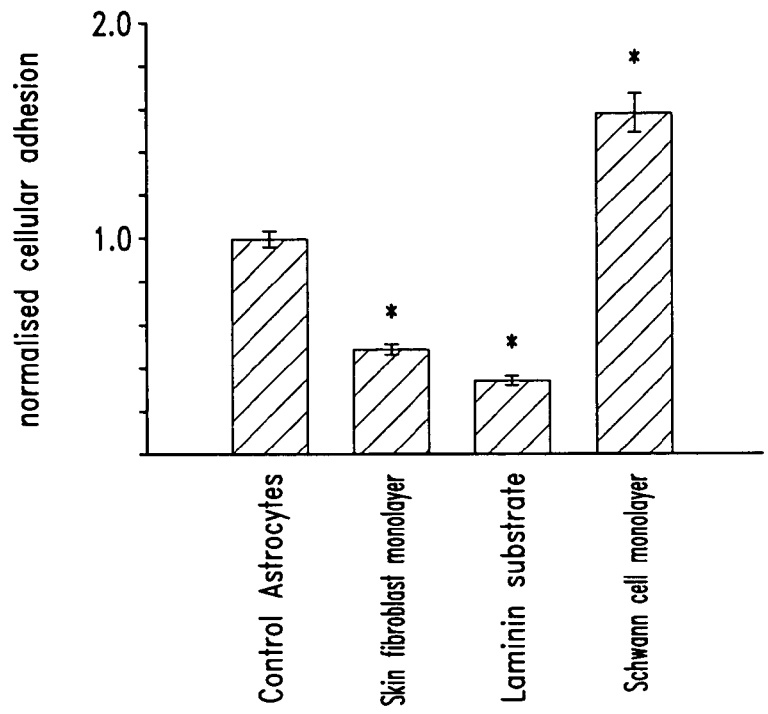

FIG. 9 is a histogram depicting the adhesion of Schwann cells to various substrates. 20,000 Dil-labelled Schwann cells were plated onto a 13 mm glass coverslip coated with laminin, a complete monolayer of astrocytes, fibroblasts or Schwann cells and then placed onto a shaking (25 rpm) platform for 30 minutes. After washing, the number of cells found still to be attached were counted. More cells were found to have stuck on the astrocytic surfaces than on fibroblasts or laminin whereas even more had stuck to Schwann cells. Note that the speed of migration as determined by the inverted-fragmented-coverslip migration assay is inversely proportional to the adhesivity of the substrate. All data are normalized to control and expressed as the mean±S.E.M. of at least three separate determinations. One way analysis of variance (ANOVA) was performed and revealed a statistical difference<0.001 between at least one of the groups. A post hoc multiple comparisons test (Tukey test) revealed significant differences (p<0.01) between the groups marked with (*) and the control astrocytes.

Figure 10A:
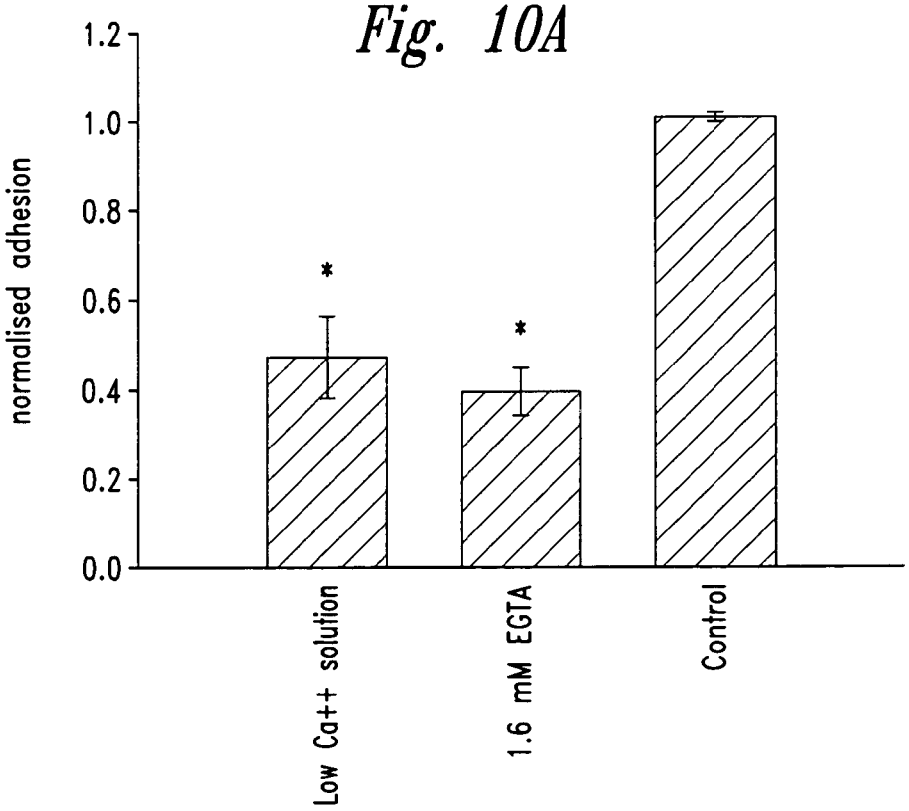
Figure 10B:
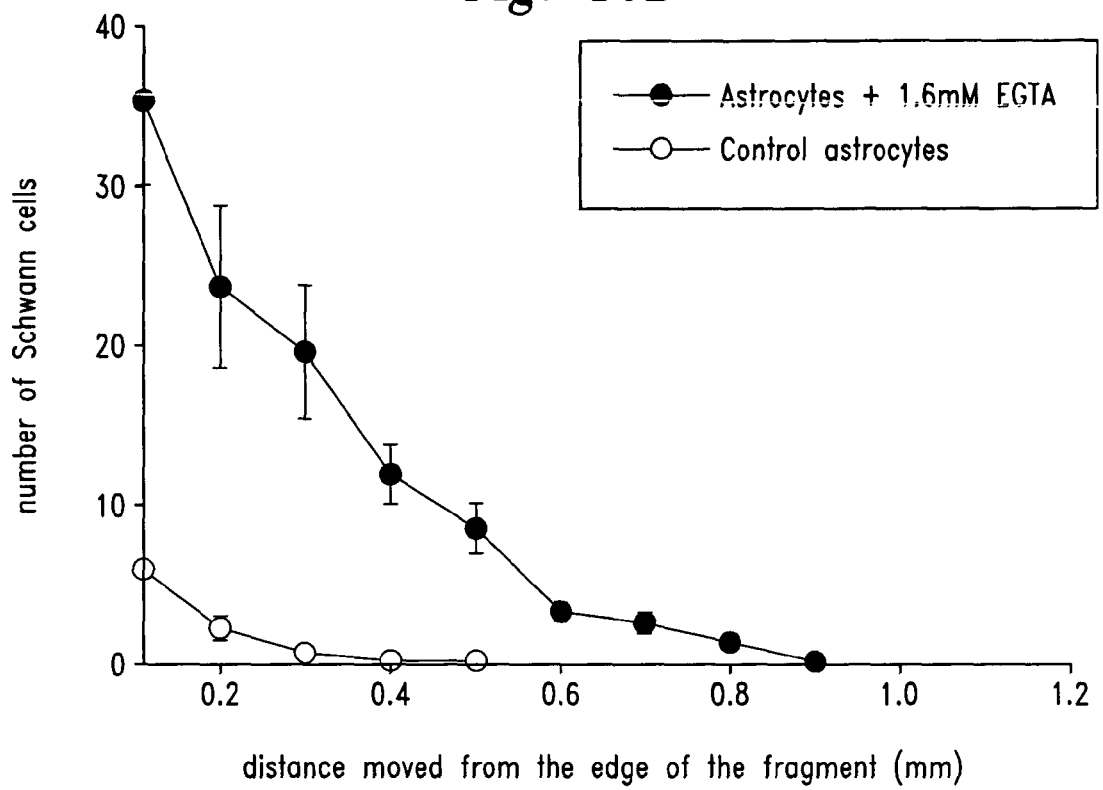
Figure 10C:
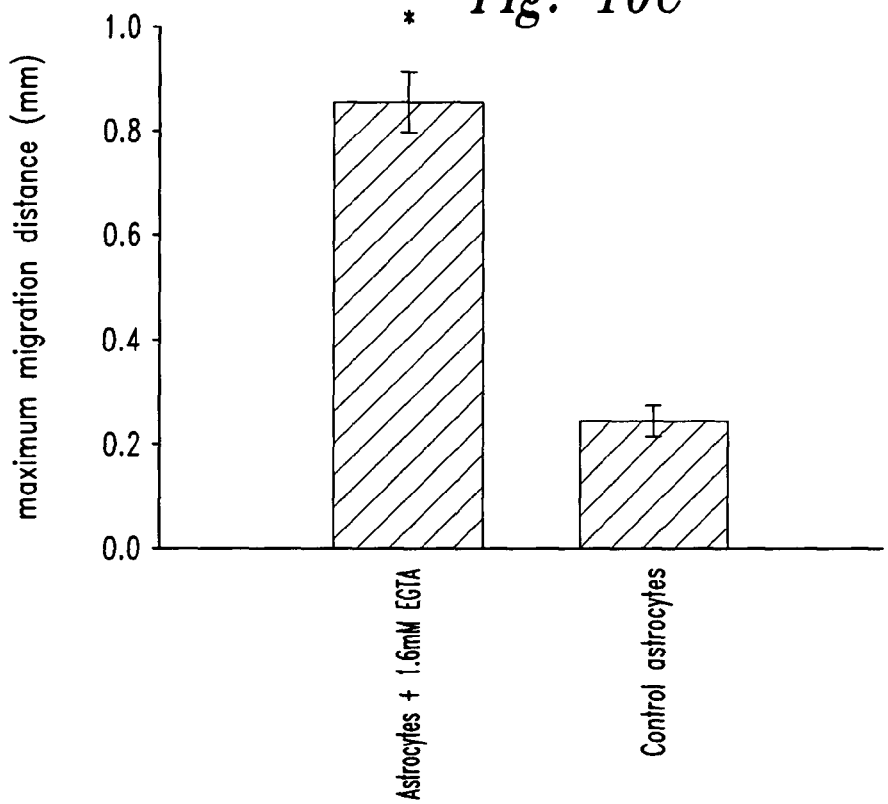

FIGS. 10A-C are graphs depicting the effect of lowering extracellular calcium in reducing Schwann cell-astrocyte adhesion and improving Schwann cell migration on astrocytes. FIG. 10A shows Schwann cell-astrocyte adhesion in reduced calcium solutions. The adhesion assay was performed on astrocytes in normal calcium solution (control), in 0.2 mM calcium (low calcium) solution and in the presence of 1.6 mM EGTA. Adhesion was greatly reduced in both the latter cases. All data are normalized to control and expressed as the mean±S.E.M. of at least three separate determinations. One way analysis of variance (ANOVA) was performed and revealed a statistical difference<0.001 between at least one of the groups. A post hoc multiple comparisons test (Tukey test) revealed significant differences (p<0.01) between the groups marked with (*) and the control astrocytes. FIGS. 10B and C: Schwann cell migration on astrocytes with reduced extracellular calcium as determined by the inverted coverslip migration assay. The number of cells migrated per unit distance is shown in FIG. 10B with maximum distances represented in FIG. 10C. Schwann cells were found to have migrated further on astrocytes in the presence of reduced calcium than on astrocytes in the presence of normal calcium levels. A student's t-test revealed significant difference between the maximum distances (*p<0.001).

Figure 11A:
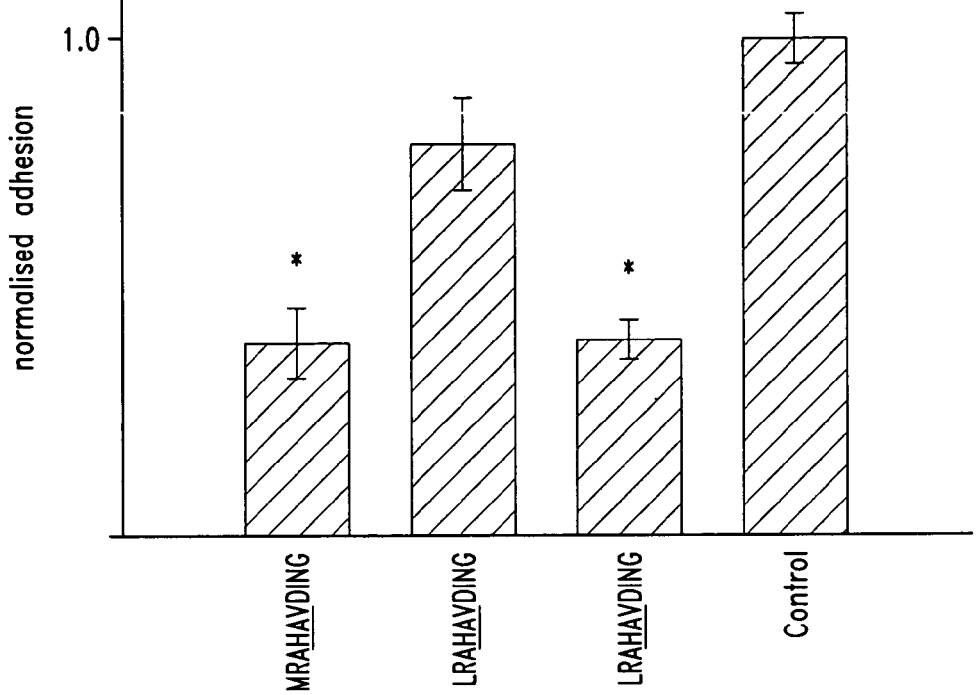
Figure 11B:
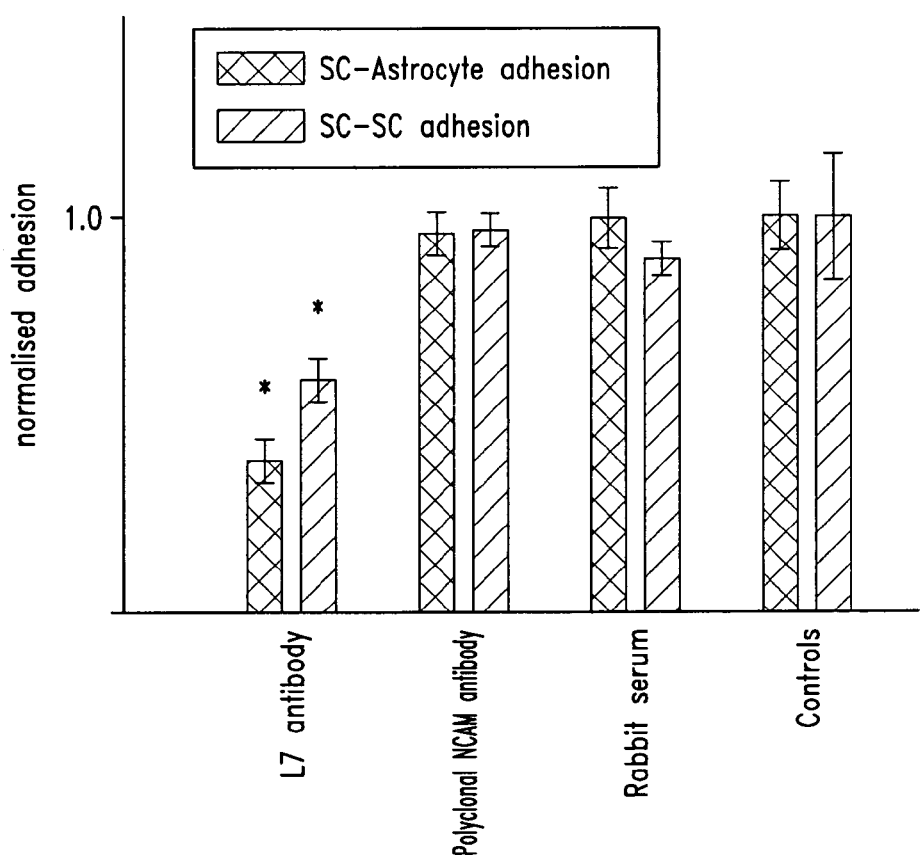
Figure 11C:
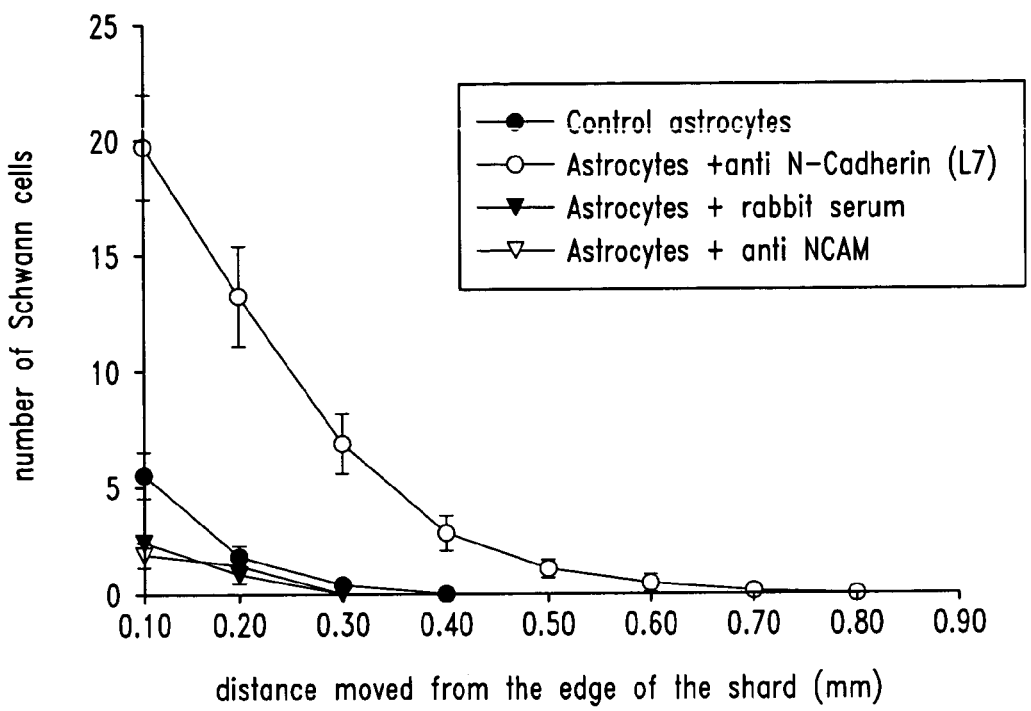
Figure 11D:
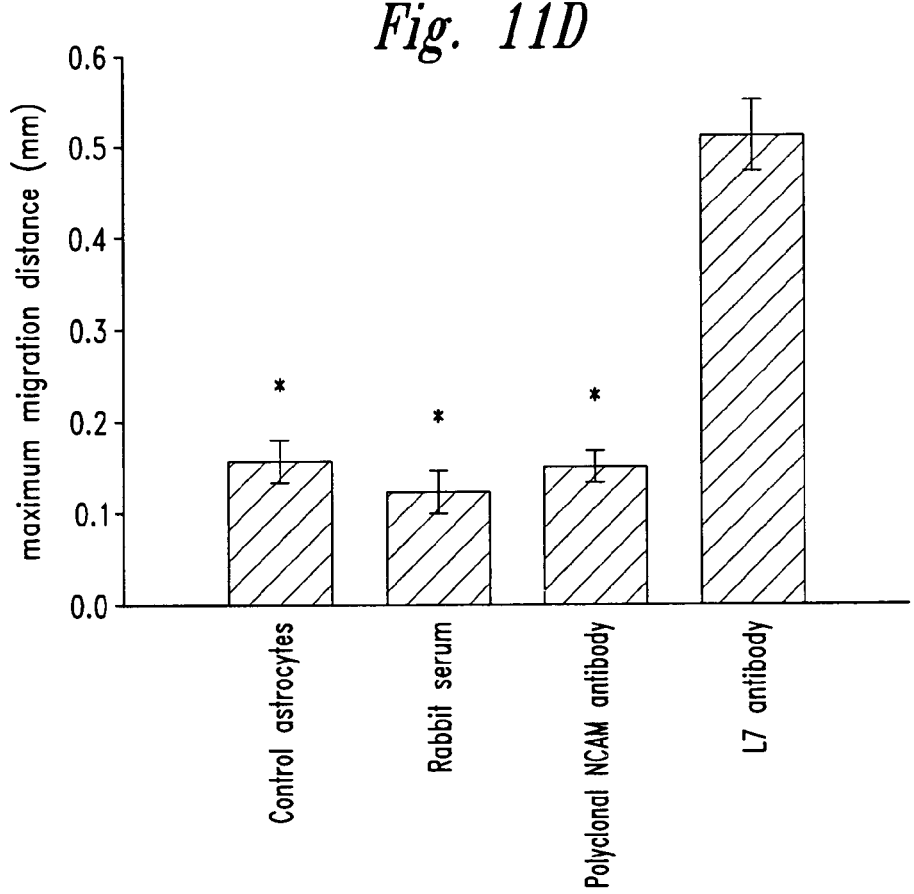

FIGS. 11A-D are graphs depicting the effect of cadherin disruption by representative modulating agents in reducing intercellular adhesion and promoting Schwann cell migration on astrocytes. FIG. 11A shows Schwann cell-astrocyte adhesion in the presence of representative modulating agents. The adhesion assay was performed in the presence of modulating agent or a similar (control) peptide without the HAV sequence. The modulating agents were found to significantly reduce Schwann cell-astrocyte adhesion compared to either the non-HAV peptide or control. FIG. 11B shows the ability of N-cadherin blocking antibodies (rabbit anti-N-cadherin CAR sequence antibodies; designated as L7) to reduce Schwann cell adhesion to astrocytes and Schwann cells. Neither a rabbit polyclonal antibody directed against N-CAM nor the rabbit serum were found to alter intercellular adhesion. All data in FIGS. 11A and B are normalized with respect to control and expressed as the mean±S.E.M. of at least three separate determinations. One way analysis of variance (ANOVA) was performed and revealed a statistical difference<0.001 between at least one of the groups. A post hoc multiple comparisons test (Tukey test) revealed significant differences (p<0.01) between the groups marked with (*) and the control astrocytes. FIGS. 11C and 11D: Increased Schwann cell migration on astrocytes in the presence of cadherin-function blocking antibodies (L7). FIG. 11C represents number of cells migrated per unit distance, with FIG. 11D representing maximum migration distance. Only the anti-cadherin CAR sequence antibody L7 caused a significant difference as determined by post hoc analysis (Tukey test) following one way ANOVA (*p<0.001). The L7 antibody increased migration on astrocyes up to three fold compared to control.

Figure 12A:
Figure 12B:
Figure 12C:
Figure 12D:

FIGS. 12A-D are photographs showing Schwann cell migration as visualized by the inverted coverslip migration assay. 1 mm×2 mm glass fragments laden with fluorescently labeled Schwann cells were inverted onto various substrates and left for 2-3 days. FIG. 12A shows a fluorescent photograph of Schwann cell migration normally observed on control astrocyes, with little spread from the edge of the inverted fragment. FIG. 12B shows a fluorescent photograph of Schwann cell migration on skin fibroblasts. Note the considerable number of cells leaving the edge of the inverted fragment. FIGS. 12C and 12D show a phase and fluorescent photograph, respectively, of Schwann cell migration on astroctyes in the presence of the anti-cadherin CAR sequence antiserum (L7). Notice the astrocyte monolayer in FIG. 12C is intact. Scale bar for FIGS. 12A and B are 40 µm; for FIGS. 12C and 12D the scale bar is 100 µm.

DETAILED DESCRIPTION OF THE INVENTION

As noted above, the present invention provides methods for modulating cadherin-mediated processes, such as cell adhesion. In general, to modulate cadherin-mediated cell adhesion, a cadherin-expressing cell is contacted with a cell adhesion modulating agent (also referred to herein as a "modulating agent") either in vivo or in vitro. A modulating agent may comprise the classical cadherin cell adhesion recognition (CAR) sequence HAV (i.e., His-Ala-Val), with or without one or more additional CAR sequences, as described below. Alternatively, or in addition, a modulating agent may comprise an antibody, or antigen-binding fragment thereof, that specifically binds to a cadherin CAR sequence. Within certain aspects, the methods provided herein inhibit cell adhesion. Such methods may generally be used, for example, to treat diseases or other conditions characterized by undesirable cell adhesion or to facilitate drug delivery to a specific tissue or tumor. Within other aspects, the methods provided herein may be used to enhance cell adhesion (e.g., to supplement or replace stitches or to facilitate wound healing). Within still further aspects, methods are provided for enhancing and/or directing neurite outgrowth. Within one such aspect, the present invention provides methods for treating a demyelinating disorder, such as multiple sclerosis.

Certain aspects of the present invention are based on the discovery that cadherin-mediated cell adhesion is involved in regulating Schwann cell adhesion to astrocytes and in limiting Schwann cell migration. Cadherins are a rapidly expanding family of cell adhesion molecules (CAMs). The classical cadherins are integral membrane glycoproteins that generally promote cell adhesion through homophilic interactions (a cadherin on the surface of one cell binds to an identical cadherin on the surface of another cell), although cadherins also appear to be capable of forming heterotypic complexes with one another under certain circumstances and with lower affinity. Cadherins have been shown to regulate epithelial, endothelial, neural and cancer cell adhesion, with different cadherins expressed on different cell types. N (neural)—cadherin is predominantly expressed by neural cells, endothelial cells and a variety of cancer cell types. E (epithelial)—cadherin is predominantly expressed by epithelial cells. Other cadherins are P (placental)—cadherin, which is found in human skin and R (retinal)—cadherin. A detailed discussion of the classical cadherins is provided in Munro et al., 1996, *In: Cell Adhesion and Invasion in Cancer Metastasis*, P. Brodt, ed., pp. 17-34 (RG Landes Company, Austin Tex.).

The structures of the classical cadherins are generally similar. As illustrated in FIG. 1, cadherins are composed of five extracellular domains (EC1-EC5), a single hydrophobic domain (TM) that transverses the plasma membrane (PM), and two cytoplasmic domains (CP1 and CP2). The calcium binding motifs DXNDN (SEQ ID NO: 1), DXD and LDRE (SEQ ID NO: 2) are interspersed throughout the extracellular domains. The first extracellular domain (EC1) contains the classical cadherin CAR sequence, HAV (His-Ala-Val), along with flanking sequences on either side of the CAR sequence that appear to play a role in conferring specificity. The three-dimensional solution and crystal structures of the EC1 domain have been determined (Overduin et al., *Science* 267:386-389, 1995; Shapiro et al., *Nature* 374:327-337, 1995). Sequences of the EC1 domain of some naturally occurring cadherins are shown in FIG. 2 and SEQ ID NOs: 3 to 9.

Cell Adhesion Modulating Agents

The term "cell adhesion modulating agent," as used herein, refers to a molecule comprising at least one cadherin CAR sequence, generally HAV (His-Ala-Val), and/or an antibody (or antigen-binding fragment thereof) that specifically binds a cadherin CAR sequence. Within embodiments in which inhibition of cell adhesion is desired, a modulating agent may contain one HAV sequence or multiple HAV sequences, which may be adjacent to one another (i.e., without intervening sequences) or in close proximity (i.e., separated by peptide and/or non-peptide linkers to give a distance between the CAR sequences that ranges from about 0.1 to 400 nm). For example, a modulating agent with adjacent HAV sequences may comprise the peptide HAVHAV (SEQ ID NO: 10). A representative modulating agent with HAV sequences in close proximity may comprise the sequence SHAVSHAVSHAVS (SEQ ID NO: 11). One or more antibodies, or fragments thereof, may similarly be used within such embodiments, either alone or in combination with one or more CAR sequences.

A modulating agent as described herein may additionally comprise a CAR sequence for one or more different adhesion molecules (including, but not limited to, other CAMs) and/or one or more antibodies or fragments thereof that bind to such sequences. Linkers may, but need not, be used to separate such CAR sequence(s) and/or antibody sequence(s) from the HAV sequence(s) and/or each other. Such modulating agents may generally be used within methods in which it is desirable to simultaneously disrupt cell adhesion mediated by multiple adhesion molecules. As used herein, an "adhesion molecule" is any molecule that mediates cell adhesion via a receptor on the cell's surface. Adhesion molecules include members of the cadherin gene superfamily that are not classical cadherins (e.g., proteins that do not contain an HAV sequence and/or one or more of the other characteristics recited above for classical cadherins), such as desmogleins (Dsg) and desmocollins (Dsc); integrins; members of the immunoglobulin supergene family, such as N-CAM; and other uncategorized transmembrane proteins, such as occludin) as well as extracellular matrix proteins such as laminin, fibronectin, collagens, vitronectin, entactin and tenascin. Preferred CAR sequences for inclusion within a modulating agent include Arg-Gly-Asp (RGD), which is bound by integrins (see Cardarelli et al., *J. Biol. Chem.* 267:23159-64, 1992); Tyr-Ile-Gly-Ser-Arg (YIGSR; SEQ ID NO: 12), which is bound by α6β1 integrin; KYS-FNYDGSE (SEQ ID NO: 13), which is bound by N-CAM; the N-CAM heparan sulfate-binding site IWKHKGRD-VILKKDVRF (SEQ ID NO: 14), the putative Dsc CAR sequences YAT, FAT and YAS; the putative Dsg CAR sequence RAL; and/or the putative occludin CAR sequence GVNPTAQSSGSLYGSQIYALCNQFYT-PAATGLYVDQYLYHYCVVDPQ-E (SEO ID NO; 31), or derivatives thereof such as QSSGSLYGSQ (SEQ ID NO: 16) and QYLYHYCVVD (SEQ ID NO: 17).

A linker may be any molecule (including peptide and/or non-peptide sequences as well as single amino acids or other molecules), that does not contain a CAR sequence and that can be covalently linked to at least two peptide sequences. Using a linker, HAV-containing peptides and other peptide or protein sequences may be joined head-to-tail (i.e., the linker may be covalently attached to the carboxyl or amino group of each peptide sequence), head-to-side chain and/or tail-to-side chain. Modulating agents comprising one or more linkers may form linear or branched structures. Within one embodiment, modulating agents having a branched structure comprise three different CAR sequences, such as RGD, YIGSR and HAV. Within another embodiment, modulating agents having a branched structure comprise RGD, YIGSR (SEQ ID NO: 12), HAV and KYSFNYDGSE (SEQ ID NO: 13). In a third embodiment, modulating agents having a branched structure comprise HAV, YAT, FAT, YAS and RAL. Bi-functional modulating agents that comprise an HAV sequence with flanking E-cadherin-specific sequences joined via a linker to an HAV sequence with flanking N-cadherin-specific sequences are also preferred for certain embodiments. Linkers preferably produce a distance between CAR sequences between 0.1 to 10,000 nm, more preferably about 0.1-400 nm. A separation distance between recognition sites may generally be determined according to the desired function of the modulating agent. For inhibitors of cell adhesion, the linker distance should be small (0.1-400 nm). For enhancers of cell adhesion, the linker distance should be 400-10,000 nm. One linker that can be used for such purposes is $(H_2N(CH_2)_nCO_2H)_m$, or derivatives thereof, where n ranges from 1 to 10 and m ranges from 1 to 4000. For example, if glycine ($H_2NCH_2CO_2H$) or a multimer thereof is used as a linker, each glycine unit corresponds to a linking distance of 2.45 angstroms, or 0.245 nm, as determined by calculation of its lowest energy conformation when linked to other amino acids using molecular modeling techniques. Similarly, aminopropanoic acid corresponds to a linking distance of 3.73 angstroms, aminobutanoic acid to 4.96 angstroms, aminopentanoic acid to 6.30 angstroms and amino hexanoic acid to 6.12 angstroms. Other linkers that may be used will be apparent to those of ordinary skill in the art and include, for example, linkers based on repeat units of 2,3-diaminopropanoic acid, lysine and/or ornithine. 2,3-Diaminopropanoic acid can provide a linking distance of either 2.51 or 3.11 angstroms depending on whether the side-chain amino or terminal amino is used in the linkage. Similarly, lysine can provide linking distances of either 2.44 or 6.95 angstroms and ornithine 2.44 or 5.61 angstroms. Peptide and non-peptide linkers may generally be incorporated into a modulating agent using any appropriate method known in the art.

Within embodiments in which enhancement of cell adhesion is desired, a modulating agent may contain multiple HAV sequences, or antibodies that specifically bind to such sequences, joined by linkers as described above. Enhancement of cell adhesion may also be achieved by attachment of multiple modulating agents to a support material, as discussed further below.

The total number of CAR sequences (including HAV, with or without other CAR sequences derived from one or more adhesion molecules) present within a modulating agent may range from 1 to a large number, such as 100, preferably from 1 to 10, and more preferably from 1 to 5. Peptide modulating agents comprising multiple CAR sequences typically contain from 3 to about 1000 amino acid residues, preferably from 4 to 50 residues. When non-peptide linkers are employed, each CAR sequence of the modulating agent is present within a peptide that generally ranges in size from 3 to 50 residues in length, preferably from 3 to 25 residues, more preferably from 3 to 16 residues and still more preferably from 4 to 16 residues. Additional residue(s) that may be present on the N-terminal and/or C-terminal side of a CAR sequence may be derived from sequences that flank the HAV sequence within one or more naturally occurring cadherins (e.g., N-cadherin, E-cadherin, P-cadherin, R-cadherin or other cadherins containing the HAV sequence) with or without amino acid substitutions and/or other modifications. Flanking sequences for endogenous N-, E-, P- and R-cadherin are shown in FIG. 2, and in SEQ ID NOs: 3 to 9. Alternatively, additional residues present on one or both sides of the CAR sequence(s) may be unrelated to an endogenous sequence (e.g., residues that facilitate purification or other manipulation and/or residues having a targeting or other function).

A modulating agent may contain sequences that flank the HAV sequence on one or both sides that are designed to confer specificity for cell adhesion mediated by one or more specific cadherins, resulting in tissue and/or cell-type specificity. Suitable flanking sequences for conferring specificity include, but are not limited to, endogenous sequences present in one or more naturally occurring cadherins. Modulating agents having a desired specificity may be identified using the representative screens provided herein. Within preferred embodiments, the addition of appropriate endogenous sequences may result in modulating agents that specifically disrupt N-cadherin, P-cadherin or E-cadherin mediated cell adhesion. For example, the peptide modulating agent LYSHAVSSNG (SEQ ID NO: 18) or LFSHAVSSNG (SEQ ID NO: 19) may be used to disrupt E-cadherin mediated function, the peptide modulating agent LFGHAVSENG (SEQ ID NO: 20) may be used to disrupt P-cadherin mediated function, and the peptide LRAHAVDING (SEQ ID NO: 21) may be used to disrupt N-cadherin mediated function.

To facilitate the preparation of modulating agents having a desired specificity, nuclear magnetic resonance (NMR) and computational techniques may be used to determine the conformation of a peptide that confers a known specificity. NMR is widely used for structural analysis of molecules. Cross-peak intensities in nuclear Overhauser enhancement (NOE) spectra, coupling constants and chemical shifts depend on the conformation of a compound. NOE data provide the interproton distance between protons through space. This information may be used to facilitate calculation of the lowest energy conformation for the HAV sequence. Conformation may then be correlated with tissue specificity to permit the identification of peptides that are similarly tissue specific or have enhanced tissue specificity.

Modulating agents may be polypeptides or salts thereof, containing only amino acid residues linked by peptide bonds, or may contain non-peptide regions, such as linkers. Peptide regions of a modulating agent may comprise residues of L-amino acids, D-amino acids, or any combination thereof. Amino acids may be from natural or non-natural sources, provided that at least one amino group and at least one carboxyl group are present in the molecule; α- and β-amino acids are generally preferred. The 20 L-amino acids commonly found in proteins are identified herein by the conventional three-letter or one-letter abbreviations indicated in Table 1, and the corresponding D-amino acids are designated by a lower case one letter symbol.

TABLE 1

Amino acid one-letter and three-letter abbreviations

| | | |
|---|---|---|
| A | ALA | ALANINE |
| R | ARG | ARGININE |
| D | ASP | ASPARTIC ACID |
| N | ASN | ASPARAGINE |
| C | CYS | CYSTEINE |
| Q | GLN | GLUTAMINE |
| E | GLU | GLUTAMIC ACID |
| G | GLY | GLYCINE |
| H | HIS | HISTIDINE |
| I | ILE | ISOLEUCINE |
| L | LEU | LEUCINE |
| K | LYS | LYSINE |
| M | MET | METHIONINE |
| F | PHE | PHENYLALANINE |
| P | PRO | PROLINE |
| S | SER | SERINE |
| T | THR | THREONINE |
| W | TRP | TRYPTOPHAN |
| Y | TYR | TYROSINE |
| V | VAL | VALINE |

A modulating agent may also contain rare amino acids (such as 4-hydroxyproline or hydroxylysine), organic acids or amides and/or derivatives of common amino acids, such as amino acids having the C-terminal carboxylate esterified (e.g., benzyl, methyl or ethyl ester) or amidated and/or having modifications of the N-terminal amino group (e.g., acetylation or alkoxycarbonylation), with or without any of a wide variety of side-chain modifications and/or substitutions (e.g., methylation, benzylation, t-butylation, tosylation, alkoxycarbonylation, and the like). Preferred derivatives include amino acids having a C-terminal amide group. Residues other than common amino acids that may be present with a modulating agent include, but are not limited to, 2-mercaptoaniline, 2-mercaptoproline, ornithine, diaminobutyric acid, α-aminoadipic acid, m-aminomethylbenzoic acid and α,β-diaminopropionic acid.

Certain preferred modulating agents for use within the present invention comprise at least one of the following sequences: LRAHAVDING (SEQ ID NO: 21), LRAHAVDVNG (SEQ ID NO: 22), MRAHAVDING (SEQ ID NO: 23), HLGAHAVDINGNQVET (SEQ ID NO: 24), FHLRAHAVDINGNQV (SEQ ID NO: 25), LYSHAVSSNG (SEQ ID NO: 18), LFSHAVSSNG (SEQ ID NO: 19), LFGHAVSENG (SEQ ID NO: 20), GHAVSE (SEQ ID NO: 26), AHAVSE (SEQ ID NO: 27), AHAVDI (SEQ ID NO: 28) and/or SHAVSS (SEQ ID NO: 29), wherein each amino acid residue may, but need not, be modified as described above. Within one particularly preferred group, modulating agents comprise an N-terminal acetyl group and/or a C-terminal amide group. Representative modulating agents comprising a C-terminal amide group include: LRAHAVDING-NH$_2$ (SEQ ID NO: 21), LRAHAVDVNG-NH$_2$ (SEQ ID NO: 22), MRAHAVDING-NH$_2$ (SEQ ID NO: 23), HLGA-HAVDINGNQVET-NH$_2$ (SEQ ID NO: 24), FHLRA-HAVDINGNQV-NH$_2$ (SEQ ID NO: 25), LYSHAVSSNG-NH$_2$ (SEQ ID NO: 18), LFSHAVSSNG-NH$_2$ (SEQ ID NO: 19), LFGHAVSENG-NH$_2$ (SEQ ID NO: 20), GHAVSE-NH$_2$ (SEQ ID NO: 26), AHAVSE-NH$_2$ (SEQ ID NO: 27), AHAVDI-NH$_2$ (SEQ ID NO: 28), SHAVSS-NH$_2$ (SEQ ID NO: 29) and compounds comprising such sequences or derivatives thereof. Representative modulating agents comprising a N-terminal acetyl group and a C-terminal amide group include: N-Ac-LRAHAVDING-NH$_2$ (SEQ ID NO: 21), N-Ac-LRAHAVDVNG-NH$_2$ (SEQ ID NO: 22), N-Ac-MRAHAVDING-NH$_2$ (SEQ ID NO: 23), N-Ac-HLGA-HAVDINGNQVET-NH$_2$ (SEQ ID NO: 24), N-Ac-FHLRA-HAVDINGNQV-NH$_2$ (SEQ ID NO: 25), N-Ac-LYSHAVSSNG-NH$_2$ (SEQ ID NO: 18), N-Ac-LFSHAVSSNG-NH$_2$ (SEQ ID NO: 19), N-Ac-LFGHAVSENG-NH$_2$ (SEQ ID NO: 20), N-Ac-GHAVSE-NH$_2$ (SEQ ID NO: 26), N-Ac-AHAVSE-NH$_2$ (SEQ ID NO: 27), N-Ac-AHAVDI-NH$_2$ (SEQ ID NO: 28), N-Ac-SHAVSS-NH$_2$ (SEQ ID NO: 29) and compounds comprising such sequences or derivatives thereof.

Within certain other preferred embodiments, as discussed below, relatively small modulating agents that do not contain significant sequences flanking the HAV sequence (e.g., AHAVSE-NH$_2$; SEQ ID NO: 27) are preferred for modulating N-cadherin and E-cadherin mediated cell adhesion. Such modulating agents can be thought of as "master keys" that fit into peptide binding sites of each of the different classical cadherins, and are capable of disrupting cell adhesion of neural cells, endothelial cells, epithelial cells and/or certain cancer cells. Such modulating agents may generally by used to specifically modulate cell adhesion of neural or other cell types by topical administration or by linking a suitable targeting agent to the peptide, as discussed below. Such peptides may, but need not, contain an N-acetyl group and/or a C-amide group (e.g., N-Ac-AHAVSE-$NH_2$; SEQ ID NO: 27).

Peptide modulating agents (and peptide portions of modulating agents) as described herein may be synthesized by methods well known in the art, including chemical synthesis and recombinant DNA methods. For modulating agents up to about 50 residues in length, chemical synthesis may be performed using solid phase peptide synthesis techniques, in which a peptide linkage occurs through the direct condensation of the α-amino group of one amino acid with the α-carboxy group of the other amino acid with the elimination of a water molecule. Peptide bond synthesis by direct condensation, as formulated above, requires suppression of the reactive character of the amino group of the first and of the carboxyl group of the second amino acid. The masking substituents must permit their ready removal, without inducing breakdown of the labile peptide molecule.

Solid phase peptide synthesis uses an insoluble polymer for support during organic synthesis. The polymer-supported peptide chain permits the use of simple washing and filtration steps instead of laborious purifications at intermediate steps. Solid-phase peptide synthesis may generally be performed according to the method of Merrifield et al., *J. Am. Chem. Soc.* 85:2149, 1963, which involves assembling a linear peptide chain on a resin support using protected amino acids. Solid phase peptide synthesis typically utilizes either the Boc or Fmoc strategy. The Boc strategy uses a 1% cross-linked polystyrene resin. The standard protecting group for α-amino functions is the tert-butyloxycarbonyl (Boc) group. This group can be removed with dilute solutions of strong acids such as 25% trifluoroacetic acid (TFA). The next Boc-amino acid is typically coupled to the amino acyl resin using dicyclohexylcarbodiimide (DCC). Following completion of the assembly, the peptide-resin is treated with anhydrous HF to cleave the benzyl ester link and liberate the free peptide. Side-chain functional groups are usually blocked during synthesis by benzyl-derived blocking groups, which are also cleaved by HF. The free peptide is then extracted from the resin with a suitable solvent, purified and characterized. Newly synthesized peptides can be purified, for example, by gel filtration, HPLC, partition chromatography and/or ion-exchange chromatography, and may be characterized by, for example, mass spectrometry or amino acid sequence analysis. In the Boc strategy, C-terminal amidated peptides can be obtained using benzhydrylamine or methylbenzhydrylamine resins, which yield peptide amides directly upon cleavage with HF.

In the procedures discussed above, the selectivity of the side-chain blocking groups and of the peptide-resin link depends upon the differences in the rate of acidolytic cleavage. Orthoganol systems have been introduced in which the side-chain blocking groups and the peptide-resin link are completely stable to the reagent used to remove the α-protecting group at each step of the synthesis. The most common of these methods involves the 9-fluorenylmethyloxycarbonyl (Fmoc) approach. Within this method, the side-chain protecting groups and the peptide-resin link are completely stable to the secondary amines used for cleaving the N-α-Fmoc group. The side-chain protection and the peptide-resin link are cleaved by mild acidolysis. The repeated contact with base makes the Merrifield resin unsuitable for Fmoc chemistry, and p-alkoxybenzyl esters linked to the resin are generally used. Deprotection and cleavage are generally accomplished using TFA.

Those of ordinary skill in the art will recognize that, in solid phase synthesis, deprotection and coupling reactions must go to completion and the side-chain blocking groups must be stable throughout the entire synthesis. In addition, solid phase synthesis is generally most suitable when peptides are to be made on a small scale.

N-acetylation of the N-terminal residue can be accomplished by reacting the final peptide with acetic anhydride before cleavage from the resin. C-amidation may be accomplished using an appropriate resin such as methylbenzhydrylamine resin using the Boc technology.

For longer modulating agents, recombinant methods are preferred for synthesis. Within such methods, all or part of a modulating agent can be synthesized in living cells, using any of a variety of expression vectors known to those of ordinary skill in the art to be appropriate for the particular host cell. Suitable host cells may include bacteria, yeast cells, mammalian cells, insect cells, plant cells, algae and other animal cells (e.g., hybridoma, CHO, myeloma). The DNA sequences expressed in this manner may encode portions of an endogenous cadherin or other adhesion molecule. Such sequences may be prepared based on known cDNA or genomic sequences (see Blaschuk et al., *J. Mol. Biol.* 211:679-682, 1990), or from sequences isolated by screening an appropriate library with probes designed based on the sequences of known cadherins. Such screens may generally be performed as described in Sambrook et al., *Molecular Cloning: A Laboratory Manual*, Cold Spring Harbor Laboratories, Cold Spring Harbor, N.Y., 1989 (and references cited therein). Polymerase chain reaction (PCR) may also be employed, using oligonucleotide primers in methods well known in the art, to isolate nucleic acid molecules encoding all or a portion of an endogenous adhesion molecule. To generate a nucleic acid molecule encoding a desired modulating agent, an endogenous cadherin sequence may be modified using well known techniques. For example, portions encoding one or more CAR sequences may be joined, with or without separation by nucleic acid regions encoding linkers, as discussed above. Alternatively, portions of the desired nucleic acid sequences may be synthesized using well known techniques, and then ligated together to form a sequence encoding the modulating agent.

As noted above, instead of (or in addition to) an HAV sequence, a modulating agent may comprise an antibody, or antigen-binding fragment thereof, that specifically binds to a cadherin CAR sequence. As used herein, an antibody, or antigen-binding fragment thereof, is said to "specifically bind" to a cadherin CAR sequence (with or without flanking amino acids) if it reacts at a detectable level (within, for example, an ELISA, as described by Newton et al., *Develop. Dynamics* 197:1-13, 1993) with a peptide containing that sequence, and does not react detectably with peptides containing a different CAR sequence or a sequence in which the order of amino acid residues in the cadherin CAR sequence and/or flanking sequence is altered.

Within certain aspects of the present invention, modulating agents comprising polyclonal or monoclonal antibodies may be used to enhance and/or direct neurite outgrowth. Modulating agents comprising antibodies or antigen-binding fragments thereof (e.g., Fab fragments) may also be used, within other aspects, to inhibit cell adhesion in a variety of contexts. For example, such modulating agents may be used for treatment of demyelinating diseases, such as MS, or to inhibit interactions between tumor cells. Within further aspects, modulating agents comprising antibodies or antigen-binding fragments thereof that are linked to one or more linkers, or to a single molecule or support material may be used to enhance cell adhesion.

Polyclonal and monoclonal antibodies may be raised against a cadherin CAR sequence using conventional techniques. See, e.g., Harlow and Lane, *Antibodies: A Laboratory Manual*, Cold Spring Harbor Laboratory, 1988. In one such technique, an immunogen comprising the cadherin CAR sequence is initially injected into any of a wide variety of mammals (e.g., mice, rats, rabbits, sheep or goats). The smaller immunogens (i.e., less than about 20 amino acids) should be joined to a carrier protein, such as bovine serum albumin or keyhole limpet hemocyanin. Following one or more injections, the animals are bled periodically. Polyclonal antibodies specific for the CAR sequence may then be purified from such antisera by, for example, affinity chromatography using the modulating agent or antigenic portion thereof coupled to a suitable solid support.

Monoclonal antibodies specific for the cadherin CAR sequence may be prepared, for example, using the technique of Kohler and Milstein, *Eur. J. Immunol.* 6:511-519, 1976, and improvements thereto. Briefly, these methods involve the preparation of immortal cell lines capable of producing antibodies having the desired specificity from spleen cells obtained from an animal immunized as described above. The spleen cells are immortalized by, for example, fusion with a myeloma cell fusion partner, preferably one that is syngeneic with the immunized animal. Single colonies are selected and their culture supernatants tested for binding activity against the modulating agent or antigenic portion thereof. Hybridomas having high reactivity and specificity are preferred.

Monoclonal antibodies may be isolated from the supernatants of growing hybridoma colonies, with or without the use of various techniques known in the art to enhance the yield. Contaminants may be removed from the antibodies by conventional techniques, such as chromatography, gel filtration, precipitation, and extraction. Antibodies having the desired activity may generally be identified using immunofluorescence analyses of tissue sections, cell or other samples where the target cadherin is localized.

Within preferred embodiments, such monoclonal antibodies are specific for particular cadherins (e.g., the antibodies bind to E-cadherin, but do not bind significantly to N-cadherin, or vice versa). Such antibodies may be prepared as described above, using an immunogen that comprises (in addition to the HAV sequence) sufficient flanking sequence to generate the desired specificity (e.g., 6 amino acids on each side is generally sufficient). One representative immunogen is the 15-mer FHLRAHAVDINGNQV-$NH_2$ (SEQ ID NO: 25), linked to KLH (see Newton et al., *Dev. Dynamics* 197:1-13, 1993). To evaluate the specificity of a particular antibody, representative assays as described herein and/or conventional antigen-binding assays may be employed. Such antibodies may generally be used for therapeutic, diagnostic and assay purposes, as described herein. For example, such antibodies may be linked to a drug and administered to a mammal to target the drug to a particular cadherin-expressing cell, such as a leukemic cell in the blood.

Within certain embodiments, the use of antigen-binding fragments of antibodies may be preferred. Such fragments include Fab fragments, which may be prepared using standard techniques. Briefly, immunoglobulins may be purified from rabbit serum by affinity chromatography on Protein A bead columns (Harlow and Lane, *Antibodies: A Laboratory Manual*, Cold Spring Harbor Laboratory, 1988; see especially page 309) and digested by papain to yield Fab and Fc fragments. The Fab and Fc fragments may be separated by affinity chromatography on protein A bead columns (Harlow and Lane, 1988, pages 628-29).

Evaluation of Modulating Agent Activity

As noted above, modulating agents as described herein are capable of enhancing or inhibiting cadherin-mediated cell adhesion. The ability of an agent to modulate cell adhesion may generally be evaluated in vitro by assaying the effect on one or more of the following: (1) Schwann cell-astrocyte adhesion, (2) Schwann cell migration on astrocyte monolayers, (3) neurite outgrowth, (4) adhesion between endothelial cells, (5) adhesion between epithelial cells (e.g., normal rat kidney cells and/or human skin) and/or (6) adhesion between cancer cells. In general, a modulating agent is an inhibitor of cell adhesion if, within one or more of these representative assays, contact of the test cells with the modulating agent results in a discernible disruption of cell adhesion. Modulating agents that enhance cell adhesion (e.g., agents comprising multiple HAV sequences and/or linked to a support material) are considered to be modulators of cell adhesion if they are capable of enhancing neurite outgrowth as described below or are capable of promoting cell adhesion, as judged by plating assays to assess epithelial cell adhesion to a modulating agent attached to a support material, such as tissue culture plastic.

The effect of a modulating agent on Schwann cell adhesion to astrocytes may generally be evaluated using a cell adhesion assay. Briefly, Schwann cells fluorescently labeled with Di-I may be plated onto an astrocytic surface (e.g., a glass coverslip coated with a monolayer of astrocytes) and incubated on a shaking platform (e.g., 25 rpm for 30 minutes) in the presence and absence of modulating agent (e.g., LRAHAVDING (SEQ ID NO: 21) at a concentration of 1 mg/mL). Cells may then be washed (e.g., in Hanks medium) to remove non-attached cells. The attached cells may then be fixed and counted (e.g., using a fluorescent microscope). In general, 1 mg/mL of a modulating agent results in an increase or decrease in cell adhesion of at least 50%. This assay evaluates the effect of a modulating agent on N-cadherin mediated cell adhesion.

Schwann cell migration may generally be evaluated using a micro-inverted-coverslip assay. In this assay, a dense Schwann cell culture is established on coverslip fragments and Schwann cell migration away from the fragment edge is measured. Briefly, Schwann cells fluorescently labeled with Di-I may be plated on polylysine- and laminin-coated fragments of a glass coverslip and allowed to bind to the surface for 16-18 hours. Cells may then be washed (e.g., in Hanks medium) to remove non-attached cells, and then inverted, with cells facing downward onto an astrocyte-coated surface. Cultures are then incubated further for 2 days in the presence or absence of modulating agent (e.g., LRAHAVDING (SEQ ID NO: 21) at a concentration of 1 mg/mL) and fixed. The maximum migration distance from the edge of the coverslip fragment may then be measured. At a level of 1 mg/mL, modulating agent results in an increase or decrease in the maximum migration distance of at least 50%. This assay evaluates the effect of a modulating agent on N-cadherin mediated cell adhesion.

Within a representative neurite outgrowth assay, neurons may be cultured on a monolayer of cells (e.g., 3T3) that express N-cadherin. Neurons grown on such cells (under suitable conditions and for a sufficient period of time) extend longer neurites than neurons cultured on cells that do not express N-cadherin. For example, neurons may be cultured on monolayers of 3T3 cells transfected with cDNA encoding N-cadherin essentially as described by Doherty and Walsh, *Curr. Op. Neurobiol.* 4:49-55,1994; Williams et al., Neuron 13:583-594,1994; Hall et al., *Cell Adhesion and Commun.* 3:441-450, 1996; Doherty and Walsh, *Mol. Cell. Neurosci.* 8:99-111,1994; and Safell et al., *Neuron* 18:231-242, 1997. Briefly, monolayers of control 3T3 fibroblasts and 3T3 fibroblasts that express N-cadherin may be established by overnight culture of 80,000 cells in individual wells of an 8-chamber well tissue culture slide. 3000 cerebellar neurons isolated from post-natal day 3 mouse brains may be cultured for 18 hours on the various monolayers in control media (SATO/2% FCS), or media supplemented with various concentrations of the modulating agent or control peptide. The cultures may then be fixed and stained for GAP43 which specifically binds to the neurons and their neurites. The length of the longest neurite on each GAP43 positive neuron may be measured by computer assisted morphometry.

A modulating agent that modulates N-cadherin-mediated cell adhesion may inhibit or enhance such neurite outgrowth. Under the conditions described above, the presence of 500 µg/mL of a modulating agent that disrupts neural cell adhesion should result in a decrease in the mean neurite length by at least 50%, relative to the length in the absence of modulating agent or in the presence of a negative control peptide. Alternatively, the presence of 500 µg/mL of a modulating agent that enhances neural cell adhesion should result in an increase in the mean neurite length by at least 50%.

Within certain cell adhesion assays, the addition of a modulating agent to cells that express a cadherin results in disruption of cell adhesion. A "cadherin-expressing cell," as used herein, may be any type of cell that expresses at least one cadherin on the cell surface at a detectable level, using standard techniques such as immunocytochemical protocols (e.g., Blaschuk and Farookhi, *Dev. Biol.* 136:564-567, 1989). Cadherin-expressing cells include endothelial, epithelial and/or cancer cells. For example, such cells may be plated under standard conditions that, in the absence of modulating agent, permit cell adhesion. In the presence of modulating agent (e.g., 500 µg/mL), disruption of cell adhesion may be determined visually within 24 hours, by observing retraction of the cells from one another.

For use within one such assay, bovine pulmonary artery endothelial cells may be harvested by sterile ablation and digestion in 0.1% collagenase (type II; Worthington Enzymes, Freehold, N.J.). Cells may be maintained in Dulbecco's minimum essential medium supplemented with 10% fetal calf serum and 1% antibiotic-antimycotic at 37° C. in 7% $CO_2$ in air. Cultures may be passaged weekly in trypsin-EDTA and seeded onto tissue culture plastic at 20,000 cells/cm².

Endothelial cultures may be used at 1 week in culture, which is approximately 3 days after culture confluency is established. The cells may be seeded onto coverslips and treated (e.g., for 30 minutes) with modulating agent or a control compound at, for example, 500 µg/ml and then fixed with 1% paraformaldehyde.

As noted above, disruption of cell adhesion may be determined visually within 24 hours, by observing retraction of the cells from one another. This assay evaluates the effect of a modulating agent on N-cadherin mediated cell adhesion.

Within another such assay, the effect of a modulating agent on normal rat kidney (NRK) cells may be evaluated. According to a representative procedure, NRK cells (ATCC #1571-CRL) may be plated at 10-20,000 cells per 35 mm tissue culture flasks containing DMEM with 10% FCS and sub-cultured periodically (Laird et al., *J. Cell Biol.* 131: 1193-1203,1995). Cells may be harvested and replated in 35 mm tissue culture flasks containing 1 mm coverslips and incubated until 50-65% confluent (24-36 hours). At this time, coverslips may be transferred to a 24-well plate, washed once with fresh DMEM and exposed to modulating agent at a concentration of, for example, 1 mg/mL for 24 hours. Fresh modulating agent may then be added, and the cells left for an additional 24 hours. Cells may be fixed with 100% methanol for 10 minutes and then washed three times with PBS. Coverslips may be blocked for 1 hour in 2% BSA/PBS and incubated for a further 1 hour in the presence of mouse anti-E-cadherin antibody (Transduction Labs, 1:250 dilution). Primary and secondary antibodies may be diluted in 2% BSA/PBS. Following incubation in the primary antibody, coverslips may be washed three times for 5 minutes each in PBS and incubated for 1 hour with donkey anti-mouse antibody conjugated to fluorescein (diluted 1:200). Following further washes in PBS (3×5 min) coverslips can be mounted and viewed by confocal microscopy.

In the absence of modulating agent, NRK cells form characteristic tightly adherent monolayers with a cobblestone morphology in which cells display a polygonal shape. NRK cells that are treated with a modulating agent that disrupts E-cadherin mediated cell adhesion may assume a non-polygonal and elongated morphology (i.e., a fibroblast-like shape) within 48 hours of treatment with 1 mg/mL of modulating agent. Gaps appear in confluent cultures of such cells. In addition, 1 mg/mL of such a modulating agent reproducibly induces a readily apparent reduction in cell surface staining of E-cadherin, as judged by immunofluorescence microscopy (Laird et al., *J. Cell Biol.* 131:1193-1203, 1995), of at least 75% within 48 hours.

A third cell adhesion assay involves evaluating the effect of a modulating agent on permeability of adherent epithelial and/or endothelial cell layers. For example, the effect of permeability on human skin may be evaluated. Such skin may be derived from a natural source or may be synthetic. Human abdominal skin for use in such assays may generally be obtained from humans at autopsy within 24 hours of death. Briefly, a modulating agent (e.g., 500 µg/ml) and a test marker (e.g., the fluorescent markers Oregon Green™ and Rhodamine Green™ Dextran) may be dissolved in a sterile buffer (e.g., phosphate buffer, pH 7.2), and the ability of the marker to penetrate through the skin and into a receptor fluid (e.g., phosphate buffer) may be measured using a Franz Cell apparatus (Franz, *Curr. Prob. Dermatol.* 7:58-68, 1978; Franz, *J. Invest. Dermatol.* 64:190-195, 1975). The penetration of the markers through the skin may be assessed at, for example, 6, 12, 24, 36, and 48 hours after the start of the experiment. In general, a modulating agent that enhances the permeability of human skin results in a statistically significant increase in the amount of marker in the receptor compartment after 6-48 hours in the presence of 500 µg/mL modulating agent. This assay evaluates the effect of a modulating agent on E-cadherin mediated cell adhesion.

Modulating Agent Modification and Formulations

A modulating agent as described herein may, but need not, be linked to one or more additional molecules. In particular, as discussed below, it may be beneficial for certain applications to link multiple modulating agents (which may, but need not, be identical) to a support material, such as a single molecule (e.g., keyhole limpet hemocyanin) or a solid support, such as a polymeric matrix (which may be formulated as a membrane or microstructure, such as an ultra thin film), a container surface (e.g., the surface of a tissue culture plate or the interior surface of a bioreactor), or a bead or other particle, which may be prepared from a variety of materials including glass, plastic or ceramics. For certain applications, biodegradable support materials are preferred, such as cellulose and derivatives thereof, collagen, spider silk or any of a variety of polyesters (e.g., those derived from hydroxy acids and/or lactones) or sutures (see U.S. Pat. No. 5,245,012). Within certain embodiments, modulating agents and molecules comprising other CAR sequence(s) (e.g., an RGD sequence) may be attached to a support such as a polymeric matrix, preferably in an alternating pattern.

Suitable methods for linking a modulating agent to a support material will depend upon the composition of the support and the intended use, and will be readily apparent to those of ordinary skill in the art. Attachment may generally be achieved through noncovalent association, such as adsorption or affinity or, preferably, via covalent attachment (which may be a direct linkage between a modulating agent and functional groups on the support, or may be a linkage by way of a cross-linking agent). Attachment of a modulating agent by adsorption may be achieved by contact, in a suitable buffer, with a solid support for a suitable amount of time. The contact time varies with temperature, but is generally between about 5 seconds and 1 day, and typically between about 10 seconds and 1 hour.

Covalent attachment of a modulating agent to a molecule or solid support may generally be achieved by first reacting the support material with a bifunctional reagent that will also react with a functional group, such as a hydroxyl, thiol, carboxyl, ketone or amino group, on the modulating agent. For example, a modulating agent may be bound to an appropriate polymeric support or coating using benzoquinone, by condensation of an aldehyde group on the support with an amine and an active hydrogen on the modulating agent or by condensation of an amino group on the support with a carboxylic acid on the modulating agent. A preferred method of generating a linkage is via amino groups using glutaraldehyde. A modulating agent may be linked to cellulose via ester linkages. Similarly, amide linkages may be suitable for linkage to other molecules such as keyhole limpet hemocyanin or other support materials. Multiple modulating agents and/or molecules comprising other CAR sequences may be attached, for example, by random coupling, in which equimolar amounts of such molecules are mixed with a matrix support and allowed to couple at random.

Although modulating agents as described herein may preferentially bind to specific tissues or cells, and thus may be sufficient to target a desired site in vivo, it may be beneficial for certain applications to include an additional targeting agent. Accordingly, a targeting agent may also, or alternatively, be linked to a modulating agent to facilitate targeting to one or more specific tissues. As used herein, a "targeting agent," may be any substance (such as a compound or cell) that, when linked to a modulating agent enhances the transport of the modulating agent to a target tissue, thereby increasing the local concentration of the modulating agent. Targeting agents include antibodies or fragments thereof, receptors, ligands and other molecules that bind to cells of, or in the vicinity of, the target tissue. Known targeting agents include serum hormones, antibodies against cell surface antigens, lectins, adhesion molecules, tumor cell surface binding ligands, steroids, cholesterol, lymphokines, fibrinolytic enzymes and those drugs and proteins that bind to a desired target site. Among the many monoclonal antibodies that may serve as targeting agents are anti-TAC, or other interleukin-2 receptor antibodies; 9.2.27 and NR-ML-05, reactive with the 250 kilodalton human melanoma-associated proteoglycan; and NR-LU-10, reactive with a pancarcinoma glycoprotein. An antibody targeting agent may be an intact (whole) molecule, a fragment thereof, or a functional equivalent thereof. Examples of antibody fragments are F(ab')2, -Fab', Fab and F[v] fragments, which may be produced by conventional methods or by genetic or protein engineering. Linkage is generally covalent and may be achieved by, for example, direct condensation or other reactions, or by way of bi- or multifunctional linkers. Within other embodiments, it may also be possible to target a polynucleotide encoding a modulating agent to a target tissue, thereby increasing the local concentration of modulating agent. Such targeting may be achieved using well known techniques, including retroviral and adenoviral infection.

For certain embodiments, it may be beneficial to also, or alternatively, link a drug to a modulating agent. As used herein, the term "drug" refers to any bioactive agent intended for administration to a mammal to prevent or treat a disease or other undesirable condition. Drugs include hormones, growth factors, proteins, peptides and other compounds. The use of certain specific drugs within the context of the present invention is discussed below.

Modulating agents as described herein may be present within a pharmaceutical composition. A pharmaceutical composition comprises one or more modulating agents in combination with one or more pharmaceutically or physiologically acceptable carriers, diluents or excipients. Such compositions may comprise buffers (e.g., neutral buffered saline or phosphate buffered saline), carbohydrates (e.g., glucose, mannose, sucrose or dextrans), mannitol, proteins, polypeptides or amino acids such as glycine, antioxidants, chelating agents such as EDTA or glutathione, adjuvants (e.g., aluminum hydroxide) and/or preservatives. Within yet other embodiments, compositions of the present invention may be formulated as a lyophilizate. One or more modulating agents (alone or in combination with a targeting agent and/or drug) may, but need not, be encapsulated within liposomes using well known technology. Compositions of the present invention may be formulated for any appropriate manner of administration, including for example, topical, oral, nasal, intravenous, intracranial, intraperitoneal, subcutaneous, or intramuscular administration.

For certain embodiments, as discussed below, a pharmaceutical composition may further comprise a modulator of cell adhesion that is mediated by one or more molecules other than cadherins. Such modulators may generally be prepared as described above, incorporating one or more non-cadherin CAR sequences and/or antibodies thereto in place of the cadherin CAR sequences and antibodies. Such compositions are particularly useful for situations in which it is desirable to inhibit cell adhesion mediated by multiple cell-adhesion molecules, such as other members of the cadherin gene superfamily that are not classical cadherins (e.g., Dsg and Dsc); integrins; members of the immunoglobulin supergene family, such as N-CAM; and other uncategorized transmembrane proteins, such as occludin, as well as extracellular matrix proteins such as laminin, fibronectin, collagens, vitronectin, entactin and tenascin. Preferred CAR sequences for use within such a modulator include RGD, YIGSR (SEQ ID NO: 12), KYSFNYDGSE (SEQ ID NO: 13), IWKHKGRDVILKKDVRF (SEQ ID NO: 14), YAT, FAT, YAS, RAL and/or GVNPTAQSSGSLYGSQIYALCN-QFYTP AATGLYVDQYLYHYCVVDPQE (SEQ ID NO: 31), or derivatives thereof such as QSSGSLYGSQ (SEQ ID NO: 16) and QYLYHYCVVD (SEQ ID NO: 17).

A pharmaceutical composition may also, or alternatively, contain one or more drugs, which may be linked to a modulating agent or may be free within the composition. Virtually any drug may be administered in combination with a modulating agent as described herein, for a variety of purposes as described below. Examples of types of drugs that may be administered with a modulating agent include analgesics, anesthetics, antianginals, antifungals, antibiotics, anticancer drugs (e.g., taxol or mitomycin C), antiinflammatories (e.g., ibuprofen and indomethacin), anthelmintics, antidepressants, antidotes, antiemetics, antihistamines, antihypertensives, antimalarials, antimicrotubule agents (e.g., colchicine or vinca alkaloids), antimigraine agents, antimicrobials, antiphsycotics, antipyretics, antiseptics, anti-signaling agents (e.g., protein kinase C inhibitors or inhibitors of intracellular calcium mobilization), antiarthritics, antithrombin agents, antituberculotics, antitussives, antivirals, appetite suppressants, cardioactive drugs, chemical dependency drugs, cathartics, chemotherapeutic agents, coronary, cerebral or peripheral vasodilators, contraceptive agents, depressants, diuretics, expectorants, growth factors, hormonal agents, hypnotics, immunosuppression agents, narcotic antagonists, parasympathomimetics, sedatives, stimulants, sympathomimetics, toxins (e.g., cholera toxin), tranquilizers and urinary antiinfectives.

For imaging purposes, any of a variety of diagnostic agents may be incorporated into a pharmaceutical composition, either linked to a modulating agent or free within the composition. Diagnostic agents include any substance administered to illuminate a physiological function within a patient, while leaving other physiological functions generally unaffected. Diagnostic agents include metals, radioactive isotopes and radioopaque agents (e.g., gallium, technetium, indium, strontium, iodine, barium, bromine and phosphorus-containing compounds), radiolucent agents, contrast agents, dyes (e.g., fluorescent dyes and chromophores) and enzymes that catalyze a colorimetric or fluorometric reaction. In general, such agents may be attached using a variety of techniques as described above, and may be present in any orientation.

The compositions described herein may be administered as part of a sustained release formulation (i.e., a formulation such as a capsule or sponge that effects a slow release of modulating agent following administration). Such formulations may generally be prepared using well known technology and administered by, for example, oral, rectal or subcutaneous implantation, or by implantation at the desired target site. Sustained-release formulations may contain a modulating agent dispersed in a carrier matrix and/or contained within a reservoir surrounded by a rate controlling membrane (see, e.g., European Patent Application 710,491 A). Carriers for use within such formulations are biocompatible, and may also be biodegradable; preferably the formulation provides a relatively constant level of modulating agent release. The amount of modulating agent contained within a sustained release formulation depends upon the site of implantation, the rate and expected duration of release and the nature of the condition to be treated or prevented.

Pharmaceutical compositions of the present invention may be administered in a manner appropriate to the disease to be treated (or prevented). Appropriate dosages and a suitable duration and frequency of administration will be determined by such factors as the condition of the patient, the type and severity of the patient's disease and the method of administration. In general, an appropriate dosage and treatment regimen provides the modulating agent(s) in an amount sufficient to provide therapeutic and/or prophylactic benefit. Within particularly preferred embodiments of the invention, a modulating agent or pharmaceutical composition as described herein may be administered at a dosage ranging from 0.001 to 50 mg/kg body weight, preferably from 0.1 to 20 mg/kg, on a regimen of single or multiple daily doses. For topical administration, a cream typically comprises an amount of modulating agent ranging from 0.00001% to 1%, preferably 0.0001% to 0.002%. Fluid compositions typically contain an amount of modulating agent ranging from 10 ng/ml to 5 mg/ml, preferably from 10 µg to 2 mg/mL. Appropriate dosages may generally be determined using experimental models and/or clinical trials. In general, the use of the minimum dosage that is sufficient to provide effective therapy is preferred. Patients may generally be monitored for therapeutic effectiveness using assays suitable for the condition being treated or prevented, which will be familiar to those of ordinary skill in the art.

Modulating Agent Methods of Use

In general, the modulating agents and compositions described herein may be used for modulating the adhesion of cadherin-expressing cells (i.e., cells that express one or more of E-cadherin, N-cadherin, P-cadherin, R-cadherin and/or other cadherin(s) containing the HAV sequence, including as yet undiscovered cadherins) in vitro and/or in vivo. As noted above, modulating agents for purposes that involve the disruption of cadherin-mediated cell adhesion may comprise an HAV sequence, multiple HAV sequences in close proximity and/or an antibody (or an antigen-binding fragment thereof) that recognizes a cadherin CAR sequence. When it is desirable to also disrupt cell adhesion mediated by other adhesion molecules, a modulating agent may additionally comprise one or more CAR sequences bound by such adhesion molecules (and/or antibodies or fragments thereof that bind such sequences), preferably separated from each other and from the HAV sequence by linkers. As noted above, such linkers may or may not comprise one or more amino acids. For enhancing cell adhesion, a modulating agent may contain multiple HAV sequences or antibodies (or fragments), preferably separated by linkers, and/or may be linked to a single molecule or to a support material as described above.

Certain methods involving the disruption of cell adhesion as described herein have an advantage over prior techniques in that they permit the passage of molecules that are large and/or charged across barriers of cadherin-expressing cells. As described in greater detail below, modulating agents as described herein may also be used to disrupt or enhance cell adhesion in a variety of other contexts. Within each of the methods described herein, one or more modulating agents may generally be administered alone, or within a pharmaceutical composition. In each specific method described herein, as noted above, a targeting agent may be employed to increase the local concentration of modulating agent at the target site.

Within one aspect, one or more modulating agents may be used for therapy of a demyelinating neurological disease in a mammal. There are a number of demyelinating diseases, such as multiple sclerosis, characterized by oligodendrocyte death. It has been found, within the context of the present invention, that Schwann cell migration on astrocytes is inhibited by N-cadherin. Modulating agents that disrupt N-cadherin mediated cell adhesion as described herein, when implanted with Schwann cells into the central nervous system, may facilitate Schwann cell migration and permit the practice of Schwann cell replacement therapy.

Multiple sclerosis patients suitable for treatment may be identified by criteria that establish a diagnosis of clinically definite or clinically probable MS (see Poser et al., *Ann. Neurol.* 13:227, 1983). Candidate patients for preventive therapy may be identified by the presence of genetic factors, such as HLA-type DR2a and DR2b, or by the presence of early disease of the relapsing remitting type.

Schwann cell grafts may be implanted directly into the brain along with the modulating agent(s) using standard techniques. Preferred peptide modulating agents for use within such methods include LRAHAVDING-NH$_2$ (SEQ ID NO: 21), LRAHAVDVNG-NH$_2$ (SEQ ID NO: 22), MRAHAVDING-NH$_2$ (SEQ ID NO: 23), HLGAHAVDINGN-QVET-NH$_2$ (SEQ ID NO: 24), FHLRAHAVDINGNQV-NH$_2$ (SEQ ID NO: 25), AHAVSE-NH$_2$ (SEQ ID NO: 27), AHAVDI-NH$_2$ (SEQ ID NO: 28), N-Ac-LRAHAVDING-NH$_2$ (SEQ ID NO: 21), N-Ac-LRAHAVDVNG-NH$_2$ (SEQ ID NO: 22), N-Ac-MRAHAVDING-NH$_2$ (SEQ ID NO: 23), N-Ac-HLGAHAVDINGNQVET-NH$_2$ (SEQ ID NO: 24), N-Ac-FHLRAHAVDINGNQV-NH$_2$ (SEQ ID NO: 25), N-Ac-AHAVSE-NH$_2$ (SEQ ID NO: 27), N-Ac-AHAVDI-NH$_2$ (SEQ ID NO: 28), derivatives of such sequences and modulating agents comprising any one of these sequences or derivatives thereof. Preferred antibody modulating agents include Fab fragments directed against the N-cadherin CAR sequence FHLRAHAVDINGNQV-NH$_2$ (SEQ ID NO: 25). Such antibodies and fragments can be prepared using standard techniques, as discussed above. Suitable amounts of modulating agent generally range as described above, preferably from about 10 µg/mL to about 1 mg/mL.

Alternatively, a modulating agent may be implanted with oligodendrocyte progenitor cells (OPs) derived from donors not afflicted with the demyelinating disease. The myelinating cell of the CNS is the oligodendrocyte. Although mature oligodendrocytes and immature cells of the oligodendrocyte lineage, such as the oligodendrocyte type 2 astrocyte progenitor, have been used for transplantation, OPs are more widely used. OPs are highly motile and are able to migrate from transplant sites to lesioned areas where they differentiate into mature myelin-forming oligodendrocytes and contribute to repair of demyelinated axons (see e.g., Groves et al., *Nature* 362:453-55, 1993; Baron-Van Evercooren et al., *Glia* 16:147-64, 1996). OPs can be isolated using routine techniques known in the art (see e.g., Milner and French-Constant, *Development* 120:3497-3506, 1994), from many regions of the CNS including brain, cerebellum, spinal cord, optic nerve and olfactory bulb. Substantially greater yields of OP's are obtained from embryonic or neonatal rather than adult tissue. OPs may be isolated from human embryonic spinal cord and cultures of neurospheres established. Human fetal tissue is a potential valuable and renewable source of donor OP's for future, long range transplantation therapies of demyelinating diseases such as MS. OPs can be expanded in vitro if cultured as "homotypic aggregates" or "spheres" (Avellana-Adalid et al, *J. Neurosci. Res.* 45:558-70,1996). Spheres (sometimes called "oligospheres" or "neurospheres") are formed when OPs are grown in suspension in the presence of growth factors such as PDGF and FGF.

OPs can be harvested from spheres by mechanical dissociation and used for subsequent transplantation or establishment of new spheres in culture.

Alternatively, the spheres themselves may be transplanted, providing a "focal reservoir" of OPs (Avellana-Adalid et al, *J. Neurosci. Res.* 45:558-70, 1996).

An alternative source of OP may be spheres derived from CNS stem cells. Recently, Reynolds and Weiss, *Dev. Biol.* 165:1-13, 1996 have described spheres formed from EGF-responsive cells derived from embryonic neuroepithelium, which appear to retain the pluripotentiality exhibited by neuroepithelium in vivo. Cells dissociated from these spheres are able to differentiate into neurons, oligodendrocytes and astrocytes when plated on adhesive substrates in the absence of EGF, suggesting that EGF-responsive cells derived from undifferentiated embryonic neuroepithelium may represent CNS stem cells (Reynolds and Weiss, *Dev. Biol.* 165:1-13,1996). Spheres derived from CNS stem cells provide an alternative source of OP which may be manipulated in vitro for transplantation in vivo. Spheres composed of CNS stem cells may further provide a microenvironment conducive to increased survival, migration, and differentiation of the OPs in vivo.

The use of neurospheres for the treatment of MS may be facilitated by modulating agents that enhance cell migration from the spheres. In the absence of modulating agent, the cells within the spheres adhere tightly to one another and migration out of the spheres is hindered. Modulating agents that disrupt N-cadherin mediated cell adhesion as described herein, when injected with neurospheres into the central nervous system, may improve cell migration and increase the efficacy of OP replacement therapy.

Neurosphere grafts may be implanted directly into the central nervous system along with the modulating agent(s) using standard techniques. Preferred peptide modulating agents for use within such methods include LRAHAVDING-NH$_2$ (SEQ ID NO: 21), LRAHAVDVNG-NH$_2$ (SEQ ID NO: 22), MRAHAVDING-NH$_2$ (SEQ ID NO: 23), HLGAHAVDINGNQVET-NH$_2$ (SEQ ID NO: 24), FHLRAHAVDINGNQV-NH$_2$ (SEQ ID NO: 25), AHAVSE-NH$_2$ (SEQ ID NO: 27), AHAVDI-NH$_2$ (SEQ ID NO: 28), N-Ac-LRAHAVDING-NH$_2$ (SEQ ID NO: 21), N-Ac-LRAHAVDVNG-NH$_2$ (SEQ ID NO: 22), N-Ac-MRAHAVDING-NH$_2$ (SEQ ID NO: 23), N-Ac-HLGAHAVDINGNQVET-NH$_2$ (SEQ ID NO: 24), N-Ac-FHLRAHAVDINGNQV-NH$_2$ (SEQ ID NO: 25), N-Ac-AHAVSE-NH$_2$ (SEQ ID NO: 27), N-Ac-AHAVDI-NH$_2$ (SEQ ID NO: 28) and derivatives of such sequences. Modulating agents comprising one or more of these sequences or derivatives thereof are also preferred. Preferred antibody modulating agents include Fab fragments directed against the N-cadherin CAR sequence FHLRAHAVDINGNQV-NH$_2$ (SEQ ID NO: 25). Such antibodies and fragments can be prepared using standard techniques, as discussed above. Suitable amounts of modulating agent generally range as described above, preferably from about 10 µg/mL to about 1 mg/mL.

Alternatively, a modulating agent may be administered alone or within a pharmaceutical composition. The duration and frequency of administration will be determined by such factors as the condition of the patient, and the type and severity of the patient's disease. Within particularly preferred embodiments of the invention, the modulating agent or pharmaceutical composition may be administered at a dosage ranging from 0.1 mg/kg to 20 mg/kg although appropriate dosages may be determined by clinical trials. Methods of administration include injection, intravenous or intrathecal (i.e., directly in cerebrospinal fluid). A modulating agent or pharmaceutical composition may further comprise a drug (e.g., an immunomodulatory drug).

Effective treatment of multiple sclerosis may be evidenced by any of the following criteria: EDSS (extended disability status scale), appearance of exacerbations or MRI (magnetic resonance imaging). The EDSS is a means to grade clinical impairment due to MS (Kurtzke, *Neurology* 33:1444, 1983), and a decrease of one full step defines an effective treatment in the context of the present invention (Kurtzke, *Ann. Neurol.* 36:573-79, 1994). Exacerbations are defined as the appearance of a new symptom that is attributable to MS and accompanied by an appropriate new neurologic abnormality (Sipe et al., *Neurology* 34:1368, 1984). Therapy is deemed to be effective if there is a statistically significant difference in the rate or proportion of exacerbation-free patients between the treated group and the placebo group or a statistically significant difference in the time to first exacerbation or duration and severity in the treated group compared to control group. MRI can be used to measure active lesions using gadolinium-DTPA-enhanced imaging (McDonald et al. *Ann. Neurol.* 36:14,1994) or the location and extent of lesions using T$_2$-weighted techniques. The presence, location and extent of MS lesions may be determined by radiologists using standard techniques. Improvement due to therapy is established when there is a statistically significant improvement in an individual patient compared to baseline or in a treated group versus a placebo group.

Efficacy of the modulating agent in the context of prevention may be judged based on clinical measurements such as the relapse rate and EDSS. Other criteria include a change in area and volume of T2 images on MRI, and the number and volume of lesions determined by gadolinium enhanced images.

Within other aspects, methods are provided in which cell adhesion is diminished. In one such aspect, the present invention provides methods for reducing unwanted cellular adhesion by administering a modulating agent as described herein. Unwanted cellular adhesion can occur between tumor cells, between tumor cells and normal cells or between normal cells as a result of surgery, injury, chemotherapy, disease, inflammation or other condition jeopardizing cell viability or function. Preferred modulating agents for use within such methods include LRAHAVDING-NH$_2$ (SEQ ID NO: 21), LRAHAVDVNG-NH$_2$ (SEQ ID NO: 22), MRAHAVDING-NH$_2$ (SEQ ID NO: 23), HLGAHAVDINGNQVET-NH$_2$ (SEQ ID NO: 24), FHLRAHAVDINGNQV-NH$_2$ (SEQ ID NO: 25), LYSHAVSSNG-NH$_2$ (SEQ ID NO: 18), AHAVSE-NH$_2$ (SEQ ID NO: 27), AHAVDI-NH$_2$ (SEQ ID NO: 28), SHAVSS-NH$_2$ (SEQ ID NO: 29), LFSHAVSSNG-NH$_2$ (SEQ ID NO: 19), derivatives of such sequences (e.g., N-Ac-LRAHAVDING-NH$_2$ (SEQ ID NO: 21), N-Ac-LRAHAVDVNG-NH$_2$ (SEQ ID NO: 22), N-Ac-MRAHAVDING-NH$_2$ (SEQ ID NO: 23), N-Ac-HLGAHAVDINGNQVET-NH$_2$ (SEQ ID NO: 24), N-Ac-FHLRAHAVDINGNQV-NH$_2$ (SEQ ID NO: 25), N-Ac-LYSHAVSSNG-NH$_2$ (SEQ ID NO: 18), N-Ac-LFSHAVSSNG-NH$_2$ (SEQ ID NO: 19), N-Ac-AHAVSE-NH$_2$ (SEQ ID NO: 27), N-Ac-AHAVDI-NH$_2$ (SEQ ID NO: 28), N-Ac-SHAVSS-NH$_2$ (SEQ ID NO: 29)) and modulating agents comprising such sequences or derivatives thereof. Preferred antibody modulating agents include Fab fragments directed against either the N-cadherin CAR sequence FHLRAHAVDINGNQV-NH$_2$ (SEQ ID NO: 25) or E-cadherin CAR sequence LFSHAVSSNG-NH$_2$ (SEQ ID NO: 19). In addition, a modulating agent may comprise the sequence RGD, which is bound by integrins, separated from the HAV sequence via a linker. Alternatively, a separate modulator of integrin-mediated cell adhesion may be administered in conjunction with the modulating agent(s), either within the same pharmaceutical composition or separately. Topical administration of the modulating agent(s) is generally preferred, but other means may also be employed. Preferably, a fluid composition for topical administration (comprising, for example, physiological saline) comprises an amount of modulating agent as described above, and more preferably from 10 µg/mL to 1 mg/mL. Creams may generally be formulated as described above. Topical administration in the surgical field may be given once at the end of surgery by irrigation of the wound or as an intermittent or continuous irrigation with the use of surgical drains in the post-operative period or by the use of drains specifically inserted in an area of inflammation, injury or disease in cases where surgery does not need to be performed. Alternatively, parenteral or transcutaneous administration may be used to achieve similar results.

Within another such aspect, methods are provided for enhancing the delivery of a drug through the skin of a mammal. Transdermal delivery of drugs is a convenient and non-invasive method that can be used to maintain relatively constant blood levels of a drug. In general, to facilitate drug delivery via the skin, it is necessary to perturb adhesion between the epithelial cells (keratinocytes) and the endothelial cells of the microvasculature. Using currently available techniques, only small, uncharged molecules may be delivered across skin in vivo. The methods described herein are not subject to the same degree of limitation. Accordingly, a wide variety of drugs may be transported across the epithelial and endothelial cell layers of skin, for systemic or topical administration. Such drugs may be delivered to melanomas or may enter the blood stream of the mammal for delivery to other sites within the body.

To enhance the delivery of a drug through the skin, a modulating agent as described herein and a drug are contacted with the skin surface. Preferred modulating agents for use within such methods include LRAHAVDING-$NH_2$ (SEQ ID NO: 21), LRAHAVDVNG-$NH_2$ (SEQ ID NO: 22), MRAHAVDING-$NH_2$ (SEQ ID NO: 23), HLGA-HAVDINGNQVET-$NH_2$ (SEQ ID NO: 24), FHLRA-HAVDINGNQV-$NH_2$ (SEQ ID NO: 25), LYSHAVSSNG-$NH_2$ (SEQ ID NO: 18), AHAVSE-$NH_2$ (SEQ ID NO: 27), AHAVDI-$NH_2$ (SEQ ID NO: 28), SHAVSS-$NH_2$ (SEQ ID NO: 29), LFGHAVSENG-$NH_2$ (SEQ ID NO: 20), LFSHAVSSNG-$NH_2$ (SEQ ID NO: 19), GHAVSE-$NH_2$ (SEQ ID NO: 26), derivatives of such sequences (e.g., N-Ac-LRAHAVDING-$NH_2$ (SEQ ID NO: 21), N-Ac-LRA-HAVDVNG-$NH_2$ (SEQ ID NO: 22), N-Ac-MRA-HAVDING-$NH_2$ (SEQ ID NO: 23), N-Ac-HLGA-HAVDINGNQVET-$NH_2$ (SEQ ID NO: 24), N-Ac-FHLRAHAVDINGNQV-$NH_2$ (SEQ ID NO: 25), N-Ac-LYSHAVSSNG-$NH_2$ (SEQ ID NO: 18), N-Ac-LFSHAVSSNG-$NH_2$ (SEQ ID NO: 19), N-Ac-AHAVSE-$NH_2$ (SEQ ID NO: 27), N-Ac-AHAVDI-$NH_2$ (SEQ ID NO: 28), N-Ac-SHAVSS-$NH_2$ (SEQ ID NO: 29)) and modulating agents comprising such sequences or derivatives thereof. Preferred antibody modulating agents include Fab fragments directed against either the N-cadherin CAR sequence FHL-RAHAVDINGNQV-$NH_2$ (SEQ ID NO: 25), P-cadherin CAR sequence LFGHAVSENG-$NH_2$ (SEQ ID NO: 20) or E-cadherin CAR sequence LFSHAVSSNG-$NH_2$ (SEQ ID NO: 19). Multifunctional modulating agents comprising the cadherin CAR sequence HAV linked to one or more of the Dsc CAR sequences YAT, FAT and YAS and/or the Dsg CAR sequence RAL may also be used to disrupt epithelial cell adhesion. Alternatively, a separate modulator of non-classical cadherin-mediated cell adhesion may be administered in conjunction with the modulating agent(s), either within the same pharmaceutical composition or separately. Contact may be achieved by direct application of the modulating agent, generally within a composition formulated as a cream or gel, or using any of a variety of skin contact devices for transdermal application (such as those described in European Patent Application No. 566,816 A; U.S. Pat. No. 5,613,958; U.S. Pat. No. 5,505,956). A skin patch provides a convenient method of administration (particularly for slow-release formulations). Such patches may contain a reservoir of modulating agent and drug separated from the skin by a membrane through which the drug diffuses. Within other patch designs, the modulating agent and drug may be dissolved or suspended in a polymer or adhesive matrix that is then placed in direct contact with the patient's skin. The modulating agent and drug may then diffuse from the matrix into the skin. Modulating agent(s) and drug(s) may be contained within the same composition or skin patch, or may be separately administered, although administration at the same time and site is preferred. In general, the amount of modulating agent administered via the skin varies with the nature of the condition to be treated or prevented, but may vary as described above. Such levels may be achieved by appropriate adjustments to the device used, or by applying a cream formulated as described above. Transfer of the drug across the skin and to the target tissue may be predicted based on in vitro studies using, for example, a Franz cell apparatus, and evaluated in vivo by appropriate means that will be apparent to those of ordinary skill in the art. As an example, monitoring of the serum level of the administered drug over time provides an easy measure of the drug transfer across the skin.

Transdermal drug delivery as described herein is particularly useful in situations in which a constant rate of drug delivery is desired, to avoid fluctuating blood levels of a drug. For example, morphine is an analgesic commonly used immediately following surgery. When given intermittently in a parenteral form (intramuscular, intravenous), the patient usually feels sleepy during the first hour, is well during the next 2 hours and is in pain during the last hour because the blood level goes up quickly after the injection and goes down below the desirable level before the 4 hour interval prescribed for re-injection is reached. Transdermal administration as described herein permits the maintenance of constant levels for long periods of time (e.g., days), which allows adequate pain control and mental alertness at the same time. Insulin provides another such example. Many diabetic patients need to maintain a constant baseline level of insulin which is different from their needs at the time of meals. The baseline level may be maintained using transdermal administration of insulin, as described herein. Antibiotics may also be administered at a constant rate, maintaining adequate bactericidal blood levels, while avoiding the high levels that are often responsible for the toxicity (e.g., levels of gentamycin that are too high typically result in renal toxicity).

Drug delivery by the methods of the present invention also provide a more convenient method of drug administration. For example, it is often particularly difficult to administer parenteral drugs to newborns and infants because of the difficulty associated with finding veins of acceptable caliber to catheterize. However, newborns and infants often have a relatively large skin surface as compared to adults. Transdermal drug delivery permits easier management of such patients and allows certain types of care that can presently be given only in hospitals to be given at home. Other patients who typically have similar difficulties with venous catheterization are patients undergoing chemotherapy or patients on dialysis. In addition, for patients undergoing prolonged therapy, transdermal administration as described herein is more convenient than parenteral administration.

Transdermal administration as described herein also allows the gastrointestinal tract to be bypassed in situations where parenteral uses would not be practical. For example, there is a growing need for methods suitable for administration of therapeutic small peptides and proteins, which are typically digested within the gastrointestinal tract. The methods described herein permit administration of such compounds and allow easy administration over long periods of time. Patients who have problems with absorption through their gastrointestinal tract because of prolonged ileus or specific gastrointestinal diseases limiting drug absorption may also benefit from drugs formulated for transdermal application as described herein.

Further, there are many clinical situations where it is difficult to maintain compliance. For example, patients with mental problems (e.g., patients with Alzheimer's disease or psychosis) are easier to manage if a constant delivery rate of drug is provided without having to rely on their ability to take their medication at specific times of the day. Also patients who simply forget to take their drugs as prescribed are less likely to do so if they merely have to put on a skin patch periodically (e.g., every 3 days). Patients with diseases that are without symptoms, like patients with hypertension, are especially at risk of forgetting to take their medication as prescribed.

For patients taking multiple drugs, devices for transdermal application such as skin patches may be formulated with combinations of drugs that are frequently used together. For example, many heart failure patients are given digoxin in combination with furosemide. The combination of both drugs into a single skin patch facilitates administration, reduces the risk of errors (taking the correct pills at the appropriate time is often confusing to older people), reduces the psychological strain of taking "so many pills," reduces skipped dosage because of irregular activities and improves compliance.

The methods described herein are particularly applicable to humans, but also have a variety of veterinary uses, such as the administration of growth factors or hormones (e.g., for fertility control) to an animal.

As noted above, a wide variety of drugs may be administered according to the methods provided herein. Some examples of drug categories that may be administered transdermally include anti-inflammatory drugs (e.g., in arthritis and in other condition) such as all NSAID, indomethacin, prednisone, etc.; analgesics (especially when oral absorption is not possible, such as after surgery, and when parenteral administration is not convenient or desirable), including morphine, codeine, Demerol, acetaminophen and combinations of these (e.g., codeine plus acetaminophen); antibiotics such as Vancomycin (which is not absorbed by the GI tract and is frequently given intravenously) or a combination of INH and Rifampicin (e.g., for tuberculosis); anticoagulants such as heparin (which is not well absorbed by the GI tract and is generally given parenterally, resulting in fluctuation in the blood levels with an increased risk of bleeding at high levels and risks of inefficacy at lower levels) and Warfarin (which is absorbed by the GI tract but cannot be administered immediately after abdominal surgery because of the normal ileus following the procedure); antidepressants (e.g., in situations where compliance is an issue as in Alzheimer's disease or when maintaining stable blood levels results in a significant reduction of anti-cholinergic side effects and better tolerance by patients), such as amitriptylin, imipramin, prozac, etc.; antihypertensive drugs (e.g., to improve compliance and reduce side effects associated with fluctuating blood levels), such as diuretics and beta-blockers (which can be administered by the same patch; e.g., furosemide and propanolol); antipsychotics (e.g., to facilitate compliance and make it easier for care giver and family members to make sure that the drug is received), such as haloperidol and chlorpromazine; and anxiolytics or sedatives (e.g., to avoid the reduction of alertness related to high blood levels after oral administration and allow a continual benefit throughout the day by maintaining therapeutic levels constant).

Numerous other drugs may be administered as described herein, including naturally occurring and synthetic hormones, growth factors, proteins and peptides. For example, insulin and human growth hormone, growth factors like erythropoietin, interleukins and inteferons may be delivered via the skin.

Kits for administering a drug via the skin of a mammal are also provided within the present invention. Such kits generally comprise a device for transdermal application (e.g., a skin patch) in combination with, or impregnated with, one or more modulating agents. A drug may additionally be included within such kits.

Within a related aspect, the use of modulating agents as described herein to increase skin permeability may also facilitate sampling of the blood compartment by passive diffusion, permitting detection and/or measurement of the levels of specific molecules circulating in the blood. For example, application of one or more modulating agents to the skin, via a skin patch as described herein, permits the patch to function like a sponge to accumulate a small quantity of fluid containing a representative sample of the serum. The patch is then removed after a specified amount of time and analyzed by suitable techniques for the compound of interest (e.g., a medication, hormone, growth factor, metabolite or marker). Alternatively, a patch may be impregnated with reagents to permit a color change if a specific substance (e.g., an enzyme) is detected. Substances that can be detected in this manner include, but are not limited to, illegal drugs such as cocaine, HIV enzymes, glucose and PSA. This technology is of particular benefit for home testing kits.

Within a further aspect, methods are provided for enhancing delivery of a drug to a tumor in a mammal, comprising administering a modulating agent in combination with a drug to a tumor-bearing mammal. Modulating agents for use within such methods include those designed to disrupt E-cadherin and/or N-cadherin mediated cell adhesion, such as AHAVDI-NH$_2$ (SEQ ID NO: 28), which is specific for N-cadherin, SHAVSS-NH$_2$ (SEQ ID NO: 29) and LFSHAVSSNG-NH$_2$ (SEQ ID NO: 18), which are specific for E-cadherin, AHAVSE-NH$_2$ (SEQ ID NO: 27) and derivatives thereof. Other preferred modulating agents include LRAHAVDING-NH$_2$ (SEQ ID NO: 21), LRAHAVDVNG-NH$_2$ (SEQ ID NO: 22), MRAHAVDING-NH$_2$ (SEQ ID NO: 23), HLGAHAVDINGNQVET-NH$_2$ (SEQ ID NO: 24), FHLRAHAVDINGNQV-NH$_2$ (SEQ ID NO: 25), LYSHAVSSNG-NH$_2$ (SEQ ID NO: 18), derivatives of such sequences (e.g., N-Ac-LRAHAVDING-NH$_2$ (SEQ ID NO: 21), N-Ac-LRAHAVDVNG-NH$_2$ (SEQ ID NO: 22), N-Ac-MRAHAVDING-NH$_2$ (SEQ ID NO: 23), N-Ac-HLGA-HAVDINGNQVET-NH$_2$ (SEQ ID NO: 24), N-Ac-FHLRA-HAVDINGNQV-NH$_2$ (SEQ ID NO: 25), N-Ac-LYSHAVSSNG-NH$_2$ (SEQ ID NO: 18), N-Ac-LFSHAVSSNG-NH$_2$ (SEQ ID NO: 19), N-Ac-AHAVSE-NH$_2$ (SEQ ID NO: 27), N-Ac-AHAVDI-NH$_2$ (SEQ ID NO: 28), N-Ac-SHAVSS-NH$_2$ (SEQ ID NO: 29)) and modulating agents comprising such sequences or derivatives thereof. Bi-functional modulating agents that comprise an HAV sequence with flanking E-cadherin-specific sequences joined via a linker to an HAV sequence with flanking N-cadherin-specific sequences are also preferred. Preferably, the peptide portion(s) of a modulating agent comprises 3-16 amino acids, since longer peptides are difficult to dissolve in aqueous solution and are more likely to be degraded by peptidases. To achieve specificity for N- or E-cadherin mediated cell adhesion, the peptide portion(s) preferably comprise 4-16 amino acids, and more preferably 6-16 amino acids.

In one particularly preferred embodiment, a modulating agent is capable of disrupting cell adhesion mediated by multiple adhesion molecules. For example, a single branched modulating agent (or multiple agents linked to a single molecule or support material) may disrupt E-cadherin, N-cadherin, occludin, Dsc and Dsg mediated cell adhesion, thereby disrupting adherens junctions, tight junctions and desmosomes. Such an agent may comprise the cadherin CAR sequence, HAV, as well as the putative Dsc CAR sequences YAT, FAT, and YAS; the putative Dsg CAR sequence RAL; and the putative occludin CAR sequence GVNPTAQSSGSLYGSQIYALCNQFYTP-AATGLY-VDQYLYHYCVVDPQE (SEQ ID NO: 31) or a derivative thereof such as QSSGSLYGSQ (SEQ ID NO: 16) or QYLY-HYCVVD (SEQ ID NO: 17). Such agents serve as multifunctional disrupters of cell adhesion. Alternatively, a separate modulator of non-classical cadherin-mediated cell adhesion may be administered in conjunction with the modulating agent(s), either within the same pharmaceutical composition or separately. Preferred antibody modulating agents include Fab fragments directed against either the N-cadherin CAR sequence FHLRAHAVDINGNQV-NH2 (SEQ ID NO: 25) or E-cadherin CAR sequence LFSHAVSSNG-NH2 (SEQ ID NO: 18). Fab fragments directed against the occludin CAR sequence GVNPTAQSSGSLYGSQIYALCNQFYT-PAATGLYVDQYLYHYCVVDPQE (SEQ ID NO: 31) may also be employed, either incorporated into a modulating agent or within a separate modulator that is administered concurrently.

Preferably, the modulating agent and the drug are formulated within the same composition or drug delivery device prior to administration. In general, a modulating agent may enhance drug delivery to any tumor, and the method of administration may be chosen based on the type of target tumor. For example, injection or topical administration as described above may be preferred for melanomas and other accessible tumors (e.g., metastases from primary ovarian tumors may be treated by flushing the peritoneal cavity with the composition). Other tumors (e.g., bladder tumors) may be treated by injection of the modulating agent and the drug (such as mitomycin C) into the site of the tumor. In other instances, the composition may be administered systemically, and targeted to the tumor using any of a variety of specific targeting agents. Suitable drugs may be identified by those of ordinary skill in the art based upon the type of cancer to be treated (e.g., mitomycin C for bladder cancer). In general, the amount of modulating agent administered varies with the method of administration and the nature of the tumor, within the typical ranges provided above, preferably ranging from about 1 μg/mL to about 2 mg/mL, and more preferably from about 10 g/mL to 1 mg/mL. Transfer of the drug to the target tumor may be evaluated by appropriate means that will be apparent to those of ordinary skill in the art. Drugs may also be labeled (e.g., using radionuclides) to permit direct observation of transfer to the target tumor using standard imaging techniques.

Within a related aspect, the present invention provides methods for treating cancer and/or inhibiting metastasis in a mammal. Cancer tumors are solid masses of cells, growing out of control, which require nourishment via blood vessels. The formation of new capillaries is a prerequisite for tumor growth and the emergence of metastases. Administration of modulating agents as described herein may disrupt the growth of such blood vessels, thereby providing effective therapy for the cancer and/or inhibiting metastasis. Modulating agents may also be used to treat leukemias. Preferred modulating agents for use within such methods include those that disrupt N-cadherin and/or E-cadherin mediated cell adhesion, such as LRAHAVDING-$NH_2$ (SEQ ID NO: 21), LRAHAVDVNG-$NH_2$ (SEQ ID NO: 22), MRAHAVDING-$NH_2$ (SEQ ID NO: 23), HLGAHAVDINGNQVET-$NH_2$ (SEQ ID NO: 24), FHLRAHAVDINGNQV-$NH_2$ (SEQ ID NO: 25), AHAVSE-$NH_2$ (SEQ ID NO: 27), AHAVDI-$NH_2$ (SEQ ID NO: 28), LFSHAVSSNG-$NH_2$ (SEQ ID NO: 19), SHAVSS-$NH_2$ (SEQ ID NO: 29), LYSHAVSSNG-$NH_2$ (SEQ ID NO: 18), derivatives of such sequences (e.g., N-Ac-LRAHAVDING-$NH_2$ (SEQ ID NO: 21), N-Ac-LRAHAVDVNG-$NH_2$ (SEQ ID NO: 22), N-Ac-MRAHAVDING-$NH_2$ (SEQ ID NO: 23), N-Ac-HLGAHAVDINGNQVET-$NH_2$ (SEQ ID NO: 24), N-Ac-FHLRAHAVDINGNQV-$NH_2$ (SEQ ID NO: 25), N-Ac-LYSHAVSSNG-$NH_2$ (SEQ ID NO: 18), N-Ac-LFSHAVSSNG-$NH_2$ (SEQ ID NO: 19), N-Ac-AHAVSE-$NH_2$ (SEQ ID NO: 27), N-Ac-AHAVDI-$NH_2$ (SEQ ID NO: 28), N-Ac-SHAVSS-$NH_2$ (SEQ ID NO: 29)) and modulating agents comprising such sequences or derivatives thereof. Preferably, the peptide portion(s) of such modulating agents comprise 3-16 amino acids, more preferably 4-16 amino acids, since longer peptides are difficult to dissolve in aqueous solution and are more likely to be degraded by peptidases. Preferred antibody modulating agents include Fab fragments directed against either the N-cadherin CAR sequence FHLRAHAVDINGNQV-$NH_2$ (SEQ ID NO: 25) or E-cadherin CAR sequence LFSHAVSSNG-$NH_2$ (SEQ ID NO: 19). In addition, a modulating agent may comprise the sequence RGD, which is recognized by integrins, separated from the HAV sequence via a linker. A modulating agent may be administered alone (e.g., via the skin) or within a pharmaceutical composition. For melanomas and certain other accessible tumors, injection or topical administration as described above may be preferred. For ovarian cancers, flushing the peritoneal cavity with a composition comprising one or more modulating agents may prevent metastasis of ovarian tumor cells. Other tumors (e.g., bladder tumors, bronchial tumors or tracheal tumors) may be treated by injection of the modulating agent into the cavity. In other instances, the composition may be administered systemically, and targeted to the tumor using any of a variety of specific targeting agents, as described above. In general, the amount of modulating agent administered varies depending upon the method of administration and the nature of the cancer, but may vary within the ranges identified above. The effectiveness of the cancer treatment or inhibition of metastasis may be evaluated using well known clinical observations, such as monitoring the level of serum tumor markers (e.g., CEA or PSA).

Within a further related aspect, a modulating agent may be used to inhibit angiogenesis (i.e., the growth of blood vessels from pre-existing blood vessels) in a mammal. Inhibition of angiogenesis may be beneficial, for example, in patients afflicted with diseases such as cancer or arthritis. Preferred modulating agents for inhibition of angiogenesis include LRAHAVDING-$NH_2$ (SEQ ID NO: 21), LRAHAVDVNG-$NH_2$ (SEQ ID NO: 22), MRAHAVDING-$NH_2$ (SEQ ID NO: 23), HLGAHAVDINGNQVET-$NH_2$ (SEQ ID NO: 24), FHLRAHAVDINGNQV-$NH_2$ (SEQ ID NO: 25), AHAVDI-$NH_2$ (SEQ ID NO: 28), derivatives of such sequences (e.g., N-Ac-LRAHAVDING-$NH_2$ (SEQ ID NO: 21), N-Ac-LRAHAVDVNG-$NH_2$ (SEQ ID NO: 22), N-Ac-MRAHAVDING-$NH_2$ (SEQ ID NO: 23), N-Ac-HLGA- HAVDINGNQVET-NH$_2$ (SEQ ID NO: 24), N-Ac-FHLRAHAVDINGNQV-NH$_2$ (SEQ ID NO: 25), N-Ac-AHAVDI-NH$_2$ (SEQ ID NO: 28)) and modulating agents comprising such sequences or derivatives thereof. Preferred antibody modulating agents include Fab fragments directed against the N-cadherin CAR sequence FHLRAHAVDING-NQV-NH$_2$ (SEQ ID NO: 25). In addition, a modulating agent for use in inhibiting angiogenesis may comprise the sequence RGD, which is recognized by integrins, separated from the HAV sequence via a linker. Alternatively, a separate modulator of integrin-mediated cell adhesion may be administered in conjunction with the modulating agent(s), either within the same pharmaceutical composition or separately. The effect of a particular modulating agent on angiogenesis may generally be determined by evaluating the effect of the agent on blood vessel formation. Such a determination may generally be performed, for example, using a chick chorioallantoic membrane assay (Iruela-Arispe et al., *Molecular Biology of the Cell* 6:327-343, 1995). Briefly, a modulating agent may be embedded in a mesh composed of vitrogen at one or more concentrations (e.g., ranging from about 5 to 50 μg/mesh). The mesh(es) may then be applied to chick chorioallantoic membranes. After 24 hours, the effect of the modulating agent may be determined using computer assisted morphometric analysis. A modulating agent should inhibit angiogenesis by at least 25% at a concentration of 50 μg/mesh.

The addition of a targeting agent as described above may be beneficial, particularly when the administration is systemic. Suitable modes of administration and dosages depend upon the condition to be prevented or treated but, in general, administration by injection is appropriate. Dosages may vary as described above. The effectiveness of the inhibition may be evaluated grossly by assessing the inability of the tumors to maintain their growth and microscopically by observing an absence of nerves at the periphery of the tumor.

In yet another related aspect, the present invention provides methods for inducing apoptosis in a cadherin-expressing cell. In general, patients afflicted with cancer may benefit from such treatment. Certain preferred modulating agents for use within such methods comprise the sequence LRAHAVDING-NH$_2$ (SEQ ID NO: 21), LRAHAVDVNG-NH$_2$ (SEQ ID NO: 22), MRAHAVDING-NH$_2$ (SEQ ID NO: 23), HLGAHAVDINGNQVET-NH$_2$ (SEQ ID NO: 25), FHLRA-HAVDINGNQV-NH$_2$ (SEQ ID NO: 25), LYSHAVSSNG-NH$_2$ (SEQ ID NO: 18), AHAVSE-NH$_2$ (SEQ ID NO: 27), AHAVDI-NH$_2$ (SEQ ID NO: 28), SHAVSS-NH$_2$ (SEQ ID NO: 29), LFSHAVSSNG-NH$_2$ (SEQ ID NO: 19), derivatives of such sequences (e.g., N-Ac-LRAHAVDING-NH$_2$ (SEQ ID NO: 21), N-Ac-LRAHAVDVNG-NH$_2$ (SEQ ID NO: 22), N-Ac-MRAHAVDING-NH$_2$ (SEQ ID NO: 23), N-Ac-HLGAHAVDINGNQVET-NH$_2$ (SEQ ID NO: 24), N-Ac-FHLRAHAVDINGNQV-NH$_2$ (SEQ ID NO: 25), N-Ac-LYSHAVSSNG-NH$_2$ (SEQ ID NO: 18), N-Ac-AHAVSE-NH$_2$ (SEQ ID NO: 27), N-Ac-AHAVDI-NH$_2$ (SEQ ID NO: 28), N-Ac-SHAVSS-NH$_2$ (SEQ ID NO: 29), N-Ac-LFSHAVSSNG-NH$_2$ (SEQ ID NO: 19)) and modulating agents comprising such sequences or derivatives thereof. In addition, a preferred modulating agent may comprise the an additional CAR sequences, such as the sequence RGD, which is recognized by integrins. As noted above, such additional sequences may be separated from the HAV sequence via a linker. Alternatively, a separate modulator of integrin-mediated cell adhesion may be administered in conjunction with the modulating agent(s), either within the same pharmaceutical composition or separately. Preferred antibody modulating agents include Fab fragments directed against either the N-cadherin CAR sequence FHL-RAHAVDINGNQV-NH$_2$ (SEQ ID NO: 25) or E-cadherin CAR sequence LYSHAVSSNG-NH$_2$ (SEQ ID NO: 18). Administration may be topical, via injection or by other means, and the addition of a targeting agent may be beneficial, particularly when the administration is systemic. Suitable modes of administration and dosages depend upon the location and nature of the cells for which induction of apoptosis is desired but, in general, dosages may vary as described above. A biopsy may be performed to evaluate the level of induction of apoptosis.

The present invention also provides methods for enhancing drug delivery to the central nervous system of a mammal. The blood/brain barrier is largely impermeable to most neuroactive agents, and delivery of drugs to the brain of a mammal often requires invasive procedures. Using a modulating agent as described herein, however, delivery may be by, for example, systemic administration of a modulating agent-drug-targeting agent combination, injection of a modulating agent (alone or in combination with a drug and/or targeting agent) into the carotid artery or application of a skin patch comprising a modulating agent to the head of the patient. Certain preferred modulating agents for use within such methods are LRAHAVDING-NH$_2$ (SEQ ID NO: 21), LRAHAVDVNG-NH$_2$ (SEQ ID NO: 22), MRA-HAVDING-NH$_2$ (SEQ ID NO: 23), HLGAHAVDINGN-QVET-NH$_2$ (SEQ ID NO: 24), FHLRAHAVDINGNQV-NH2 (SEQ ID NO: 25), AHAVSE-NH2 (SEQ ID NO: 27), AHAVDI-NH$_2$ (SEQ ID NO: 28), derivatives of such sequences (e.g., N-Ac-LRAHAVDING-NH$_2$ (SEQ ID NO: 21), N-Ac-LRAHAVDVNG-NH$_2$ (SEQ ID NO: 22), N-Ac-MRAHAVDING-NH$_2$ (SEQ ID NO: 23), N-Ac-HLGA-HAVDINGNQVET-NH$_2$ (SEQ ID NO: 24), N-Ac-FHLRA-HAVDINGNQV-NH$_2$ (SEQ ID NO: 25), N-Ac-AHAVSE-NH$_2$ (SEQ ID NO: 27), N-Ac-AHAVDI-NH$_2$ (SEQ ID NO: 28)) and modulating agents comprising such sequences or derivatives thereof. Also preferred are bi-functional modulating agents comprising a cadherin CAR sequence and the putative occludin CAR sequence GVNPTAQSSGSLYGS-QIYALCNQFYTPAATGLYV-DQYLYHYCVVDPQE (SEQ ID NO: 31), or derivatives or portions thereof such as QSSGSLYGSQ (SEQ ID NO: 16) and QYLYHYCVVD (SEQ ID NO: 17), preferably joined by a linker. Alternatively, a separate modulator of occludin-mediated cell adhesion may be administered in conjunction with the modulating agent(s), either within the same pharmaceutical composition or separately. Preferably, the peptide portion(s) of such modulating agents comprise 3-16 amino acids, more preferably 4-16 amino acids. Preferred antibody modulating agents include Fab fragments directed against the N-cadherin CAR sequence FHLRAHAVDINGNQV-NH$_2$ (SEQ ID NO: 25). Fab fragments directed against the occludin CAR sequence GVNPTAQSSGSLYGSQIYALCNQFYT-PAATGLY-VDQYLYHYCVVDPQE (SEQ ID NO: 31) may also be employed, either incorporated into the modulating agent or administered concurrently as a separate modulator. In general, the amount of modulating agent administered varies with the method of administration and the nature of the condition to be treated or prevented, but typically varies as described above. Transfer of the drug to the central nervous system may be evaluated by appropriate means that will be apparent to those of ordinary skill in the art, such as magnetic resonance imaging (MRI) or PET scan (positron emitted tomography).

The present invention also provides, within further aspects, methods for enhancing and/or directing neurological growth. In one aspect, neurite outgrowth may be enhanced and/or directed by contacting a neuron with one or more modulating agents. Preferred modulating agents for use within such methods are linked to a polymeric matrix or other support and/or contain multiple HAV sequences separated by one or more linkers. Peptides that may be linked to a support material (and/or to one another via a linker to generate a suitable modulating agent) include, but are not limited to, LRAHAVDING-$NH_2$ (SEQ ID NO: 21), LRA-HAVDVNG-$NH_2$ (SEQ ID NO: 22), MRAHAVDING-$NH_2$ (SEQ ID NO: 23), HLGAHAVDINGNQVET-$NH_2$ (SEQ ID NO: 24), FHLRAHAVDINGNQV-$NH_2$ (SEQ ID NO: 25), AHAVDI-$NH_2$ (SEQ ID NO: 28), derivatives of such sequences (e.g., N-Ac-LRAHAVDING-$NH_2$ (SEQ ID NO: 21), N-Ac-LRAHAVDVNG-$NH_2$ (SEQ ID NO: 22), N-Ac-MRAHAVDING-$NH_2$ (SEQ ID NO: 23), N-Ac-HLGA-HAVDINGNQVET-$NH_2$ (SEQ ID NO: 24), N-Ac-FHLRA-HAVDINGNQV-$NH_2$ (SEQ ID NO: 25), N-Ac-AHAVDI-$NH_2$ (SEQ ID NO: 28)) and modulating agents comprising such sequences or derivatives thereof. In addition, a modulating agent comprising RGD and/or YIGSR (SEQ ID NO: 12), which are bound by integrins, the cadherin CAR sequence HAV, and/or the N-CAM CAR sequence KYS-FNYDGSE (SEQ ID NO: 13) may further facilitate neurite outgrowth. Modulating agents comprising antibodies, or fragments thereof, may be used within this aspect of the present invention without the use of linkers or support materials. Preferred antibody modulating agents include Fab fragments directed against the N-cadherin CAR sequence FHLRAHAVDINGNQV-$NH_2$ (SEQ ID NO: 25). Fab fragments directed against the N-CAM CAR sequence KYS-FNYDGSE (SEQ ID NO: 13) may also be employed, either incorporated into the modulating agent or administered concurrently as a separate modulator.

The method of achieving contact and the amount of modulating agent used will depend upon the location of the neuron and the extent and nature of the outgrowth desired. For example, a neuron may be contacted (e.g., via implantation) with modulating agent(s) linked to a support material such as a suture, fiber nerve guide or other prosthetic device such that the neurite outgrowth is directed along the support material. Alternatively, a tubular nerve guide may be employed, in which the lumen of the nerve guide contains a composition comprising the modulating agent(s). In vivo, such nerve guides or other supported modulating agents may be implanted using well known techniques to, for example, facilitate the growth of severed neuronal connections and/or to treat spinal cord injuries. It will be apparent to those of ordinary skill in the art that the structure and composition of the support should be appropriate for the particular injury being treated. In vitro, a polymeric matrix may similarly be used to direct the growth of neurons onto patterned surfaces as described, for example, in U.S. Pat. No. 5,510,628.

In certain other aspects, the present invention provides methods for enhancing adhesion of cadherin-expressing cells. Within certain embodiments, a modulating agent may be linked to a solid support, resulting in a matrix that comprises multiple modulating agents. Within one such embodiment, the support is a polymeric matrix to which modulating agents and molecules comprising other CAR sequence(s) are attached (e.g., modulating agents and molecules comprising an RGD sequence may be attached to the same matrix, preferably in an alternating pattern). Such matrices may be used in contexts in which it is desirable to enhance adhesion mediated by multiple cell adhesion molecules. Alternatively, the modulating agent itself may comprise multiple HAV sequences or antibodies (or fragments thereof), separated by linkers as described above. Either way, the modulating agent(s) function as a "biological glue" to bind multiple cadherin-expressing cells within a variety of contexts.

Within one such aspect, modulating agents comprising multiple HAV sequences and/or multiple modulating agents linked to a single molecule or support material may be used to enhance wound healing and/or reduce scar tissue in a mammal. Peptides that may be linked to a support, and/or to one another via a linker, to generate a suitable modulating agent include, but are not limited to, LYSHAVSSNG-$NH_2$ (SEQ ID NO: 18), AHAVSE-$NH_2$ (SEQ ID NO: 27), SHAVSS-$NH_2$ (SEQ ID NO: 29), LFSHAVSSNG-$NH_2$ (SEQ ID NO: 19), derivatives of such sequences (e.g., N-Ac-LYSHAVSSNG-$NH_2$ (SEQ ID NO: 18), N-Ac-AHAVSE-$NH_2$ (SEQ ID NO: 27), N-Ac-SHAVSS-$NH_2$ (SEQ ID NO: 29), N-Ac-LFSHAVSSNG-$NH_2$ (SEQ ID NO: 19)) and modulating agents comprising such sequences or derivatives thereof. Preferred antibody modulating agents include Fab fragments directed against the E-cadherin CAR sequence LFSHAVSSNG-$NH_2$ (SEQ ID NO: 19). Modulating agents that are linked to a biocompatible and biodegradable matrix such as cellulose or collagen are particularly preferred. For use within such methods, a modulating agent should have a free amino or hydroxyl group. The modulating agents are generally administered topically to the wound, where they may facilitate closure of the wound and may augment, or even replace, stitches. Similarly, administration of matrix-linked modulating agents may facilitate cell adhesion in skin grafting and prosthetic implants, and may prolong the duration and usefulness of collagen injection. In general, the amount of matrix-linked modulating agent administered to a wound, graft or implant site varies with the severity of the wound and/or the nature of the wound, graft, or implant, but may vary as discussed above. Multi-functional modulating agents comprising the cadherin CAR sequence, HAV, the integrin CAR sequence, RGD, as well as the putative Dsc and Dsg CAR sequences YAT, FAT, YAS and RAL may also be used as potent stimulators of wound healing and/or to reduce scar tissue. Alternatively, one or more separate modulator of integrin-, Dsc- and/or Dsg-mediated cell adhesion may be administered in conjunction with the modulating agent(s), either within the same pharmaceutical composition or separately.

Within another aspect, one or more modulating agents may be linked to the interior surface of a tissue culture plate or other cell culture support, such as for use in a bioreactor. Such linkage may be performed by any suitable technique, as described above. Modulating agents linked in this fashion may generally be used to immobilize cadherin-expressing cells. For example, dishes or plates coated with one or more modulating agents may be used to immobilize cadherin-expressing cells within a variety of assays and screens. Within bioreactors (i.e., systems for large scale production of cells or organoids), modulating agents may generally be used to improve cell attachment and stabilize cell growth. Modulating agents may also be used within bioreactors to support the formation and function of highly differentiated organoids derived, for example, from dispersed populations of fetal mammalian cells. Bioreactors containing biomatrices of modulating agent(s) may also be used to facilitate the production of specific proteins.

Modulating agents as described herein may be used within a variety of bioreactor configurations. In general, a bioreactor is designed with an interior surface area sufficient to support large numbers of adherent cells. This surface area can be provided using membranes, tubes, microtiter wells, columns, hollow fibers, roller bottles, plates, dishes, beads or a combination thereof. A bioreactor may be compartmentalized. The support material within a bioreactor may be any suitable material known in the art; preferably, the support material does not dissolve or swell in water. Preferred support materials include, but are not limited to, synthetic polymers such as acrylics, vinyls, polyethylene, polypropylene, polytetrafluoroethylene, nylons, polyurethanes, polyamides, polysulfones and poly(ethylene terephthalate); ceramics; glass and silica.

Within further aspects, modulating agents as described herein may be used for modulating the immune system of a mammal in any of several ways. Cadherins are expressed on immature B and T cells (thymocytes and bone marrow pre-B cells), as well as on specific subsets of activated B and T lymphocytes and some hematological malignancies (see Lee et al., *J. Immunol.* 152:5653-5659, 1994; Munro et al., *Cellular Immunol.* 169:309-312, 1996; Tsutsui et al., *J. Biochem.* 120:1034-1039, 1996; Cepek et al., *Proc. Natl. Acad. Sci. USA* 93:6567-6571, 1996). Modulating agents may generally be used to modulate specific steps within cellular interactions during an immune response or during the dissemination of malignant lymphocytes.

For example, a modulating agent as described herein may be used to treat diseases associated with excessive generation of otherwise normal T cells. Without wishing to be bound by any particular theory, it is believed that the interaction of cadherins on maturing T cells and B cell subsets contributes to protection of these cells from programmed cell death. A modulating agent may decrease such interactions, leading to the induction of programmed cell death. Accordingly, modulating agents may be used to treat certain types of diabetes and rheumatoid arthritis, particularly in young children where the cadherin expression on thymic pre-Tcells is greatest.

Modulating agents may also be administered to patients afflicted with certain skin disorders (such as cutaneous lymphomas), acute B cell leukemia and excessive immune reactions involving the humoral immune system and generation of immunoglobulins, such as allergic responses and antibody-mediated graft rejection. In addition, patients with circulating cadherin-positive malignant cells (e.g., during regimes where chemotherapy or radiation therapy is eliminating a major portion of the malignant cells in bone marrow and other lymphoid tissue) may benefit from treatment with a modulating agent. Such treatment may also benefit patients undergoing transplantation with peripheral blood stem cells.

Preferred modulating agents for use within such methods include those that disrupt E-cadherin and/or N-cadherin mediated cell adhesion, such as LRAHAVDING-NH$_2$ (SEQ ID NO: 21), LRAHAVDVNG-NH$_2$ (SEQ ID NO: 22), MRAHAVDING-NH$_2$ (SEQ ID NO: 23), HLGAHAVDING-NQVET-NH$_2$ (SEQ ID NO: 24), FHLRAHAVDINGNQV-NH$_2$ (SEQ ID NO: 25), LYSHAVSSNG-NH$_2$ (SEQ ID NO: 18), AHAVSE-NH$_2$ (SEQ ID NO: 27), AHAVDI-NH$_2$ (SEQ ID NO: 28), SHAVSS-NH$_2$ (SEQ ID NO: 29), LFSHAVSSNG-NH$_2$ (SEQ ID NO: 19), derivatives of such sequences (e.g., N-Ac-LRAHAVDING-NH$_2$ (SEQ ID NO: 21), N-Ac-LRAHAVDVNG-NH$_2$ (SEQ ID NO: 22), N-Ac-MRAHAVDING-NH$_2$ (SEQ ID NO: 23), N-Ac-HLGA-HAVDINGNQVET-NH$_2$ (SEQ ID NO: 24), N-Ac-FHLRA-HAVDINGNQV-NH$_2$ (SEQ ID NO: 25), N-Ac-LYSHAVSSNG-NH$_2$ (SEQ ID NO: 18), N-Ac-AHAVSE-NH$_2$ (SEQ ID NO: 27), N-Ac-AHAVDI-NH$_2$ (SEQ ID NO: 28), N-Ac-SHAVSS-NH$_2$ (SEQ ID NO: 29), N-Ac-LF-SHAVSSNG-NH$_2$ (SEQ ID NO: 19)) and modulating agents comprising such sequences or derivatives thereof. In addition, a preferred modulating agent may comprise one or more additional CAR sequences, such as the sequence RGD, which is bound by integrins. As noted above, such additional sequence(s) may be separated from the HAV sequence via a linker. Alternatively, a separate modulator of integrin-mediated cell adhesion may be administered in conjunction with the modulating agent(s), either within the same pharmaceutical composition or separately. Preferred antibody modulating agents include Fab fragments directed against either the N-cadherin CAR sequence FHLRAHAVDINGNQV-NH$_2$ (SEQ ID NO: 25) or E-cadherin CAR sequence LYSHAVSSNG-NH$_2$ (SEQ ID NO: 18). Within the above methods, the modulating agent(s) are preferably administered systemically (usually by injection) or topically. A modulating agent may be linked to a targeting agent. For example, targeting to the bone marrow may be beneficial. A suitable dosage is sufficient to effect a statistically significant reduction in the population of B and/or T cells that express cadherin and/or an improvement in the clinical manifestation of the disease being treated. Typical dosages generally range as described above.

Within further aspects, the present invention provides methods and kits for preventing pregnancy in a mammal. In general, disruption of E-cadherin function prevents the adhesion of trophoblasts and their subsequent fusion to form syncitiotrophoblasts. In one embodiment, one or more modulating agents as described herein may be incorporated into any of a variety of well known contraceptive devices, such as sponges suitable for intravaginal insertion (see, e.g., U.S. Pat. No. 5,417,224) or capsules for subdermal implantation. Other modes of administration are possible, however, including transdermal administration, for modulating agents linked to an appropriate targeting agent. Preferred modulating agents for use within such methods include LYSHAVSSNG-NH$_2$ (SEQ ID NO: 18), AHAVSE-NH$_2$ (SEQ ID NO: 27), SHAVSS-NH$_2$ (SEQ ID NO: 29), LFSHAVSSNG-NH$_2$ (SEQ ID NO: 19), derivatives of such sequences (e.g., N-Ac-LYSHAVSSNG-NH$_2$ (SEQ ID NO: 18), N-Ac-AHAVSE-NH$_2$ (SEQ ID NO: 27), N-Ac-SHAVSS-NH$_2$ (SEQ ID NO: 29) and N-Ac-LFSHAVSSNG-NH$_2$ (SEQ ID NO: 19)) and modulating agents comprising such sequences or derivatives thereof. In addition, a preferred modulating agent may comprise additional CAR sequences, such as the sequence RGD, which is bound by integrins. As noted above, such additional sequences may be separated from the HAV sequence via a linker. Alternatively, a separate modulator of integrin-mediated cell adhesion may be administered in conjunction with the modulating agent(s), either within the same pharmaceutical composition or separately. Preferred antibody modulating agents include Fab fragments directed against the E-cadherin CAR sequence LFSHAVSSNG-NH$_2$ (SEQ ID NO: 19). Suitable methods for incorporation into such a device depend upon the type of device and are well known in the art. Such devices facilitate administration of the modulating agent(s) to the uterine region and may provide a sustained release of the modulating agent(s). In general, modulating agent(s) may be administered via such a contraceptive device at a dosage ranging from 0.1 to 50 mg/kg, although appropriate dosages may be determined by monitoring hCG levels in the urine. hCG is produced by the placenta, and levels of this hormone rise in the urine of pregnant women. The urine hCG levels can be assessed by radio-immunoassay using well known techniques. Kits for preventing pregnancy generally comprise a contraceptive device impregnated with one or more modulating agents.

Alternatively, a sustained release formulation of one or more modulating agents may be implanted, typically subdermally, in a mammal for the prevention of pregnancy. Such implantation may be performed using well known techniques. Preferably, the implanted formulation provides a dosage as described above, although the minimum effective dosage may be determined by those of ordinary skill in the art using, for example, an evaluation of hCG levels in the urine of women.

The present invention also provides methods for increasing vasopermeability in a mammal by administering one or more modulating agents or pharmaceutical compositions. Within blood vessels, endothelial cell adhesion (mediated by N-cadherin) results in decreased vascular permeability. Accordingly, modulating agents as described herein that decrease N-cadherin mediated adhesion may be used to increase vascular permeability. Particularly preferred modulating agents include LRAHAVDING-NH$_2$ (SEQ ID NO: 21), LRAHAVDVNG-NH$_2$ (SEQ ID NO: 22), MRA-HAVDING-NH$_2$ (SEQ ID NO: 23), HLGAHAVDINGN-QVET-NH$_2$ (SEQ ID NO: 24), FHLRAHAVDINGNQV-NH$_2$ (SEQ ID NO: 25), AHAVDI-NH$_2$ (SEQ ID NO: 28), derivatives of such sequences (e.g., N-Ac-LRAHAVDING-NH$_2$ (SEQ ID NO: 21), N-Ac-LRAHAVDVNG-NH$_2$ (SEQ ID NO: 22), N-Ac-MRAHAVDING-NH$_2$ (SEQ ID NO: 23), N-Ac-HLGAHAVDINGNQVET-NH$_2$ (SEQ ID NO: 24), N-Ac-FHLRAHAVDINGNQV-NH$_2$ (SEQ ID NO: 25), AHAVDI-NH$_2$ (SEQ ID NO: 28)) and modulating agents comprising such sequences or derivatives thereof. Modulating agents comprising antibodies, or fragments thereof, may also be used within this aspect of the present invention. Preferred antibody modulating agents include Fab fragments directed against the N-cadherin CAR sequence FHLRA-HAVDINGNQV-NH$_2$ (SEQ ID NO: 25).

Within certain embodiments, preferred modulating agents for use within such methods include peptides capable of decreasing both endothelial and tumor cell adhesion. Such modulating agents may be used to facilitate the penetration of anti-tumor therapeutic or diagnostic agents (e.g., monoclonal antibodies) through endothelial cell permeability barriers and tumor barriers. For example, a modulating agent may further comprise a sequence such as SHAVSS-NH$_2$ (SEQ ID NO: 29), LFSHAVSSNG-NH$_2$ (SEQ ID NO: 19), AHAVSE-NH$_2$ (SEQ ID NO: 27), LYSHAVSSNG-NH$_2$ (SEQ ID NO: 18), and/or one or more derivatives of such sequences (e.g., N-Ac-SHAVSS-NH$_2$ (SEQ ID NO: 29), N-Ac-LFSHAVSSNG-NH$_2$ (SEQ ID NO: 19), N-Ac-AHAVSE-NH$_2$ (SEQ ID NO: 27) or N-Ac-LYSHAVSSNG-NH$_2$ (SEQ ID NO: 18)). Bi-functional modulating agents that comprise an HAV sequence with flanking E-cadherin-specific sequences joined via a linker to an HAV sequence with flanking N-cadherin-specific sequences are also preferred. Alternatively, separate modulating agents capable of disrupting N- and E-cadherin mediated adhesion may be administered concurrently. Preferably, the peptide portion(s) of a modulating agent comprises 3-16 amino acids, since longer peptides are difficult to dissolve in aqueous solution and are more likely to be degraded by peptidases.

In one particularly preferred embodiment, a modulating agent is further capable of disrupting cell adhesion mediated by multiple adhesion molecules. Such an agent may comprise the cadherin CAR sequence, HAV, as well as and RGD sequence and/or the putative occludin CAR sequence GVNPTAQSSGSLYGSQIYALCNQFYTP-AATGLYVDQYLYHYCVVDPQE (SEQ ID NO: 31) or a derivative thereof such as QSSGSLYGSQ (SEQ ID NO: 16) or QYLYHYCVVD (SEQ ID NO: 17). Alternatively, a separate modulator of non-classical cadherin-mediated cell adhesion may be administered in conjunction with the modulating agent(s), either within the same pharmaceutical composition or separately. Preferred antibody modulating agents include Fab fragments directed against either the N-cadherin CAR sequence FHLRAHAVDINGNQV-$NH_2$ (SEQ ID NO: 25) or E-cadherin CAR sequence LFSHAVSSNG-$NH_2$ (SEQ ID NO: 18). Fab fragments directed against the occiudin CAR sequence GVNPTAQSSGSLYGSQIYALCNQFYT-PAATGLYVDQYLYHYCVV-DPQE (SEQ ID NO: 31) may also be employed, either incorporated into a modulating agent or within a separate modulator that is administered concurrently.

Treatment with a modulating agent may be appropriate, for example, prior to administration of an anti-tumor therapeutic or diagnostic agent (e.g., a monoclonal antibody or other macromolecule), an antimicrobial agent or an anti-inflammatory agent, in order to increase the concentration of such agents in the vicinity of the target tumor, organism or inflammation without increasing the overall dose to the patient. Modulating agents for use within such methods may be linked to a targeting agent to further increase the local concentration of modulating agent, although systemic administration of a vasoactive agent even in the absence of a targeting agent increases the perfusion of certain tumors relative to other tissues. Suitable targeting agents include antibodies and other molecules that specifically bind to tumor cells or to components of structurally abnormal blood vessels. For example, a targeting agent may be an antibody that binds to a fibrin degradation product or a cell enzyme such as a peroxidase that is released by granulocytes or other cells in necrotic or inflamed tissues.

Administration via intravenous injection or transdermal administration is generally preferred. Effective dosages are generally sufficient to increase localization of a subsequently administered diagnostic or therapeutic agent to an extent that improves the clinical efficacy of therapy of accuracy of diagnosis to a statistically significant degree. Comparison may be made between treated and untreated tumor host animals to whom equivalent doses of the diagnostic or therapeutic agent are administered. In general, dosages range as described above.

Within a further aspect, modulating agents as described herein may be used for controlled inhibition of synaptic stability, resulting in increased synaptic plasticity. Within this aspect, administration of one or more modulating agents may be advantageous for repair processes within the brain, as well as learning and memory, in which neural plasticity is a key early event in the remodeling of synapses. Cell adhesion molecules, particularly N-cadherin and E-cadherin, can function to stabilize synapses, and loss of this function is thought to be the initial step in the remodeling of the synapse that is associated with learning and memory (Doherty. et al., *J. Neurobiology* , 26:437-446, 1995; Martin and Kandel, *Neuron*, 17:567-570, 1996; Fannon and Colman, *Neuron*, 17:423-434, 1996). Inhibition of cadherin function by administration of one or more modulating agents that inhibit cadherin function may stimulate learning and memory. Preferred modulating agents for use within such methods include those that disrupt E-cadherin and/or N-cadherin mediated cell adhesion, such as LRAHAVDING-$NH_2$ (SEQ ID NO: 21), LRAHAVDVNG-$NH_2$ (SEQ ID NO: 22), MRAHAVDING-$NH_2$ (SEQ ID NO: 23), HLGAHAVDINGNQVET-$NH_2$ (SEQ ID NO: 24), FHLRAHAVDINGNQV-$NH_2$ (SEQ ID NO: 25), LYSHAVSSNG-$NH_2$ (SEQ ID NO: 18), AHAVSE-$NH_2$ (SEQ ID NO: 27), AHAVDI-NH2 (SEQ ID NO: 28), SHAVSS-$NH_2$ (SEQ ID NO: 29), LFSHAVSSNG-NH2 (SEQ ID NO: 19), derivatives of such sequences (e.g., N-Ac-LRAHAVDING-$NH_2$ (SEQ ID NO: 21), N-Ac-LRAHAVDVNG-NH$_2$ (SEQ ID NO: 22), N-Ac-MRAHAVDING-NH$_2$ (SEQ ID NO: 23), N-Ac-HLGAHAVDINGNQVET-NH$_2$ (SEQ ID NO: 24), N-Ac-FHLRAHAVDINGNQV-NH2 (SEQ ID NO: 25), N-Ac-LYSHAVSSNG-NH$_2$ (SEQ ID NO: 18), N-Ac-AHAVSE-NH$_2$ (SEQ ID NO: 27), N-Ac-AHAVDI-NH$_2$ (SEQ ID NO: 28), N-Ac-SHAVSS-NH2 (SEQ ID NO: 29), N-Ac-LFSHAVSSNG-NH$_2$ (SEQ ID NO: 19)) and modulating agents comprising such sequences or derivatives thereof. In addition, a preferred modulating agent may comprise one or more additional CAR sequences, such as the sequence RGD, which is bound by integrins and/or the N-CAM CAR sequence KYSFNYDGSE (SEQ ID NO: 12). As noted above, such additional sequence(s) may be separated from the HAV sequence via a linker. Alternatively, a separate modulator of integrin and/or N-CAM mediated cell adhesion may be administered in conjunction with the modulating agent(s), either within the same pharmaceutical composition or separately. Preferred antibody modulating agents include Fab fragments directed against either the N-cadherin CAR sequence FHLRAHAVDINGNQV-NH$_2$ (SEQ ID NO: 25) or E-cadherin CAR sequence LFSHAVSSNG-NH$_2$ (SEQ ID NO: 19). For such aspects, administration may be via encapsulation into a delivery vehicle such as a liposome, using standard techniques, and injection into, for example, the carotid artery. Alternatively, a modulating agent may be linked to a disrupter of the blood-brain barrier. In general dosages range as described above.

Other aspects of the present invention provide methods that employ antibodies raised against the modulating agents for diagnostic and assay purposes. Assays typically involve using an antibody to detect the presence or absence of a cadherin (free or on the surface of a cell), or proteolytic fragment containing the EC1 domain in a suitable biological sample, such as tumor or normal tissue biopsies, blood, lymph node, serum or urine samples, or other tissue, homogenate, or extract thereof obtained from a patient.

There are a variety of assay formats known to those of ordinary skill in the art for using an antibody to detect a target molecule in a sample. See, e.g., Harlow and Lane, *Antibodies: A Laboratory Manual*, Cold Spring Harbor Laboratory, 1988. For example, the assay may be performed in a Western blot format, wherein a protein preparation from the biological sample is submitted to gel electrophoresis, transferred to a suitable membrane and allowed to react with the antibody. The presence of the antibody on the membrane may then be detected using a suitable detection reagent, as described below.

In another embodiment, the assay involves the use of antibody immobilized on a solid support to bind to the target cadherin, or a proteolytic fragment containing the EC1 domain and encompassing the CAR sequence, and remove it from the remainder of the sample. The bound cadherin may then be detected using a second antibody or reagent that contains a reporter group. Alternatively, a competitive assay may be utilized, in which a cadherin is labeled with a reporter group and allowed to bind to the immobilized antibody after incubation of the antibody with the sample. The extent to which components of the sample inhibit the binding of the labeled cadherin to the antibody is indicative of the reactivity of the sample with the immobilized antibody, and as a result, indicative of the level of the cadherin in the sample.

The solid support may be any material known to those of ordinary skill in the art to which the antibody may be attached, such as a test well in a microtiter plate, a nitrocellulose filter or another suitable membrane. Alternatively, the support may be a bead or disc, such as glass, fiberglass, latex or a plastic such as polystyrene or polyvinylchloride. The antibody may be immobilized on the solid support using a variety of techniques known to those in the art, which are amply described in the patent and scientific literature.

In certain embodiments, the assay for detection of a cadherin in a sample is a two-antibody sandwich assay. This assay may be performed by first contacting an antibody that has been immobilized on a solid support, commonly the well of a microtiter plate, with the biological sample, such that the cadherin within the sample is allowed to bind to the immobilized antibody (a 30 minute incubation time at room temperature is generally sufficient). Unbound sample is then removed from the immobilized cadherin-antibody complexes and a second antibody (containing a reporter group such as an enzyme, dye, radionuclide, luminescent group, fluorescent group or biotin) capable of binding to a different site on the cadherin is added. The amount of second antibody that remains bound to the solid support is then determined using a method appropriate for the specific reporter group. The method employed for detecting the reporter group depends upon the nature of the reporter group. For radioactive groups, scintillation counting or autoradiographic methods are generally appropriate. Spectroscopic methods may be used to detect dyes, luminescent groups and fluorescent groups. Biotin may be detected using avidin, coupled to a different reporter group (commonly a radioactive or fluorescent group or an enzyme). Enzyme reporter groups may generally be detected by the addition of substrate (generally for a specific period of time), followed by spectroscopic or other analysis of the reaction products. Standards and standard additions may be used to determine the level of cadherin in a sample, using well known techniques.

The present invention also provides kits for use in such immunoassays. Such kits generally comprise one or more antibodies, as described above. In addition, one or more additional compartments or containers of a kit generally enclose elements, such as reagents, buffers and/or wash solutions, to be used in the immunoassay.

Within further aspects, modulating agents or antibodies (or fragments thereof) may be used to facilitate cell identification and sorting in vitro or imaging in vivo, permitting the selection of cells expressing different cadherins (or different cadherin levels). Preferably, the modulating agent(s) or antibodies for use in such methods are linked to a detectable marker. Suitable markers are well known in the art and include radionuclides, luminescent groups, fluorescent groups, enzymes, dyes, constant immunoglobulin domains and biotin. Within one preferred embodiment, a modulating agent linked to a fluorescent marker, such as fluorescein, is contacted with the cells, which are then analyzed by fluorescence activated cell sorting (FACS).

Antibodies or fragments thereof may also be used within screens of combinatorial or other nonpeptide-based libraries to identify other compounds capable of modulating cadherin-mediated cell adhesion. Such screens may generally be performed using an ELISA or other method well known to those of ordinary skill in the art that detect compounds with a shape and structure similar to that of the modulating agent. In general, such screens may involve contacting an expression library producing test compounds with an antibody, and detecting the level of antibody bound to the candidate compounds. Compounds for which the antibody has a higher affinity may be further characterized as described herein, to evaluate the ability to modulate cadherin-mediated cell adhesion.

The following examples are offered by way of illustration and not by way of limitation.

EXAMPLE 1

Preparation of Representative Modulating Agents

This Example illustrates the solid phase synthesis of representative peptide modulating agents.

The peptides were assembled on either methylbenzhydrylamine (MBHA) resin (for the C-terminal amide peptides) or the traditional Merrifield resins (for any C-terminal acid peptides). Bags of a polypropylene mesh material were filled with the resin and soaked in dichloromethane. The resin packets were washed three times with 5% diisopropylethylamine in dichloromethane and then washed with dichloromethane. The packets are then sorted and placed into a Nalgene bottle containing a solution of the amino acid of interest in dichloromethane. An equal amount of diisopropylcarbodiimide (DIC) in dichloromethane was added to activate the coupling reaction. The bottle was shaken for one hour to ensure completion of the reaction. The reaction mixture was discarded and the packets washed with DMF. The N-α-Boc was removed by acidolysis using a 55% TFA in dichloromethane for 30 minutes leaving the TFA salt of the α-amino group. The bags were washed and the synthesis completed by repeating the same procedure while substituting for the corresponding amino acid at the coupling step. Acetylation of the N-terminal, where desired, was performed by reacting the peptide resins with a solution of acetic anhydride in dichloromethane in the presence of diisopropylethylamine. The peptide was then side-chain deprotected and cleaved from the resin at 0° C. with liquid HF in the presence of anisole as a carbocation scavenger.

The crude peptides were purified by reversed-phase high-performance liquid chromatography and characterized by analytical HPLC and by mass spectral analysis.

EXAMPLE 2

Establishment of a Model System for Schwann Cell-Astrocyte Interactions

This Example illustrates a cell boundary assay for use in evaluating interactions between Schwann cells and astrocytes.

A. Cell Culture

All cells were cultured in Dulbecco's modified Eagle's medium (DMEM; Gibco, Grand Island, N.Y.) supplemented with penicillin/streptomycin (100 U/ml; Gibco) and either 10% fetal calf serum (FCS) or serum-free (SF) medium; a modification of Bottenstein's and Sato's (*Proc. Natl. Acad. Sci USA* 76:514-517, 1979) defined medium with supplements of insulin (5 µg/ml; Sigma, St. Louis, Mo.), transferrin (100 µg/ml; Sigma), glutamine (1 mM; ICN/Flow), progesterone (60 ng/ml; Sigma), putrescine (16 µg/ml; Sigma), selenium (160 ng/ml; Sigma), T4 (500 ng/ml; Sigma), T3 (10 ng/ml; Sigma), BSA (0.035%; Sigma) and dexamethasone (38 ng/ml; Sigma).

Schwann cells were cultured from neonatal day 2 (P2) sciatic nerve, a variation of the procedure described by Brockes et al., *Brain Res.* 165:105-118, 1979. Nerves were removed and placed in L-15 medium, cleaned of any blood vessels, musculature and their epineurial sheaths and placed into a 34 mm diameter plastic dish containing Trypsin (0.1%; Sigma) and collagenase (0.03%; Sigma). The nerves were cut very finely using dissection scissors and placed in an incubator at 37° C. and 10% $CO_2$ for 30 minutes. Following this incubation an equal volume of triturating solution (300 mg BSA; Sigma, 1 mg DNAse; Sigma, 50 mg Trypsin inhibitor; Sigma per 100 ml HBSS) was added and the whole mixture gently triturated using a flamed glass pasteur. Having spun down the cells into a pellet by centrifugation at 1000 rpm for 3-5 minutes, the cells were then resuspended in DMEM with 10% FCS and plated on poly-lysine (0.01% Sigma) at a density of 5000 cells/mm². On the following day cells were treated with Cytosine arabinoside (Ara-C $1\times10^{-5}$M; Sigma) for three days. Following a period of two days in normal untreated FCS the ARA-C was again applied for a further three days. The few remaining fibroblast contaminants were then killed via complement mediated lysis using rabbit serum (a gift from R. Oldroyd) and the IgM class anti-Thy1.I (1:1000 Serotec, Kidlington, Oxford, UK). Subsequently, the Schwann cells (>98% pure) were maintained in FCS supplemented with bovine pituitary extract (BPE; 10 µg/ml; Sigma) and forskolin (2 µM, Sigma). These cells were maintained for experiments until two weeks after the treatment with complement.

Primary astrocyte cultures were obtained from neonatal rats (P2) as described by McCarthy and de Vellis, *J. Cell Biol.* 85:890-902,1980. The brains were removed, de-membraned, chopped and then incubated with 0.1% trypsin for 30 minutes. The mixture was then triturated in triturating solution and the cells were centrifuged down into a pellet. Having resuspended the cells in FCS they were plated onto poly-lysine coated plastic at a density of two brains per 75 cc Falcon flask. After 6-10 days, the majority of cells of the oligodendrocyte lineage were removed by shaking the culture overnight. Skin fibroblasts were obtained from a flap of skin removed from P2 rat neonates. The tissue was chopped using a sterile blade and then enzymatically dissociated with trypsin and collagenase for 45 minutes. After trituration, the cells were resuspended in DMEM containing 10% FCS.

Meningeal cell cultures were obtained from the meningeal cell layer which was dissected from P2 brains, then treated as described for the astrocytic cultures.

A7 cells, an astrocyte cell line derived from postnatal brain and shown to support axon growth more readily than primary astrocytes (Fok-Seang et al., *Brain Res.* 698:207-223, 1995), were grown in DMEM containing 10% FCS.

B. Immunofluorescent Staining

Schwann cells were identified by indirect immunofluorescent labeling using polyclonal anti-growth associated protein 43 (GAP-43; a generous gift from G. Wilkie) and astrocytes were identified by the mouse monoclonal anti-glial fibrillary acidic protein (GFAP; Boehringer, Laval, Quebec). The tissue was fixed in 4% paraformaldehyde for 30 minutes, blocked with PBS-Triton X-100 (0.2%) and 5% goat serum and then given one hour of incubation with the primary antibody. Rhodamine-conjugated anti-rabbit antibodies (Jackson Immunoresearch Labs, Inc. Westgrove, Pa.; 1:200) and fluorescein conjugated anti-mouse (1:200) allowed visualization. Fibroblasts were identified with the mouse monoclonal anti-Thy1.I (Serotec, Kidlington, Oxford, UK; 1:1000) using the same staining technique.

C. The Generation of Schwann Cell and Astrocyte Cellular Boundaries

A cell boundary assay was used to study the behavior of two cell populations which have the ability to divide and migrate freely, meeting head on as continuous cellular frontiers. Schwann cells were prepared as a dense cell suspension consisting of $2\times10^6$ cells per ml of solution. 70

μl of this suspension was placed as a drop at one end of a 2 mm polylysine coated coverslip. A glass 10 mm×5 mm fragment was taken with a pair of forceps and the drop was smeared towards the center of the coverslip so as to generate a straight edge to the drop. An equal number of a different type of cells suspended in an equal volume as the first drop was then placed at the opposite end of the coverslip. Using a different glass fragment (of similar dimensions) this second drop was again smeared towards the center of the coverslip so that the straight edged boundary of this new drop was as close as possible and parallel to the edge of the first drop without the two drops mixing. The cells were allowed to attach for 2-3 hours before washing three times in Hanks to remove any non-attached cells. These cultures were then grown for three days in medium supplemented with serum, BPE and forskolin to provide a maximal mitotic stimulus to the Schwann cells. The cultures were then fixed in 4% paraformaldehyde for 20 minutes prior to immunohistochemistry. In this way, interactions between populations of Schwann cells and astroglia, and between populations of Schwann cells and fibroblasts were studied with respect to the morphology of their cellular territories.

Once confluent cultures of two cell types were established (approximately 200 μm away from one another), the cultures expanded and interacted with one another along a straight front. The interactions between the two opposing cell types were then analyzed over the course of several days. The establishment of territories between Schwann cells and astrocytic cells, and between Schwann cells and fibroblasts was studied. In each case, the two populations of cells generally came into contact after two days. Cultures consisting of Schwann cells and astrocytes were taken for immunohistochemical analysis (n=18). In all cultures, it was evident that Schwann cell and astroglial territories remained largely exclusive. The Schwann cells at the boundary were seen in two orientations. In some areas the long axes of the Schwann cells were parallel to the astrocytic boundary. Here the territories occupied by the two cell types were completely exclusive. In other areas the boundary was more complex. Groups of Schwann cells had their long axes at right angles to the cell interface, making finger-like projections, and there was often a slight degree of overlap between the two territories (FIG. 1D). Time lapse observations indicated that the astrocytes were constantly advancing, sending processes under the Schwann cells, which would then retreat as a group (data not shown). Apart from the distinctive territorial arrangements, it was observed that astrocytes in contact with Schwann cells displayed a more intense staining with GFAP and showed hypertrophy of the perikarya, as reported by previous authors both in vivo and in vitro (Brook et al., *Glia* 9:292-304,1993; Ghimikar and Eng, *Glia* 11:367-377, 1994). Schwann cells and astrocytes cultured by this method were therefore able to establish a structure similar to the peripheral nerve entry zones seen in vivo.

Figure 3B:
Figure 3C:
Figure 3D:
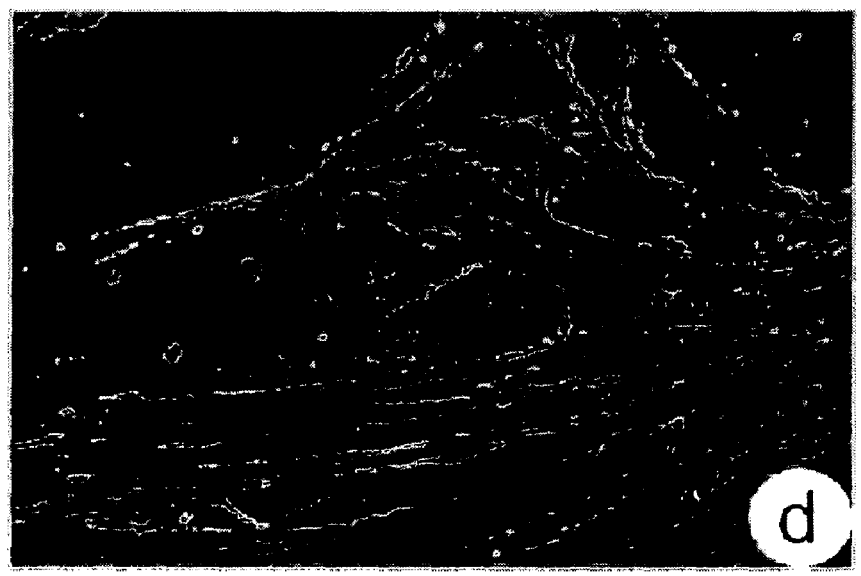

To determine whether the development of these distinctive patterns were a common feature of the manipulations peculiar to this technique, or unique for the cell types, the assay was repeated using Schwann cells and fibroblasts, cells normally associated with Schwann cell migration in damaged peripheral nerve. None of the Schwann cell-fibroblast cultures (n=15) displayed the clear territorial exclusion seen in Schwann cell-astrocyte cultures. Similarly, none of the cultures displayed the parallel Schwann cell alignment at the boundary or the finger-like projections. Indeed, Schwann cells were seen to cluster together rather irregularly and to overlie the fibroblasts. Phase contrast photographs showing the parallel alignment commonly seen in the Schwann cell-astrocyte co-cultures and the irregular clustering of the Schwann cells upon the fibroblasts are presented in FIGS. 3A and 3B.

D. Migration of Schwann cells on laminin and monolayers

In order to assess the rates of Schwann cell migration on different surfaces, the micro-inverted-coverslip migration assay was employed. This is a variation of the technique first described by Fok-Seang et al., *Dev. Biol.* 171:1-15, 1995. Schwann cells fluorescently labeled with Di-I (25 μg/ml) were evenly plated onto polylysine and laminin coated fragments of glass coverslip (1×2 mm). After 16-18 hours, the pieces of glass coated with Di-I labeled Schwann cells were dipped into Hanks three times to remove any loosely attached cells and then inverted with cells facing downwards onto laminin-coated tissue culture surfaces or onto cell monolayers. These cultures were then incubated for a further two days and fixed for 20 minutes with 4% paraformaldehyde. The maximum migration distance was measured, and the number of cells in bands of 0.1 mm progressing outwards from the edge of the coverslip were counted.

Figure 4A:
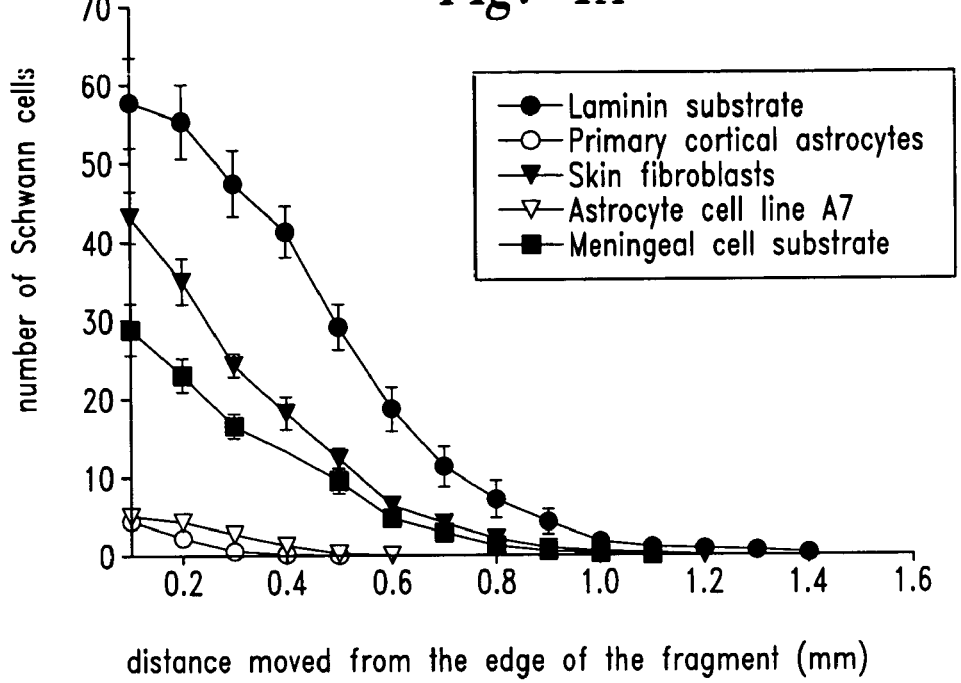

In this assay, a dense Schwann cell culture is established on coverslip fragments and their migration away from its edge measured. The assay therefore measures the ability of Schwann cells to migrate on a surface, and their ability to migrate away from a confluent Schwann cell monolayer. The migration front of the foremost cells was measured, and the number of cells against distance of migration plotted. Schwann cell-laden fragments were placed on laminin to give a baseline migration rate on a favorable defined surface, and laminin controls were done for comparison on each assay. The average distance of migration on laminin was 1.02 mm±0.06 (mean±S.E.M over three days. Migration assays were done on four different cell monolayers: (1) astrocytes cultured from postnatal brain, (2) A7 astrocyte cell line, (3) fibroblasts, and (4) meningeal cells. These results are presented in FIG. 4A.

Figure 4B:
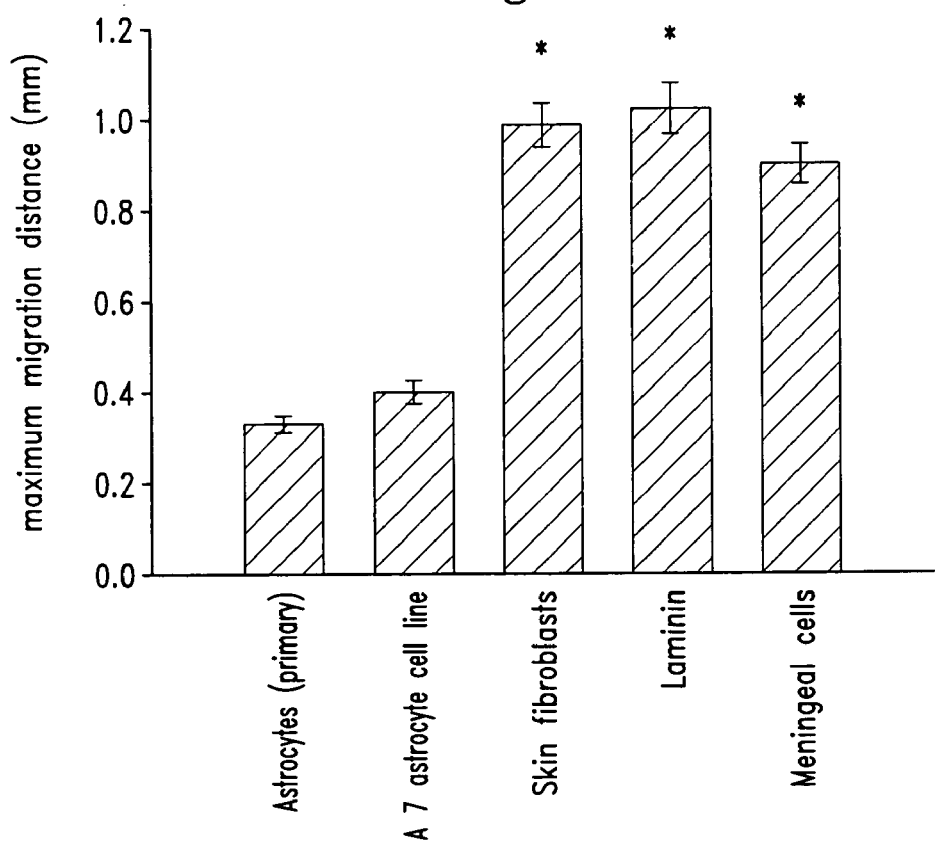

The mean maximum distance covered by the Schwann cells on an astroglial monolayer over 3 days was found to be 0.33 mm±0.02. Migration on fibroblasts was 0.99 mm±0.04 (FIG. 4B). Schwann cells can therefore migrate on fibroblasts almost as rapidly as on laminin, while migration on astrocytes is much more limited. FIGS. 12A and 12B compare the migration of Schwann cells upon astrocyte surfaces to that upon fibroblast surfaces, showing the migration of fluorescently labeled cells from the edge of the fragment.

Primary cortical astrocyte cultures purified in the manner described have been shown to yield type-I astrocyte purities greater than 95%. Contaminating cell types may include microglial cells, meningeal cells or cells of the oligodendrocyte-lineage. In order to be certain that the restricted migration of Schwann cells on astrocyte cultures was not due to the presence of small numbers of meningeal cells, which inhibit oligo-precursor migration (Fok-Seang et al., *Dev. Biol.* 171:1-15, 1995), purified meningeal cell cultures extracted from neonatal brain were used as a migratory substrate. The average distance of migration by Schwann cells on a meningeal cell monolayer was found to be 0.90 mm±0.04. This is a degree of Schwann cell migration similar to that achieved on fibroblasts and laminin, and much greater than on astrocytes.

In order to determine whether non-astrocytic contaminants were responsible for the non-permissive behavior, the astrocyte cell line A7 was used as a migratory substrate. A homogenous astroglial population permitted only 0.40 mm±0.03 of Schwann cell migration over the two day period, very similar to that seen on primary astrocyte cultures.

Thus, when confluent cultures of Schwann cells and astrocytes were placed so as to confront one another a clear division of territory resulted, comparable to the peripheral nerve entry zones. Several mechanisms could be responsible for the segregation of two different cell types and their failure to migrate over or through one another. The simplest is an inhibitory interaction, as is seen when axon growth cones meet oligodendrocytes, when axons from CNS and PNS meet, or when oligodendrocyte precursors meet meningeal cells. However, in such instances, the exploratory cell process undergoes a sudden and catastrophic collapse within a few minutes of cell contact, leading to withdrawal of the migrating cell. This "growth cone collapse" did not occur when Schwann cells met either astrocytes or fibroblasts. A second reason for failure of cells to mix could be a lack of complementary adhesion molecules; however Schwann cells adhere more strongly to astrocytes than to fibroblasts or laminin, both of which support migration.

The data presented herein demonstrate that Schwann cells form prolonged and firm contacts with astrocytes. Schwann cells are unable to move until these contacts are broken. This behavior is very similar to that seen when oligodendrocyte precursors encounter astrocytes or when a Schwann cell process encounters an axonal growth cone in the presence of external calcium. Meetings with fibroblasts result in much shorter lived contacts. The results suggest that a secreted or cell-associated factor may be involved in this interaction.

EXAMPLE 3

Identification of Cell Membrane Associated Molecules as Factors Inhibiting Schwann Cell Migration This Example illustrates the identification of molecules responsible for differential rates of Schwann cell migration.

A. Effects of Cell Matrix and Diffusible Factors on Schwann Cell Migration

Figure 5A:
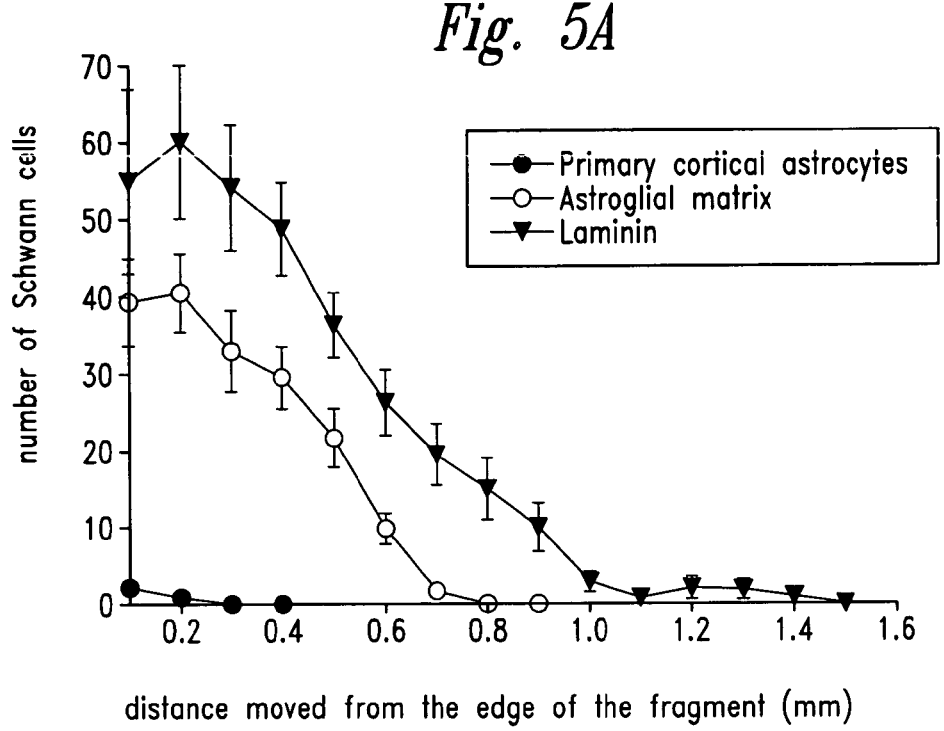
Figure 5B:
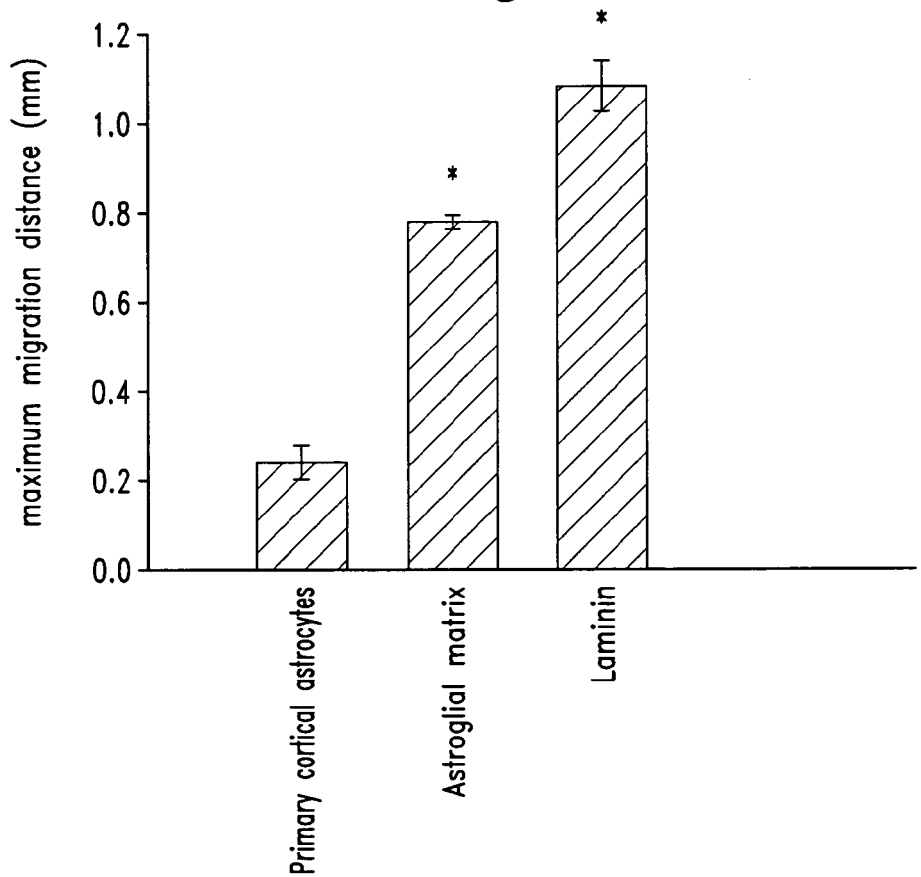

We examined whether the differential rates of Schwann cell migration on different cell types could be due either to secreted molecules, to the different properties of the extracellular matrices, or to cell membrane associated molecules (i.e., cadherin). In order to determine whether matrix or secreted molecules were responsible, we assayed Schwann cell migration on extracellular matrix and in the presence of conditioned medium. The micro inverted coverslip migration assay was employed. Surfaces laden with astroglial matrix were produced by lysing astrocytes grown on coverslips with PBS and Triton X-100 (0.1%). Schwann cell-covered fragments were inverted onto the matrix preparations and the maximum migratory distances of the cells were assessed. Control experiments were performed utilizing laminin as substrate. Schwann cells were found to migrate distances of 0.79 mm±0.02 on astroglial matrix, slightly less than that seen upon laminin (1.09 mm+0.05), but further than on whole cells (0.24 mm±0.03; FIG. 5).

Figure 6A:
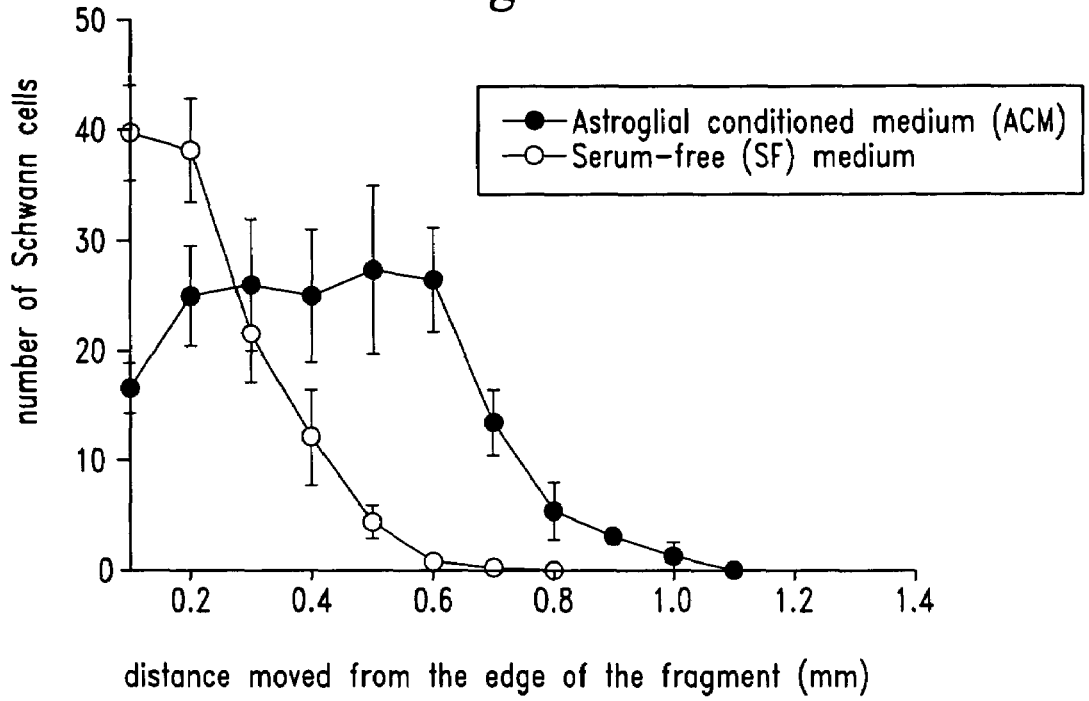
Figure 6B:
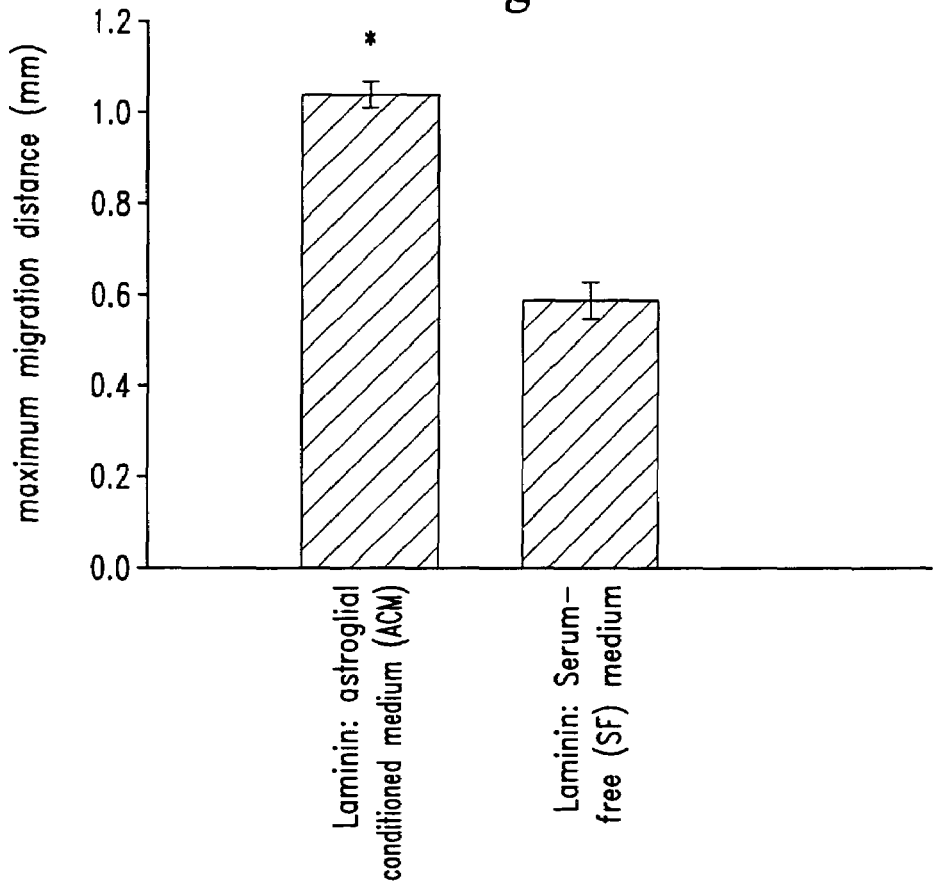

In order to assess the contribution of diffusible factors, astrocyte-conditioned serum free medium (ACM) was used to conduct Schwann cell migration assays from laminin. Schwann cells were found to have migrated distances up to 10.04 mm±0.02 upon laminin in the presence of ACM whereas migration upon laminin in serum free (SF) medium alone was 0.59 mm±0.04 (FIG. 6). It appears that pro-migratory factors exist in serum and paradoxically ACM.

These experiments suggest that neither astrocyte matrix nor secreted molecules are inhibitory to Schwann cell migration. The inhibition must therefore be cell surface mediated.

B. Movement of Single Schwann Cells on Laminin and Monolayers

The inverted coverslip migration assay described in the previous section involves a number of different cell interactions, namely Schwann cell-Schwann cell interactions and the adhesion between the Schwann cells and the overlying glass fragment. In order to analyze a simpler situation, time lapse videomicroscopy was used to determine the migration of single Schwann cells on differing cellular and proteinaceous substrates.

Cells were plated onto a 35 mm tissue culture dish and were filmed on a Nikon Diaphot inverted microscope mounted in a chamber maintained at 37° C. and at a humidified atmosphere of 10% $CO_2$ in air. The events were recorded on a Panasonic 8051 video recorder at 8 frames every 30 seconds for a period of 14-25 hours. Three types of culture were established:

1. Astrocyte, fibroblast or meningeal monolayers were grown to confluence within 35 mm tissue culture dishes and filled with 2 ml of DMEM supplemented with 10% FCS. A 50 µl Schwann cell suspension containing approximately 1000 cells was then added to the dish which was then transferred to the timelapse chamber. Filming was initiated immediately and Schwann cells were clearly identifiable landing and attaching to the underlying monolayer. Movement of the Schwann cell body was recorded every 30 minutes for 6 hour periods by marking the position of its nucleus onto an acetate sheet covering the monitor. Pathways of migration were therefore constructed. Distance moved by the cell body every half hour was measured and used to generate an average speed of migration for the cells.

2. Cultures from which interactions between single cells colliding as they moved on a laminin surface could be filmed were generated as follows: 1 ml of solution containing 1000 Schwann cells was placed into a 35 mm culture dish followed by a further 1 ml of an equal number of either astroglia or fibroblasts. The dish was transferred to a timelapse chamber and a field of view in which cells of each type were close but not yet touching was selected. The nature and duration of interactions between the different cell types were recorded.

3. Confrontation assays, in which an expanding monolayer of astrocytes or fibroblasts would come into contact with an expanding monolayer of Schwann cells, were established using the cell boundaries generated as above.

Within one such study, single Schwann cells were plated onto astrocytic, fibroblastic or laminin substrates and their cell body movement was observed over a time period of 6 hours. The position of the cell body after 30 minute intervals was noted onto an acetate sheet covering the monitor and displacement diagrams were obtained for twenty cells upon each substrate. From these diagrams, the distance moved every 30 minutes was obtained and used to generate the average migratory rates of the single cells for each of the conditions. A selection of displacement diagrams are presented as FIG. 5C. It was found that Schwann cells migrate the slowest on astrocytes with an average speed of 16.2 µm/hr±1.12. They move faster on fibroblasts (31.8 µm/hr±1.39) and attain their fastest speed on laminin (64.8 µm/hr±2.88). Therefore, the same trend as seen with the population migration experiment is seen with single Schwann cells. This data is presented graphically as FIG. 7A.

C. Interactions Between Single Schwann Cells, Astrocytes and Fibroblasts

Sparse mixed cultures of Schwann cells and either astrocytes or fibroblasts were established. Regions where single Schwann cells were in contact with isolated astrocytes or fibroblasts were filmed. Astrocyte-Schwann cell (n=50) and fibroblast-Schwann cell (n=40) interactions were observed. When a Schwann cell process encountered an astrocyte, the exploratory growth cone first appeared to attach firmly to the astrocytic surface and then expand in area, with active lamellipodia exploring the perikarya. The growth cone could be seen to become anchored to the astrocyte whilst the cell body would move away, resulting in a very long process connecting the two cells. The average process length was found to be 33.0 µm±3.0 (mean±S.E.M.). In contrast Schwann cells encountering fibroblasts did so via an exploratory growth cone which did not expand on contact. Furthermore, the average process length between Schwann cells and fibroblasts was found to be 11.8 µm±1.85. The longer processes developing between Schwann cells and astrocytes implies greater tension between the cells.

Contacts between Schwann cells and astrocytes were of much longer duration than those between Schwann cells and fibroblasts. Most (80%) of the Schwann cell-astrocyte interactions were longer than 90 minutes. In comparison, only 5% of the Schwann cell-fibroblast interactions were as long as this. The average length of interaction between Schwann cells and astrocytes was found to be 257 min±41 minutes whereas the average Schwann cell-fibroblast-interaction was found to be 48 min±5 (FIG. 7B). A sequence of encounters between a Schwann cell and an astrocyte captured from a time lapse recording is presented in FIG. 6. Each consecutive frame represents a time interval of 2 hours. Thus, Schwann cells appear to interact with astrocytes and fibroblasts differently at the single cell level. Schwann cells display an exploratory behavior as well as a static form of interaction with astrocytes. Contact with fibroblasts seems only to involve simple exploration with little interruption of Schwann cell migratory movement.

D. Adhesion of Schwann Cells to Laminin and Monolayers

In order to test whether the migratory behavior of Schwann cells on different cell types was a function of adhesivity to the substratum, DiI-labeled Schwann cells were plated onto either astrocytic, fibroblasts, Schwann cell or laminin surfaces. 20,000 DiI-labeled Schwann cells were placed in a 15 mm diameter well in 0.5 ml of medium over a 13 mm glass coverslip coated with laminin, or a complete monolayer of astrocytes, fibroblasts or Schwann cells and then placed onto a shaking platform (25 rpm) for 30 minutes in an incubator. The coverslips were washed three times in Hanks after 30 minutes to remove any non-attached cells and the remainder were fixed for 20 minutes in 4% paraformaldehyde. The number of DiI-labeled Schwann cells that were attached to the coverslip were counted using a Leitz Diaplan fluorescent microscope under rhodamine optics.

Figure 7C:
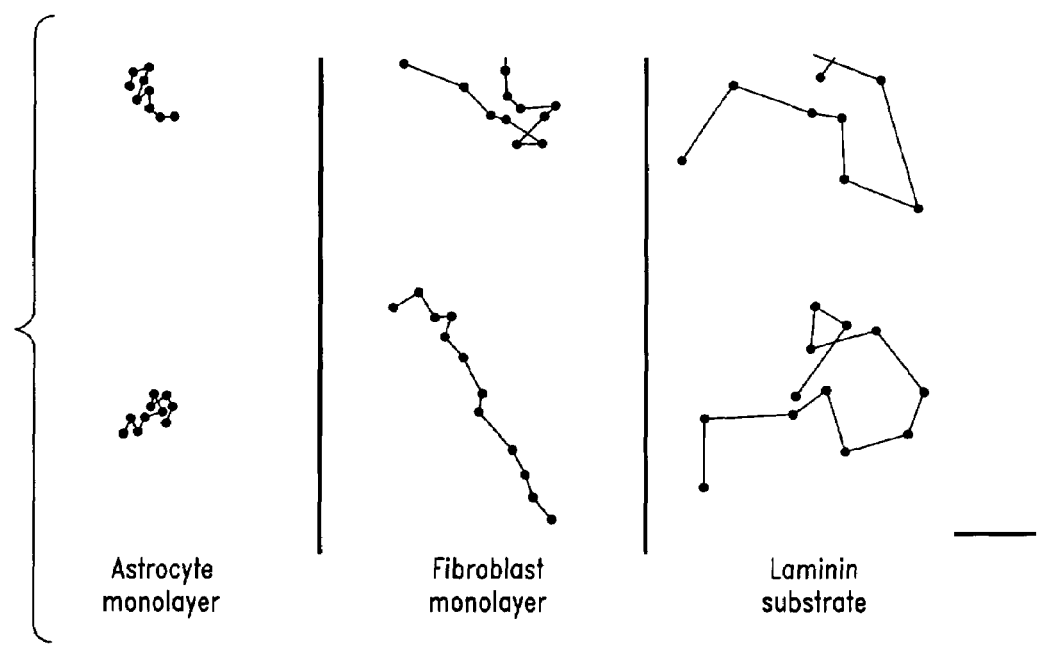

The data was normalized by setting Schwann cell adhesion to astrocytes at the arbitrary value of 1±0.03 (mean±S.E.M.). More than twice the number of cells adhered to the astrocytic surfaces as compared to either the fibroblastic (0.49±0.02) or laminin surfaces (0.35±0.02). The most adhesive substrate was found to be Schwann cell monolayers, with adhesion values of 1.58±0.1, compared to astrocytes (FIG. 7). The anti-migratory astrocyte surface is therefore more adhesive to Schwann cells than are fibroblastic surfaces with in turn are slightly more adhesive than laminin-coated surfaces. There is therefore an inverse correlation between rate of Schwann cell migration and adhesion.

The results presented herein show that ACM promoted the migration of Schwann cells in the absence of serum, and astrocyte matrix is only a little less good than laminin as a migratory surface. This suggests that the majority of the anti-migratory activity displayed by astrocytes is due to interactions with cell surface associated molecules.

EXAMPLE 4

Effect of Representative Modulation Agents on Schwann Cell Adhesion and Migration The cadherins are known to mediate calcium-dependent cell adhesion (Redies and Takeichi, *Dev. Biol.* 180:413-423, 1996; Munro and Blaschuk, "The Structure, Function and Regulation of Cadherins," in *Cell Adhesion and Cancer Metastasis (P. Brodt ed.)* pp. 17-34 (R. G. Landes Co., 1996). Lowering the external calcium to 0.2 mM has been shown to disrupt cadherin-mediated interactions between Schwann cells and other cell types (Letourneau et al., *Neurobiol.* 22:707-720, 1991). This example illustrates the use of calcium or two representative modulating agents to disrupt cadherin function and increase Schwann cell migration.

A. The Effect of Lowering External Calcium Concentrations on Schwann cell Adhesion and Migration In order to reduce extracellular calcium, DMEM was replaced by S-MEM (Joklik's modification; Gibco) with 0.2 mM calcium chloride added or the calcium buffer EGTA (Sigma) was employed. Adhesion assays in the absence of external calcium were performed using Schwann cells and astrocytes. Either a low calcium solution (S-MEM in place of DMEM with 0.2 mM calcium chloride) or a calcium buffer (EGTA in a normal DMEM medium) was used in these assays. Various concentrations of EGTA were tested; the optimal concentration for Schwann cell migration was found to be 1.6 mM. EGTA concentrations less than 1.3 mM had little effect upon Schwann cell migration whereas those above 1.8 mM caused disruption of the astrocytic monolayer (data not shown). Adhesion of Schwann cells to astrocytes in the presence of the standard DMEM based medium was taken as the control and assigned the normalized value of 1.0±0.03. Low calcium solutions reduced intercellular adhesion to 0.47±0.09 and the addition of 1.6 mM EGTA to DMEM reduced adhesion to 0.39±0.05 (FIG. 10A). EGTA, being the more effective adhesion inhibitor, was incorporated into the migration assay and found to increase the extent of Schwann cell migration upon astrocyte monolayers to 0.86 mm±0.06 compared to control migration (0.25±0.03; FIGS. 10B and 10C).

B. The Effect of Representative Modulating Agents on Adhesion and Migration

The following modulating agents were employed at concentrations of 1 mg/ml, LRAHAVDING-NH$_2$ (SEQ ID NO: 21), MRAHAVDING-NH$_2$ (SEQ ID NO: 23), and the control peptide LRAHGVDING-NH$_2$ (SEQ ID NO: 30). The former two peptide modulating agents harbor the cadherin CAR sequence, HAV. Cadherin function was also blocked utilizing the rabbit anti-cadherin CAR sequence antiserum designated as L7 (1:20). Normal rabbit serum (NRS; Sigma, St. Louis, Mo.) and the goat anti-neural cell adhesion molecule (NCAM) antiserum (Santa Cruz Biotechnology Inc., Santa Cruz, Calif.) were also used at a dilution of 1:20 as controls.

The modulating agents LRAHAVDING-NH$_2$ (SEQ ID NO: 21) and MRAHAVDING-NH$_2$ (SEQ ID NO: 23) were found to reduce Schwann cell-astrocyte adhesion (0.38±0.07 and 0.39±0.04, respective) as compared to the normalized adhesion in the absence of peptide (1.0±0.05). The control peptide LRAHGVDING-NH$_2$ (SEQ ID NO: 21) did not significantly alter Schwann cell-astrocyte adhesion (0.78±0.10; p>0.05; FIG. 11A). Furthermore, the rabbit antiserum L7, shown to be specific for the cadherin CAR sequence (Alexander et al., *J. Cell Physiol.* 156:610-618, 1993) and reported to block N-cadherin mediated adhesion (Newton et al., *Dev. Dynamics* 197:1-13,1993) reduced Schwann cell-astrocyte adhesion to 0.39±0.06 as compared to the normalized control adhesion 1.0±0.09 in the absence of antibody. This effect was not due to non-specific factors within the antibody sera as rabbit serum had little effect upon intercellular adhesion (0.96±0.05). The control and NCAM antibody also did not affect intracellular adhesion (0.99±0.08).

As a further control, the entire adhesion experiment was repeated using Schwann cell monolayers as the adhesive substrate, thereby assaying Schwann cell-Schwann cell adhesion. The antiserum L7 was found to disrupt Schwann cell-Schwann cell adhesion to a value of 0.5±0.05 compared to the normalized control adhesion 1.0±0.16. The addition of NRS and the polyclonal NCAM antibody yielded adhesion values of 0.96±0.06 and 0.99±0.08, respectively (FIG. 11B). Having shown the ability of L7 to disrupt both Schwann cell-astrocyte and Schwann cell-Schwann cell adhesion, the antibody was employed within the migration assay. Schwann cells were found to migrate poorly on astrocytes in the presence of control medium (0.16 mm±0.03), NRS (0.12 mm 0.02) or polyclonal anti-NCAM (0.15 mm±0.02). In comparison treatment of the cultures with the L7 antiserum more than tripled the maximum migration distance of Schwann cells on astrocytes (0.51 mm±0.04; FIGS. 9C, 9D, 10C, and 10D). This effect was not due to disruption of the astroglial monolayer which remained intact (FIG. 10C).

Thus, disrupting cadherin function alters Schwann cell adhesion and migration. Schwann cells adhere to astrocytes more strongly than to fibroblasts and laminin, and nearly as strongly as to other Schwann cells. In the above experiments, the number of cells adhering to astrocytes was halved by subjecting cultures to calcium withdrawal or by treating the cells either with modulating agents containing the cadherin CAR sequence or with the L7 antiserum which is directed against the CAR sequence. Schwann cell-Schwann cell adhesion was also reduced by L7 antiserum. Both calcium withdrawal and the presence of L7 antiserum increased the rate of Schwann cell migration on astrocytes approximately three-fold.

These results demonstrate that modulating agents containing the cadherin CAR sequence and antibodies directed against that sequence are capable of disrupting cadherin function. These results also indicate that the main family of CAMs involved in Schwann cell adhesion and migration are the cadherins, and that blocking cadherin mediated adhesive interactions provides a viable approach for enhancing Schwann cell migration within the CNS. Modulating agents capable of interfering with cadherin function may be used to facilitate the grafting of Schwann cells into the CNS to promote remyelination of axon regeneration, and for other purposes where a modulation of cell adhesion is desired.

From the foregoing, it will be evident that although specific embodiments of the invention have been described herein for the purpose of illustrating the invention, various modifications may be made without deviating from the spirit and scope of the invention.

What is claimed is:

1. A method for modulating cell adhesion of cadherin-expressing cells comprising contacting the cells with a linear peptide that is 6-50 amino acid residues in length and that comprises two or more of the cell adhesion recognition sequence, His-Ala-Val, wherein said linear peptide modulates cell adhesion.

2. A method according to claim 1, wherein said linear peptide comprises a sequence selected from the group consisting of HAVHAV (SEQ ID NO: 10), SHAVSHAVSHAVS (SEQ ID NO: 11), and derivatives of the foregoing sequences having one or more C-terminal and/or N-terminal modifications.

3. A method according to claim 1, wherein said linear peptide further comprises at least one separate cell adhesion recognition sequence bound by an adhesion molecule other than a classical cadherin.

4. A method according to claim 1, wherein said two or more of the cell adhesion recognition sequences, His-Ala-Val, are separated by a linker.

5. A method according to claim 3, wherein said separate cell adhesion recognition sequence comprises a sequence selected from the group consisting of: RGD, YIGSR (SEQ ID NO: 12), KYSFNYDGSE (SEQ ID NO: 13), IWKHKGRDVILKKDVRF (SEQ ID NO: 14), YAT, FAT, YAS, RAL, QSSGSLYGSQ (SEQ ID NO: 16) and QYLYHYCVVD (SEQ ID NO: 17).

6. A method according to claim 1, wherein said linear peptide is present within a pharmaceutical composition comprising a pharmaceutically acceptable carrier.

7. A method according to claim 6, wherein said pharmaceutical composition further comprises at least one separate cell adhesion recognition sequence bound by an adhesion molecule other than a classical cadherin.

8. A method according to claim 7, wherein said separate cell adhesion recognition sequence comprises a sequence selected from the group consisting of: RGD, YIGSR (SEQ ID NO: 12), KYSFNYDGSE (SEQ ID NO: 13), IWKHKGRDVILKKDVRF (SEQ ID NO: 14), YAT, FAT, YAS, RAL, QSSGSLYGSQ (SEQ ID NO: 16) and QYLYHYCVVD (SEQ ID NO: 17).

* * * * *